(12) United States Patent
Zhu et al.

(10) Patent No.: US 11,041,042 B2
(45) Date of Patent: Jun. 22, 2021

(54) SILICONE URETHANE UREA COPOLYMER AND PREPARATION AND USE THEREOF

(71) Applicant: Dow Silicones Corporation, Midland, MI (US)

(72) Inventors: Bizhong Zhu, Midland, MI (US); Martin Grasmann, Midland, MI (US)

(73) Assignee: Dow Silicones Corporation, Midland, MI (US)

( * ) Notice: Subject to any disclaimer, the term of this patent is extended or adjusted under 35 U.S.C. 154(b) by 41 days.

(21) Appl. No.: 16/486,161

(22) PCT Filed: Nov. 17, 2017

(86) PCT No.: PCT/US2017/062170
§ 371 (c)(1),
(2) Date: Aug. 15, 2019

(87) PCT Pub. No.: WO2018/151780
PCT Pub. Date: Aug. 23, 2018

(65) Prior Publication Data
US 2020/0002460 A1 Jan. 2, 2020

(30) Foreign Application Priority Data
Feb. 15, 2017 (EP) .................... 17305166

(51) Int. Cl.
| | | |
|---|---|---|
| C08G 18/61 | (2006.01) | |
| C08G 18/81 | (2006.01) | |
| C08G 18/18 | (2006.01) | |
| C08G 18/42 | (2006.01) | |
| C08G 18/44 | (2006.01) | |
| C08G 18/48 | (2006.01) | |
| A61F 13/00 | (2006.01) | |
| A61K 9/70 | (2006.01) | |

(52) U.S. Cl.
CPC .......... *C08G 18/61* (2013.01); *C08G 18/18* (2013.01); *C08G 18/4283* (2013.01); *C08G 18/44* (2013.01); *C08G 18/4825* (2013.01); *C08G 18/4841* (2013.01); *C08G 18/4845* (2013.01); *C08G 18/8166* (2013.01); *A61F 13/00* (2013.01); *A61F 2013/00702* (2013.01); *A61K 9/7069* (2013.01)

(58) Field of Classification Search
CPC .......... C08G 18/61; C08G 18/81–8191; C08G 18/48–5018; C08G 18/67–679; C09J 175/14; C09J 175/16
See application file for complete search history.

(56) References Cited

U.S. PATENT DOCUMENTS

| | | |
|---|---|---|
| 3,159,601 A | 12/1964 | Ashby |
| 3,220,972 A | 11/1965 | Lamoreaux |
| 3,296,291 A | 1/1967 | Chalk et al. |
| 3,418,593 A | 12/1968 | Willing |
| 3,516,946 A | 6/1970 | Modic |
| 3,814,730 A | 6/1974 | Karstedt |
| 3,989,668 A | 11/1976 | Lee et al. |
| 4,122,029 A | 10/1978 | Gee et al. |
| 4,684,538 A | 8/1987 | Klemarczyk |
| 4,766,176 A | 8/1988 | Lee et al. |
| 4,784,879 A | 11/1988 | Lee et al. |
| 4,793,555 A | 12/1988 | Lee et al. |
| 4,840,796 A | 6/1989 | Sweet et al. |
| 4,929,669 A | 5/1990 | Jensen |
| 4,951,657 A | 8/1990 | Pfister et al. |
| 5,017,654 A | 5/1991 | Togashi et al. |
| 5,036,117 A | 7/1991 | Chung et al. |
| 5,075,399 A | 12/1991 | Ahmed et al. |
| 5,082,886 A | 1/1992 | Jeram et al. |
| 5,155,149 A | 10/1992 | Atwater et al. |
| 5,175,325 A | 12/1992 | Brown et al. |
| 5,258,211 A | 11/1993 | Momii et al. |
| 5,356,706 A | 10/1994 | Shores |
| 5,387,417 A | 2/1995 | Rentsch |
| 5,574,122 A | 11/1996 | Yeske et al. |
| 5,643,581 A | 7/1997 | Mougin et al. |
| 5,756,572 A | 5/1998 | Sweet et al. |
| 5,811,487 A | 9/1998 | Schulz, Jr. et al. |
| 5,919,441 A | 7/1999 | Mendolia et al. |
| 5,919,884 A | 7/1999 | Fink et al. |
| 5,981,680 A | 11/1999 | Petroff et al. |
| 5,986,018 A | 11/1999 | Yamaguchi et al. |
| 5,998,694 A | 12/1999 | Jensen et al. |
| 6,051,216 A | 4/2000 | Barr et al. |

(Continued)

FOREIGN PATENT DOCUMENTS

| | | |
|---|---|---|
| CN | 201333128 | 10/2009 |
| CN | 202283306 | 6/2012 |

(Continued)

OTHER PUBLICATIONS

Abstract for CN 103483537 (Jan. 2014).*
Machine translation of CN 103483537 into English (no date).*
Ferris, et al, "Synthesis of Functional Sugar-Based Polyurethanes" Macromlecular Chemistry and Physics., vol. 213, No. 5, Mar. 16, 2012, pp. 480-488, XP055452383 DE IDDS: 1022-1352, DOI: 10.1002/macp.201100672 abstract.
Balaban, The effect of polar solvents on the synthesis of poly(urethane-urea-siloxane)s, Journal of the Serbian Chemical Society, 2012, p. 1457-1481.
Borde, "Increased water transport in PDMS silicone films by addition of excipients" Acta Biomaterialia 8 (2012) 579-588.
Chen-Chi, "Intermolecular and Intramolecular Hydrogen Bonding of Poly(dimethylsiloxane)urethane-Graft_Ploy(methylmethacrylate) Copolymers Based on 2,4-TDI and m-XDI" J. App. Polym. Sci., 2002, 962-972.

(Continued)

*Primary Examiner* — Marc S Zimmer
(74) *Attorney, Agent, or Firm* — Catherine U. Brown

(57) ABSTRACT

A silicone urethane urea copolymer and methods for preparation and use of the copolymer are disclosed. The copolymer is crosslinkable. The copolymer is useful in various applications, including personal care compositions, such as hair care compositions and skin care compositions and in health care compositions such as skin contact adhesive compositions and transdermal drug delivery systems.

8 Claims, 4 Drawing Sheets

(56) References Cited

U.S. PATENT DOCUMENTS

| | | |
|---|---|---|
| 6,524,564 B1 | 2/2003 | Kim et al. |
| 6,528,121 B2 | 3/2003 | Ona et al. |
| 6,623,537 B1 | 10/2003 | Shores |
| 6,746,765 B1 | 6/2004 | Fattman |
| 6,858,218 B2 | 2/2005 | Lai et al. |
| 6,884,853 B1 | 4/2005 | Asaoka et al. |
| 6,916,464 B2 | 7/2005 | Hansenne et al. |
| 7,074,873 B2 | 7/2006 | Lai et al. |
| 7,423,074 B2 | 9/2008 | Lai et al. |
| 7,452,956 B2 | 11/2008 | Cheng et al. |
| 7,914,160 B2 | 3/2011 | Sugano |
| 8,377,425 B2 | 2/2013 | Fleissman et al. |
| 8,507,081 B2 | 8/2013 | Strobech et al. |
| 8,760,100 B2 | 6/2014 | Shafer et al. |
| 8,785,587 B2 | 7/2014 | Wagner et al. |
| 8,877,885 B2 | 11/2014 | Vyakaranam et al. |
| 9,492,171 B2 | 11/2016 | Patenaude |
| 9,688,879 B2 | 6/2017 | Chen et al. |
| 9,976,041 B2 | 5/2018 | Fu et al. |
| 10,092,441 B2 | 10/2018 | Lee |
| 10,369,096 B2 | 8/2019 | Sakamoto et al. |
| 2002/0040202 A1 | 4/2002 | Levin |
| 2002/0132909 A1 | 9/2002 | Klanica et al. |
| 2002/0198280 A1 | 12/2002 | Baba et al. |
| 2003/0072730 A1 | 4/2003 | Toumilhac |
| 2003/0142526 A1 | 7/2003 | Nakahara et al. |
| 2003/0170188 A1 | 9/2003 | Ferrari et al. |
| 2003/0235552 A1 | 12/2003 | Yu |
| 2003/0235553 A1 | 12/2003 | Lu et al. |
| 2004/0091692 A1 | 5/2004 | Parrinello et al. |
| 2004/0180032 A1 | 9/2004 | Manelski et al. |
| 2004/0254325 A1 | 12/2004 | Keupher et al. |
| 2005/0048104 A1 | 3/2005 | Venkatraman et al. |
| 2005/0163978 A1 | 7/2005 | Strobech et al. |
| 2005/0238611 A1 | 10/2005 | Rando et al. |
| 2006/0036055 A1 | 2/2006 | Schafer et al. |
| 2006/0142526 A1 | 6/2006 | Lai et al. |
| 2006/0247403 A1 | 11/2006 | Nguyen-Kim et al. |
| 2007/0027285 A1 | 2/2007 | Gunatillake et al. |
| 2007/0071700 A1 | 3/2007 | Abhimanyu Patil et al. |
| 2007/0093618 A1 | 4/2007 | Cheng et al. |
| 2007/0154440 A1 | 7/2007 | Fleissman et al. |
| 2007/0172518 A1 | 7/2007 | Raul et al. |
| 2008/0027366 A1 | 1/2008 | Da Silva Macedo, Jr. |
| 2009/0105670 A1 | 4/2009 | Bentley et al. |
| 2010/0098648 A1 | 4/2010 | Yu |
| 2011/0034847 A1 | 2/2011 | Bougherara |
| 2014/0142490 A1 | 5/2014 | Johannison |
| 2014/0323941 A1 | 10/2014 | Lee |
| 2015/0031797 A1 | 1/2015 | Onodera et al. |
| 2015/0086713 A1 | 1/2015 | Chen et al. |
| 2015/0313593 A1 | 11/2015 | Patenaude |
| 2017/0319463 A1 | 11/2017 | Sakamoto et al. |
| 2018/0009997 A1 | 1/2018 | Bhagwagar et al. |
| 2018/0023245 A1 | 1/2018 | Dams et al. |
| 2019/0218418 A1* | 7/2019 | Cheng ............... C08G 18/755 |

FOREIGN PATENT DOCUMENTS

| | | |
|---|---|---|
| CN | 102757705 | 10/2012 |
| CN | 201864218 | 12/2015 |
| CN | 103937437 | 8/2016 |
| DE | 69817234 | 5/2014 |
| EP | 0347895 | 12/1989 |
| EP | 1266647 | 12/2002 |
| EP | 1266648 | 12/2002 |
| EP | 1266653 | 12/2002 |
| EP | 3127931 | 8/2017 |
| WO | 2003105789 | 12/2003 |
| WO | 2003106614 | 12/2003 |
| WO | 2004000247 | 12/2003 |
| WO | 2004054523 | 7/2004 |
| WO | 2004054524 | 7/2004 |
| WO | 2004060101 | 7/2004 |
| WO | 2007092350 | 8/2007 |
| WO | 2008088491 | 7/2008 |
| WO | 2013011691 | 1/2013 |
| WO | 2013030580 | 3/2013 |
| WO | 2014116281 | 7/2014 |
| WO | 2015075448 | 5/2015 |
| WO | 2015097064 | 7/2015 |
| WO | 2015152110 | 10/2015 |
| WO | 2018052644 | 3/2018 |
| WO | 2018052645 | 3/2018 |
| WO | 2018052647 | 3/2018 |
| WO | WO 2018/059561 | * 4/2018 |

OTHER PUBLICATIONS

Chein-Hong, "Novel siliconehydrogel based on PDMS and PEGMA for contact lens application" olloids and Surfaces B: Biointerfaces 123 (2014) 986-994.

Chein-Hong, "Hemocompatibility and cytocompatibility of styrenesulfonate-grafted PDMS-polyurethane-HEMA Hydrogel" Colloids and Surfaces B: Biointerfaces 70 (2009) 132-141.

Ching-Hsien, "Designed drug-release systems having various breathable polyurethane film-backed hydrocolloid acrylated adhesive layers for moisture healing" 2081-2088.

Chung, "Cheracterization and low temperature test of the flexibly crosslinked polyurethane copolymer by poly(dimethylsiloxane)" High Performance Polymenrs, 24(3), 200-209.

Delvalle, Cindy, et. al., "Personal Care Applications for Phenylsilsesquioxane Resins," IP.com, 2016, No. IPCOM000248667D.

Dolmaire, "Modification of the Hygrophilic Linear Polyurethane by Crosslinking with a Polydimethylsiloxane. Influence of the Crosslink Density and of the Hydrophobic/Hydrophilic Balance on the Water Transport Properties." Journal of Polymer Science, vol. 44, p. 48-61.

Dzunuzovic, "Investigation of the Morphology and Surface Properties of Crosslinked Poly(Urethane-Ester-Siloxane)s" Hem. Ind. 66 (6) 813-821 (2012). English Summary.

Dzunuzovic, "Synthesis and swelling behavior of polyurethane networks based on hyperbranched polymer" Hem Ind. 65 (6) 637-644 (2011).

Ekin. "Combinatorial and High-Throughput Screening of the Effect of Siloxane Composition on the Surface Properties of Crosslinked Siloxane-Polyurethane Coatings" J. Comb. Chem. 2007, 9, 178-188.

Fang, et al., "New formulations capabilities with three new silicone resin flake products", IP.com Prior Art Database Technical Disclosure.

Garaud, et al., "A Second Generation Silicone Acrylate for us in Beauty Care Applications", IP.com Prior Art Database Technical Disclosure.

Ioan, "Dymanic-machanical and differential scanning calorimetry measurements on crosslinked poly(ester-siloxanes)-urethanes", Polymer 42, 2001, p. 3633-3639.

Jaing, Moisture-Cured Polyurethane/Polysiloxane Copolymers: Effects of the Structure of Polyester Diol and NCO/OH Ratio J. App. Polym. Sci., 2008.

Klode, et al., "Investigation of adhesion of modern wound dressings: a comparative analysis of 56 different wound dressings", Journal of European Academy of Dermatology and Venereology, 2011, 25, pp. 933-939.

Kozakiewicz, "Water-cured poly(urethane-urea)s containing soft segments originating from siloxane/carbonate macrodiols", Polimery, 2012, p. 933-939.

Krawczyk, Tobias, "Siloxane modification of polyurethane resins for application in coatings to improve the properties of the film" Master's thesis.

Manriquez, "Evaluation of a New Silicone Adhesive Tape among Clinicians Caring for Patients with Fragile or At-Risk Skin", 2014, p. 163-173, Lippincott Williams & Wilkins.

Mikhailova, "Heat-Resistant and Anti-Corrosion Urethane-Silicone-based Coatings", 2012. p. 197-208.

Oktay, "Polydimethylsiloxane (PDMS)-based antibacterial organic-inorganic hybrid coatings" J. Coat, Technol. Res., 10(6) 785-798, 2013.

(56) References Cited

OTHER PUBLICATIONS

Pergal, "Microstructure and properties of poly(urethane-silicone)s based on hyperbranched polyester of the fourth pseudo generation", Progress in Organic Coatings, 2013, p. 743-756.

Pergal, "Poy(urethane-siloxane)s based on hyperbranched polyester as crosslinking agent: synthesis and characterization", Journal of the Serbian Chemical Society, 2012, p. 919-935.

Pergal, "Study on the morphology and thermomechanical properties of poly(urethane-siloxane) networks based on hyperbranched polyester" Hem. Ind. 67 (6) 871-879 (2013).

Pergal, "Surface and thermomechanical characterization of polyurethane networks based on poly(dimethylsiloxane) and hyperbranched polyester" eXPRESS Polymer Letters vol. 7, No. 10 (2013) 806-820.

Pieper, "Cominatorial approach to study the effect of acrylic polyol composition on the properties of crosslinked siloxane-polyurethane fouling-release coatings" J. Coat. Technol. Res., 4 (4) 453-461, 2007.

Pusztai, "The effect of some disiloxane chain extenders on the thermal and mechanical properties of cross-linked poly(siloxane-urethanes)s" eXPRESS Polymer Letters vol. 7, No. 5 (2013) 456-470.

Souliotis, "A cost and clinical effectiveness analysis among wound healing dressings versus traditional methods in home care patients with pressure ulcers", 2016-p. 596-601.

Yang, "Preparation and Surface Properties of Silicone-Modified Polyester-Based Polyurethane Coats", JCT Research, vol. 3, No. 4, Oct. 2006.

Young-Hee. "Synthesis and Properties of Waterborne Poly(urethaneurea)s Containing Polydiemthylsiloxane" J. App, Polym. Sci., 2010.

Yuan, et al., "Allyl ether Modified UV Curable Polyurethane-acrylate Resins", Chinese Journal of Applied Chemistry, vol. 20, No. 8, Aug. 2003.

Zhu, Synthesis and Thermal Properties of Polyurethane-Polysiloxane Crosslinked Polymer Networks J. App. Poly. Sci., 2003.

\* cited by examiner 100
101
104
102
105
103

Figure 2A
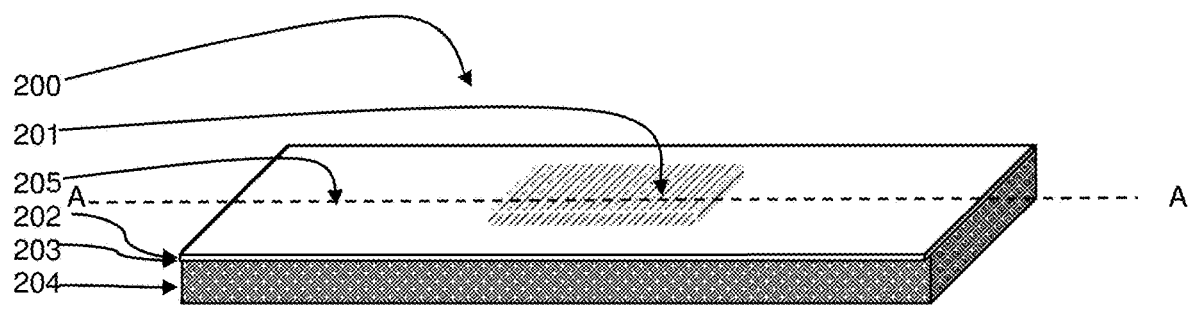
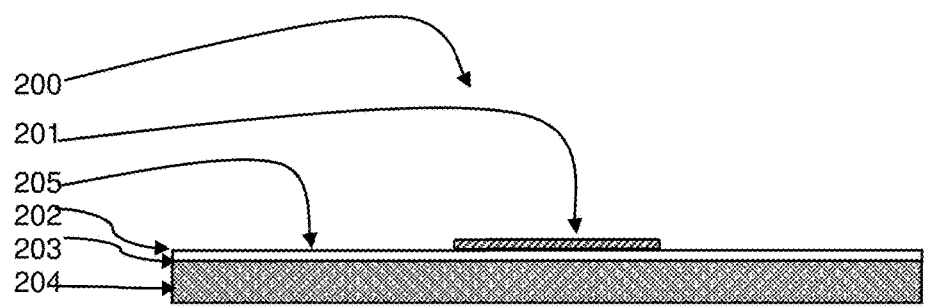
Figure 2B

SILICONE URETHANE UREA COPOLYMER AND PREPARATION AND USE THEREOF

CROSS REFERENCE TO RELATED APPLICATIONS

This application claims priority to PCT Application Serial No. PCT/US17/047466 filed on 18 Aug. 2017; PCT Application Serial No. PCT/US17/047467 filed on 18 Aug. 2017; PCT Application Serial No. PCT/US17/047469 filed on 18 Aug. 2017; and European Patent Application Serial No. 17305166.5 filed on 15 Feb. 2017. PCT Application Serial No. PCT/US17/047466; PCT Application Serial No. PCT/US17/047467; PCT Application Serial No. PCT/US17/047469; and European Patent Application Serial No. 17305166.5 are each herby incorporated by reference.

TECHNICAL FIELD

A silicone urethane urea copolymer ("copolymer") and methods for preparation of the copolymer are disclosed. The copolymer is crosslinkable. The copolymer is useful in various applications, including personal care compositions, such as hair care compositions and skin care compositions and in health care compositions such as skin contact adhesive compositions and transdermal drug delivery systems.

BACKGROUND

Silicone resins (such as MQ and MQ-T type resins) have been used as film forming agents in personal care compositions. These silicone resins may suffer from the drawback of providing insufficient abrasion resistance (resistance to wear off) to the personal care compositions, or in some other instances may be too brittle and develop cracks relatively easily. Polyurethanes are being used also for these applications. While they have better abrasion resistance they can suffer from inferior water resistance and other disadvantages as compared with silicone resins.

Various types of skin contact adhesives have been proposed for skin contact applications such as adhesives for medical tapes, adhesives for wound dressings, adhesives for prosthetics, ostomy appliance adhesives, adhesives for medical monitoring appliances, adhesives for scar therapy treatments, and transdermal drug delivery systems. Hydrocolloid adhesives and acrylate adhesives typically have the highest adhesion (e.g., require the highest energy to remove from the skin). Polyurethane adhesives have the next highest adhesion, and silicones have the lowest adhesion of these types of skin contact adhesives. Those skin contact adhesives with higher adhesion (requiring higher energy to remove) can cause more pain and potential trauma to the skin during removal than those with lower energy required for removal. Certain skin contact adhesives may also leave an undesirable residue on skin during removal.

In the process of chronic wound care, adhesive wound dressings and/or medical tapes, may cause pain and injury in and around the wound during dressing changes. Repeated application and removal of skin contact adhesives can be painful and traumatic, especially for patients with fragile skin. Fragile skin is generally characterized by thin skin that tears easily and may be more common in older adults than other populations. Aging, sun exposure, and genetics all play a role in thinning of the skin. Certain medications, such as long-term use of oral or topical corticosteroids, can also weaken skin and the blood vessels within the skin and make it more vulnerable to trauma associated with removal of adhesives. Individuals with fragile skin can also experience a loss of cohesion between the epidermis and dermis and between the dermis and subcutaneous tissue, making these individuals more prone to skin tears and trauma, particularly when skin contact adhesives with higher adhesion are used.

Furthermore, silicone adhesives, e.g., those prepared from two part catalyzed silicone elastomers, may be unsuitable for use in certain skin contact adhesive applications, such as transdermal drug delivery. Certain catalysts used to prepare silicone elastomers (such as platinum group metal catalysts for hydrosilylation) may detrimentally affect the medically active ingredient in transdermal drug delivery devices, or the medically active ingredients may render the catalyst ineffective for elastomer preparation.

In addition to skin contact adhesives, polyurethanes and polyorganosiloxanes are also used for coatings applied on various substrates. Polyurethanes are known to have high mechanical toughness but have limitations such as limited temperature resistance, moisture resistance, and radiation stability. Polyorganosiloxanes are environmentally very stable. Incorporating some polyorganosiloxane into a polyurethane based coating is challenging in the industry because the chemical natures of polyorganosiloxanes and polyurethanes have very limited compatibility.

Problem to be Solved

There is an industry need to develop compositions that can be applied to skin or hair with one or more of the following benefits: good film forming properties, good adhesive properties, ability to transfer an active ingredient e.g., in transdermal drug delivery applications, moisture resistance (from the environment to the skin), water transport from the skin to the environment, stability, minimal skin irritation, minimal damage to the skin during use and removal, and/or minimal residue on skin during and after removal. There is also an industry need to develop a composition that can be used to form a coating on a substrate with one or more of the following benefits: improved compatibility between polyurethane and silicones, improved weathering resistance, hydrophobicity, hydrolytic stability, radiation resistance, thermal resistance, corrosion resistance, surface smoothness and gloss, scratch resistance, lower viscosity at similar solid content (impacting volatile organic content, VOC), and reduced friction.

SUMMARY OF THE INVENTION

A copolymer has unit formula:

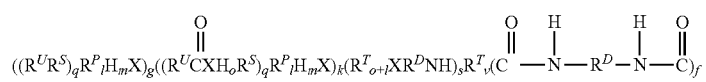

-continued

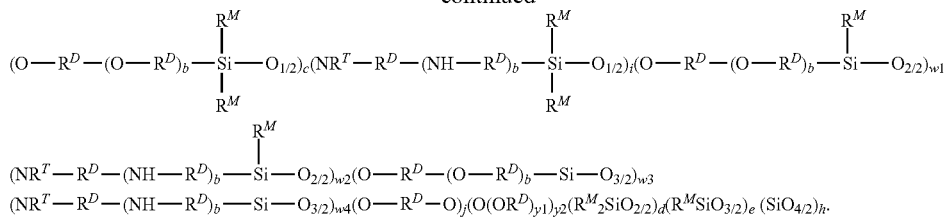

(SiO$_{4/2}$)$_h$. In this unit formula, each R$^U$ is independently a monovalent aliphatically unsaturated hydrocarbon group; each R$^D$ is independently a divalent hydrocarbon group or a divalent halogenated hydrocarbon group; each R$^S$ is a divalent spacer group selected such that together with R$^U$ and R$^P$, R$^S$ ensures that the unsaturated groups on different instances of R$^U$ at one end of the copolymer chain are separated by more than four chemical bonds; each R$^M$ is independently a monovalent hydrocarbon group or a monovalent halogenated hydrocarbon group; each R$^P$ is a divalent, trivalent, or tetravalent hydrocarbon group or a divalent, trivalent or tetravalent halogenated hydrocarbon group; each R$^T$ is hydrogen or a monovalent hydrocarbon group; each X is independently nitrogen, oxygen, or sulfur; each subscript b is independently greater than or equal to 0; subscript c is greater than or equal to 0; subscript d is greater than or equal to 0, subscript e is greater than or equal to 0; subscript h is greater than or equal to 0; subscript f is greater than or equal to 1; subscript g is greater than or equal to 0 and subscript k is greater than or equal to 0, with the proviso that a quantity (g+k) is greater than or equal to 1; subscript i is greater than or equal to 0; subscript j is greater than or equal to 0; subscript l is 0 or 1 when X is nitrogen and 1 when X is oxygen or sulfur; subscript m is 1 when X is nitrogen and subscript l is 1 and subscript m is 0 when X is oxygen or sulfur; subscript o is 1 when X is nitrogen and subscript o is 0 when X is oxygen or sulfur; subscript q is greater than 1 and less than or equal to 3; subscript s is greater than or equal to 0; subscript v is greater than or equal to 0; subscript w1 is greater than or equal to 0; subscript w2 is greater than or equal to 0; subscript w3 is greater than or equal to 0; subscript w4 is greater than or equal to 0; each subscript y1 is independently greater than 0; and subscript y2 is greater than 0.

The copolymer is useful in personal care compositions and health care compositions.

BRIEF DESCRIPTION OF THE DRAWINGS

FIG. 2A shows a perspective view of a wound dressing in the form of an adhesive bandage 200 including the skin contact adhesive 202 including the copolymer described herein.

Figure 1:
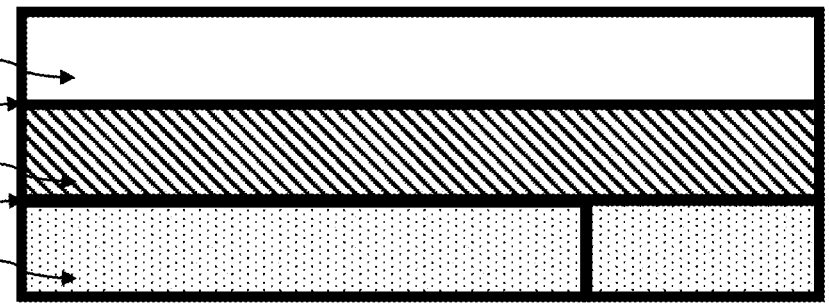
FIG. 1 is a partial cross section of a laminate article 100 including a skin contact adhesive including the copolymer described herein.

| Reference Numerals |
| --- |
| 100 laminate article |
| 101 support |
| 102 skin contact adhesive |
| 103 release liner |
| 104 skin facing surface |
| 105 skin contacting surface |
| 200 adhesive bandage |
| 201 absorbent layer |
| 202 skin contact adhesive |
| 203 skin facing surface |
| 204 support |
| 205 skin contact surface |
| 300 laminate article |
| 301 opposed surface of the carrier |
| 302 carrier |
| 303 opposed surface of the support |
| 304 support |
| 305 skin facing surface of the support |
| 306 absorbent layer |
| 307 opposed surface of the skin contact adhesive |
| 308 skin contact adhesive |
| 309 skin facing surface of the skin contact adhesive |
| 310 release liner |
| 400 flange |
| 401 support member |
| 402 skin contact adhesive |
| 403 aperture |

DETAILED DESCRIPTION OF THE INVENTION

The copolymer comprises units of formulae:

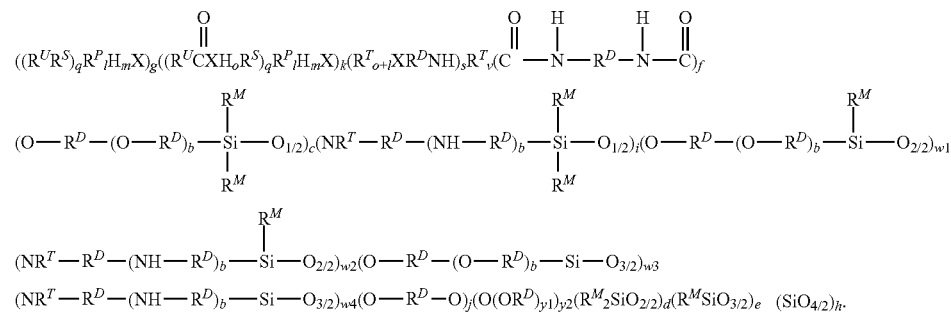

In the unit formula above, each $R^U$ is independently a monovalent aliphatically unsaturated hydrocarbon group. Each $R^U$ may have 1 to 13 carbon atoms. Each $R^U$ may be alkenyl or alkynyl, as defined below. Alternatively, each $R^U$ may be independently selected from alkenyl groups such as vinyl, allyl, butenyl, or hexenyl; alternatively vinyl or allyl.

Each $R^D$ is independently a divalent hydrocarbon group or a divalent halogenated hydrocarbon group, as defined below. Each $R^D$ may independently have 2 to 13 carbon atoms. Alternatively, each $R^D$ may be selected from alkylene such as ethylene or propylene, arylene such as phenylene, or alkaralkylene. Alternatively, each $R^D$ may be an alkylene group such as ethylene or propylene.

Each $R^S$ is a divalent spacer group which is independently a divalent hydrocarbon group, a divalent group containing two or more alkylene or arylene groups connected by oxygen, a divalent group containing two or more alkylene or arylene groups connected by a group of formula N-$R^M$, where $R^M$ is as defined below, a divalent group containing two or more alkylene or arylene groups connected by sulfur, a divalent group containing two or more alkylene or arylene groups connected by one or more ester groups, a divalent group containing two or more alkylene or arylene groups connected by one or more amide groups, a divalent group containing two or more alkylene or arylene groups connected by one or more carbonate groups, a divalent group containing two or more alkylene or arylene groups connected by one or more thioester groups, or a divalent group containing two or more alkylene or arylene groups connected by one or more ketone groups. The spacer group $R^S$, together with $R^U$ and $R^P$, ensures that the unsaturated groups on different $R^U$ groups on the same end of the polymer chain are separated by more than four chemical bonds. Alternatively, the unsaturated groups on the same end of the polymer chain may be separated by 5 to 500 chemical bonds, alternatively 5 to 300, alternatively 5 to 200, alternatively 5 to 100, alternatively 5 to 50, alternatively 6 to 25, and alternatively 6 to 15 chemical bonds.

Each $R^M$ is independently a monovalent hydrocarbon group as defined below or a monovalent halogenated hydrocarbon group as defined below. Each $R^M$ may have 1 to 13 carbon atoms. Alternatively, each $R^M$ may be a monovalent hydrocarbon group free of aliphatic unsaturation. For example, each $R^M$ may be independently selected from alkyl such as methyl, ethyl, propyl, butyl or hexyl; aryl such as phenyl, or aralkyl such as tolyl, xylyl or phenyl-methyl. Alternatively, each $R^M$ may be methyl or phenyl, and alternatively each $R^M$ may be methyl.

Each $R^P$ is a divalent, trivalent, or tetravalent hydrocarbon group or a divalent, trivalent or tetravalent halogenated hydrocarbon group. Each $R^P$ may be a divalent, trivalent, or tetravalent hydrocarbon group; alternatively each $R^P$ may be a divalent hydrocarbon group, as described above for each $R^D$.

Each $R^T$ is hydrogen or a monovalent hydrocarbon group. The monovalent hydrocarbon group for $R^T$ may have 1 to 13 carbon atoms. The monovalent hydrocarbon group for $R^T$ is group independently selected from alkyl such as methyl, ethyl, propyl, butyl, or hexyl; aryl such as phenyl; or aralkyl such as tolyl, xylyl, or phenyl-methyl. Alternatively, each $R^T$ may be methyl or phenyl. Alternatively each $R^T$ may be hydrogen or methyl.

Each subscript b is independently greater than or equal to 0. Alternatively, subscript b is 0 to 1,000,000. Alternatively, subscript b is 0 to 200,000. Alternatively, subscript b is 0 to 100,000. Alternatively, subscript b is 0 to 50,000. Alternatively, subscript b is 0 to 10,000. Alternatively, subscript b is 0 to 5,000. Alternatively, subscript b is 0 to 1,000. Alternatively, subscript b is 0 to 500. Alternatively, subscript b is 0 to 100. Alternatively, subscript b is 1 to 100. Alternatively, subscript b is 1 to 50. Alternatively, subscript b is 1 to 20. Alternatively, subscript b is 0 to 1. Alternatively, subscript b=0. Alternatively, subscript b=1. Alternatively, subscript b=2. Alternatively, subscript b=3. Alternatively, subscript b=4. Alternatively, subscript b=5.

Subscript c≥0. Alternatively, subscript c is 0 to 200,000. Alternatively, subscript c is 0 to 100,000. Alternatively, subscript c is 0 to 50,000. Alternatively, subscript c is 0 to 10,000. Alternatively, subscript c is 0 to 5,000. Alternatively, subscript c is 0 to 1,000. Alternatively, subscript c is 0 to 500. Alternatively, subscript c is 0 to 100. Alternatively, subscript c is 0 to 50. Alternatively, subscript c is 0 to 20. Alternatively, subscript c is 0 to 10. Alternatively, subscript c is 1 to 100. Alternatively, subscript c is 1 to 50. Alternatively, subscript c is 1 to 20. Alternatively, subscript c is 1 to 10.

Subscript i≥0. Alternatively, subscript i is 0 to 200,000. Alternatively, subscript i is 0 to 100,000. Alternatively, subscript i is 0 to 50,000. Alternatively, subscript i is 0 to 10,000. Alternatively, subscript i is 0 to 5,000. Alternatively, subscript i is 0 to 1,000. Alternatively, subscript i is 0 to 500. Alternatively, subscript i is 0 to 100. Alternatively, subscript i is 0 to 50. Alternatively, subscript i is 0 to 20. Alternatively, subscript i is 0 to 10. Alternatively, subscript i is 1 to 100. Alternatively, subscript i is 1 to 50. Alternatively, subscript i is 1 to 20. Alternatively, subscript i is 1 to 10.

Subscript w1≥0. Alternatively, subscript w1 is 0 to 200,000. Alternatively, subscript w1 is 0 to 50,000. Alternatively, subscript w1 is 0 to 10,000. Alternatively, subscript w1 is 0 to 5,000. Alternatively, subscript w1 is 0 to 1,000. Alternatively, subscript w1 is 0 to 500. Alternatively, subscript w1 is 0 to 100. Alternatively, subscript w1 is 0 to 50. Alternatively, subscript w1 is 0 to 20. Alternatively, subscript w1 is 0 to 10. Alternatively, subscript w1 is 1 to 100. Alternatively, subscript w1 is 1 to 50. Alternatively, subscript w1 is 1 to 20. Alternatively, subscript w1 is 1 to 10.

Subscript w2≥0. Alternatively, subscript w2 is 0 to 200,000. Alternatively, subscript w2 is 0 to 50,000. Alternatively, subscript w2 is 0 to 10,000. Alternatively, subscript w2 is 0 to 5,000. Alternatively, subscript w2 is 0 to 1,000. Alternatively, subscript w2 is 0 to 500. Alternatively, subscript w2 is 0 to 100. Alternatively, subscript w2 is 0 to 50. Alternatively, subscript w2 is 0 to 20. Alternatively, subscript w2 is 0 to 10. Alternatively, subscript w2 is 1 to 100. Alternatively, subscript w2 is 1 to 50. Alternatively, subscript w2 is 1 to 20. Alternatively, subscript w2 is 1 to 10.

Subscript w3≥0. Alternatively, subscript w3 is 0 to 200,000. Alternatively, subscript w3 is 0 to 50,000. Alternatively, subscript w3 is 0 to 10,000. Alternatively, subscript w3 is 0 to 5,000. Alternatively, subscript w3 is 0 to 1,000. Alternatively, subscript w3 is 0 to 500. Alternatively, subscript w3 is 0 to 100. Alternatively, subscript w3 is 0 to 50. Alternatively, subscript w3 is 0 to 20. Alternatively, subscript w3 is 0 to 10. Alternatively, subscript w3 is 1 to 100. Alternatively, subscript w3 is 1 to 50. Alternatively, subscript w3 is 1 to 20. Alternatively, subscript w3 is 1 to 10.

Subscript w4≥0. Alternatively, subscript w4 is 0 to 200,000. Alternatively, subscript w4 is 0 to 50,000. Alternatively, subscript w4 is 0 to 10,000. Alternatively, subscript w4 is 0 to 5,000. Alternatively, subscript w4 is 0 to 1,000. Alternatively, subscript w4 is 0 to 500. Alternatively, subscript w4 is 0 to 100. Alternatively, subscript w4 is 0 to 50. Alternatively, subscript w4 is 0 to 20. Alternatively, subscript w4 is 0 to 10. Alternatively, subscript w4 is 1 to 100. Alternatively, subscript w4 is 1 to 50. Alternatively, subscript w4 is 1 to 20. Alternatively, subscript w4 is 1 to 10.

A quantity $(c+i+w1+w2+w3+w4) \geq 1$. Alternatively, in one embodiment $i=w2=w4=0$, and a quantity $(c+w1+w3) \geq 1$, for example, when the copolymer is prepared using a carbinol functional polyorganosiloxane, as described below. In an alternative embodiment, $c=w1=w3=0$, and a quantity $(i+w2+w4) \geq 1$, for example, when the copolymer is prepared using an amine functional polyorganosiloxane, as described below.

Each X is independently nitrogen (N), oxygen (O), or sulfur (S). Alternatively, X is N or O. Alternatively, each X is N. Alternatively, each X is O.

Subscript $m=1$ when X is N, and subscript $l=1$. Subscript $m=0$ when X is O or S. When X is nitrogen, and subscript $l=0$; then subscript q is less than or equal to 2, and m is a quantity $(2-q)$.

Subscript l is 0 or 1 when X is N, and subscript $l=1$ when X is O or S.

Subscript $o=0$ when X is O or S, and subscript $o=1$ when X is N.

Subscript q indicates the number of aliphatically unsaturated hydrocarbon groups at a terminus of the polymer. In the formula above, $1 < q \leq 3$. Alternatively, $2 \leq q \leq 3$.

Subscripts d, e, and h depend on the molecular weight of one of the siloxane segments in the copolymer, and are without limit (only bound by the molecular weights reachable by the state of the art of siloxane synthesis chemistry), however subscript d may be 0 to 1,000,000; subscript e may be 0 to 1,000,000; subscript h may be 0 to 1,000,000, and a quantity $(d+e+h) \geq 1$. Subscript $d \geq 0$. Alternatively, subscript $d > 0$. Alternatively, subscript d is 0 to 200,000, and alternatively 0 to 100,000, alternatively 0 to 50,000, alternatively 0 to 10,000, alternatively 0 to 5,000, alternatively 0 to 1,000, alternatively 1 to 1,000, alternatively 1 to 500, and alternatively 1 to 200.

Subscript $e \geq 0$. Alternatively, subscript e is 0 to 1,000,000. Alternatively, subscript e is 0 to 200,000. Alternatively, subscript e is 0 to 100,000, alternatively 0 to 50,000, alternatively 0 to 10,000, alternatively 0 to 5,000, alternatively 0 to 1,000, alternatively 1 to 1,000, alternatively 1 to 500, and alternatively 1 to 200. Alternatively, subscript $e=0$.

Subscript f indicates the number of urethane units in the copolymer. Subscript f 1. Alternatively, subscript f is 1 to 1,500,000. Alternatively, subscript f is 1 to 500,000, alternatively 1 to 200,000, alternatively 1 to 50,000, alternatively 1 to 10,000, alternatively 1 to 5,000, alternatively 1 to 1,000, alternatively 1 to 500, and alternatively 1 to 200.

Subscript $g \geq 0$. Alternatively, subscript g is 0 to 500,000. Alternatively, subscript g is 0 to 200,000, alternatively 0 to 100,000, alternatively 0 to 50,000, alternatively 1 to 10,000, alternatively 1 to 5,000, alternatively 1 to 1,000, alternatively 1 to 500, and alternatively 1 to 200. Subscript $k \geq 0$. Alternatively, subscript k is 0 to 500,000. Alternatively, subscript k is 0 to 200,000, alternatively 0 to 100,000, alternatively 0 to 50,000, alternatively 1 to 10,000, alternatively 1 to 5,000, alternatively 1 to 1,000, alternatively 1 to 500, and alternatively 1 to 200. A quantity $(g+k) \geq 1$. Alternatively, $1 \leq (g+k) \leq 1,000,000$. Alternatively $1 \leq (g+k) \leq 500,000$, alternatively $1 \leq (g+k) \leq 50,000$, alternatively $1 \leq (g+k) \leq 10,000$, alternatively $1 \leq (g+k) \leq 5,000$, alternatively $1 \leq (g+k) \leq 500$, alternatively $1 \leq (g+k) \leq 100$.

Subscript h is $\geq 0$. Alternatively, subscript h is 0 to 1,000,000. Alternatively, subscript h is 0 to 200,000, alternatively 0 to 100,000, alternatively 0 to 50,000, alternatively 0 to 10,000, alternatively 0 to 5,000, alternatively 0 to 1,000, alternatively 1 to 1,000, alternatively 1 to 500, and alternatively 1 to 200. Alternatively, subscript $h=0$.

Subscript j is $\geq 0$. Alternatively, subscript j is 0 to 500,000. Alternatively, subscript j is 0 to 200,000, alternatively 0 to 100,000, alternatively 0 to 50,000, alternatively 1 to 10,000, alternatively 1 to 5,000, alternatively 1 to 1,000, alternatively 1 to 500, and alternatively 1 to 200. Subscript j is $>0$ when a chain extender is used in making the copolymer.

Subscript s is $\geq 0$. Alternatively, subscript s is 0 to 200,000. Alternatively, subscript s is 0 to 150,000, alternatively 0 to 100,000, alternatively 0 to 50,000, alternatively 1 to 10,000, alternatively 1 to 5,000, alternatively 1 to 1,000, alternatively 1 to 500, and alternatively 1 to 200.

Subscript v is $\geq 0$. Alternatively, subscript v is 0 to 200,000. Alternatively, subscript v is 0 to 150,000, alternatively 0 to 100,000, alternatively 0 to 50,000, alternatively 1 to 10,000, alternatively 1 to 5,000, alternatively 1 to 1,000, alternatively 1 to 500, and alternatively 1 to 200.

Each subscript y1 is independently greater than 0. Alternatively, subscript y1 is 1 to 1,000,000. Alternatively, subscript y1 is 1 to 200,000. Alternatively, subscript y1 is 1 to 100,000. Alternatively, subscript y1 is 1 to 50,000. Alternatively, subscript y1 is 1 to 10,000. Alternatively, subscript y1 is 1 to 5,000. Alternatively, subscript y1 is 1 to 1,000. Alternatively, subscript y1 is 1 to 500. Alternatively, subscript y1 is 1 to 100. Alternatively, subscript y1 is 1 to 100. Alternatively, subscript y1 is 1 to 50. Alternatively, subscript y1 is 1 to 20. Alternatively, subscript $y1=1$. Alternatively, subscript $y1=2$. Alternatively, subscript $y1=3$. Alternatively, subscript $y1=4$. Alternatively, subscript $y1=5$.

Subscript y2 is greater than 0. Alternatively, subscript y2 is 1 to 500,000. Alternatively, subscript y2 is 1 to 200,000, alternatively 1 to 100,000, alternatively 1 to 50,000, alternatively 1 to 10,000, alternatively 1 to 5,000, alternatively 1 to 1,000, alternatively 1 to 500, and alternatively 1 to 200.

Alternatively, when subscripts $m=k=s=v=i=w1=w2=w3=w4=e=h=0$, the copolymer may have formula (I):

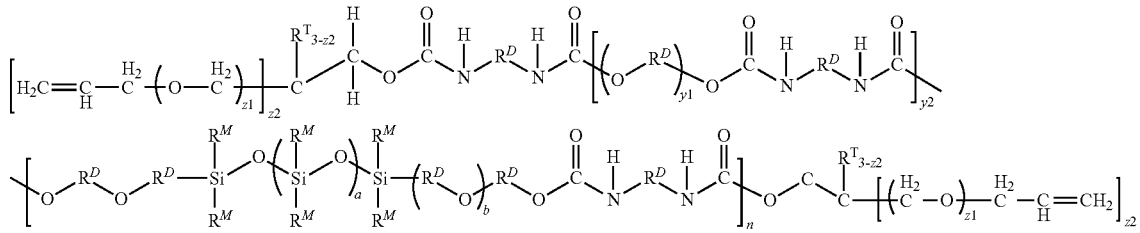

where $R^U$, $R^D$, and $R^M$ are as described above, each subscript a is independently 0 to 1,000,000, and each subscript b is independently greater than or equal to 0, and subscript n is greater than or equal to 1. Alternatively, subscript a is 0 to 200,000, alternatively 0 to 100,000, alternatively 0 to 50,000, alternatively 0 to 10,000, alternatively 0 to 5,000, alternatively 0 to 1,000, alternatively 1 to 1,000, alternatively 1 to 500, alternatively 1 to 200, and alternatively 5 to 150. Each subscript b 0. Alternatively, subscript b is 0 to 1,000,000. Alternatively, subscript b is 0 to 200,000. Alternatively, subscript b is 0 to 100,000. Alternatively, subscript b is 0 to 50,000. Alternatively, subscript b is 0 to 10,000. Alternatively, subscript b is 0 to 5,000. Alternatively, subscript b is 0 to 1,000. Alternatively, subscript b is 0 to 500. Alternatively, subscript b is 0 to 100. Alternatively, subscript b is 1 to 100. Alternatively, subscript b is 1 to 50. Alternatively, subscript b is 1 to 20. Alternatively, subscript b is 0 to 1. Alternatively, subscript b=0. Alternatively, subscript b=1. Alternatively, subscript b=2. Alternatively, subscript b=3. Alternatively, subscript b=4. Alternatively, subscript b=5. Subscript n is 1 to 1,500,000. Alternatively, subscript n is 1 to 500,000, alternatively 1 to 200,000, alternatively 1 to 50,000, alternatively 1 to 10,000, alternatively 1 to 5,000, alternatively 1 to 1,000, alternatively 1 to 500, and alternatively 1 to 200. Subscript Z2 is greater than 1 and less than or equal to 3. Subscript Z1 is 1 to 15, alternatively 1 to 10, alternatively 1 to 5, and alternatively from 1 to 3.

Method for Making the Copolymer

The copolymer described above may be prepared by a method comprising:
i) combining starting materials comprising
  a) an isocyanate compound,
  b) an endblocker,
  c) a catalyst,
  d) a polyorganosiloxane, and
  e) a polymeric organic diol; thereby preparing the copolymer. Starting material f) a solvent may be added. The starting materials may be combined in any order.

Alternatively, the copolymer described above may be prepared by a method comprising:
i) combining starting materials comprising:
  a) an isocyanate compound, and
  b) an endblocker; thereby preparing a precursor, and
ii) combining the precursor prepared in step i) with a starting material comprising
  c) a catalyst,
  d) a polyorganosiloxane, and
  e) a polymeric organic diol; thereby preparing the copolymer. Starting material f) a solvent may be added during step ii).

Alternatively, the copolymer described above may be prepared by a method comprising:
i) combining starting materials comprising
  a) an isocyanate compound,
  b) an endblocker, and
  c) a catalyst, thereby preparing a precursor, and
ii) combining the precursor prepared in step i) with a starting material comprising
  d) a polyorganosiloxane, and
  e) a polymeric organic diol; thereby preparing the copolymer. Starting material f) a solvent may be added during step ii).

Alternatively, the copolymer described above may be prepared by a method comprising:
i) combining starting materials comprising
  a) an isocyanate compound,
  e) a polymeric organic diol, and
  c) a catalyst, thereby preparing a precursor, and
  d) a polyorganosiloxane; and ii) combining the precursor prepared in step i) with a starting material comprising
  b) an endblocker; thereby preparing the copolymer. Starting material f) a solvent may be added during step ii).

In each embodiment of the method described above, d) the polyorganosiloxane may be d1) a carbinol functional polyorganosiloxane, d2) an amine functional polyorganosiloxane, or a mixture of both d1) and d2).

In one embodiment, d) the polyorganosiloxane may be pre-reacted with a) the isocyanate before reacting e) the polymeric organic diol in the method. Alternatively, a) the isocyanate compound may be pre-reacted with e) the polymeric organic diol before reacting the d) polysiloxane diol in the method.

Starting Material a) Isocyanate Compound

The isocyanate compound has an average of one or more isocyanate groups per molecule. Alternatively, the isocyanate compound may have an average of two or more isocyanate groups per molecule. The isocyanate compound may have formula: $R-(N=C=O)_p$, where R is a hydrocarbon group or a halogenated hydrocarbon group and subscript p is an integer representing the number of isocyanate groups per molecule. Subscript p is greater than or equal to 1. Alternatively, subscript p is 2, 3, or 4; alternatively subscript p is 2 or 3; and alternatively, subscript p is 2. R is a divalent hydrocarbon group when subscript p is 2. R is a trivalent hydrocarbon group when subscript p is 3. R is a tetravalent hydrocarbon group when subscript p is 4.

The isocyanate compound is exemplified by monomeric isocyanates and polymeric isocyanates. Monomeric isocyanates include aromatic diisocyanates such as, meta-tetramethyl xylene diisocyanate (TMXDI), toluene diisocyanate (TDI), phenylene diisocyanate, xylene diisocyanate, 1,5-naphthalene diisocyanate, chlorophenylene 2,4-diisocyanate, bitoluene diisocyanate, dianisidine diisocyanate, toluidine diisocyanate and alkylated benzene diisocyanates; aliphatic and cycloaliphatic isocyanates such as hexamethylene diisocyanate (HDI), hydrogenated methylene diphenyl diisocyanate (HMDI), 1-isocyanato-3-isocyanatomethyl-3,5,5-trimethyl-cyclohexane (isophorone diisocyanate, IPDI), and nonanetriisocyanate (TTI), methylene-interrupted aromatic diisocyanates such as methylene-diphenyl-diisocyanate, especially the 4,4'-isomer (MDI) including alkylated analogs such as 3,3'-dimethyl-4,4'-diphenyl-methane diisocyanate; hydrogenated materials such as cyclohexylene diisocyanate, 4,4'-methylenedicyclohexyl diisocyanate; mixed aralkyl diisocyanates such as the tetramethylxylyl diisocyanates, 1,4-bis(1-isocyanato-1,1'-dimethylmethyl) benzene $OCNC(CH_3)_2C_6H_4C(CH_3)_2NCO$, and polymethylene isocyanates such as 1,4-tetramethylene diisocyanate, 1,5-pentamethylene diisocyanate, 1,6-hexamethylene diisocyanate (HDI), 1,7-heptamethylene diisocyanate, 2,2,4- and 2,4,4-trimethylhexamethylene diisocyanate, 1,10-decamethylene diisocyanate, and 2-methyl-1,5-pentamethylene diisocyanate; vinylisocyanate; and combinations thereof.

Polymeric isocyanates include dimerized isocyanates uretdiones or uretidinediones and carbodiimide, trimerized isocyanates isocyanurates, iminooxadiazine dione, uretonimine, and linear polymer α-Nylon; and derivatized isocyanates by reacting difunctional or multifunctional isocyanates with various compounds to form allophanate, or biuret compounds, or isocyanate functional urethane or other prepolymers. Some of the polyisocyanates are difunctional, i.e., having 2 isocyanate groups per molecule. Some have more than two isocyanate groups. An example is polymeric diphenylmethane diisocyanate, which is a mixture of molecules with two-, three-, and four- or more isocyanate groups, which may have an average functionality greater than two, commonly 2.7. Isocyanate functional compounds with isocyanate functionality greater than two may act as crosslinking sites. Commercially available isocyanate functional organic compounds are illustrated by Tolonate XIDT 70SB, an isophorone diisocyanate trimer (70% solids, 12.3 wt % NCO) sold by Rhodia (Cranbury, N.J.) and Desmodur N-100 polyisocyanate (available from Mobay Corp.).

Alternatively, a) the isocyanate compound may comprise a blocked isocyanate. The isocyanate group can be blocked by common blocking agents such as phenol, nonyl phenol, butanone oxime, caprolactam, and others. These blocked isocyanates can be released by any conventional means such as heating at a temperature above room temperature to react with chain extenders and polyorganosiloxanes to construct the copolymer.

Starting Material b) Endblocker

The endblocker is a compound having an average of more than one aliphatically unsaturated group per molecule, and the endblocker may be selected from an amine compound, an alcohol, or a thiol compound. The endblocker may be selected from compounds of formulae:

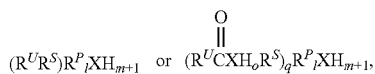

where $R^U$, $R^P$, $R^S$, and X and subscripts q, l, m, and o are as described above. The endblocker is added in an amount sufficient to provide a molar ratio of XH groups on the endblocker to isocyanate groups (XH/N=C=O)<1.

Alternatively, the endblocker may be an amine compound. The amine compound may have formula $(R^U R^S)_2 NH$, where $R^U$ and $R^S$ are as described above, Examples of suitable amine compounds for the endblocker include dihexenyl amine.

Alternatively, the endblocker may be an alcohol compound. The alcohol compound may may have formula $(R^U R^S)_{z3} R^P OH$, where $R^U$, $R^P$, and $R^S$ are as described above, and subscript $z3 \geq 0$. Alternatively subscript z3 is 0 to 3. Alternatively, subscript z=2. Examples of suitable alcohol compounds for the endblocker include trimethylolpropane diallylether, and pentaerythritol triallylether.

Starting Material c) Catalyst

Reacting the polyorganosiloxane with the precursor in one of the methods described above may be catalyzed by starting material c) a catalyst. Suitable catalysts include tertiary amines and metal salts, such as the salts of tin. Tin compounds are useful as catalysts herein include those where the oxidation state of the tin is either +4 or +2, i.e., tin (IV) compounds or tin (II) compounds. Examples of tin (IV) compounds include stannic salts such as dibutyl tin dilaurate, dimethyl tin dilaurate, di-(n-butyl)tin bis-ketonate, dibutyl tin diacetate, dibutyl tin maleate, dibutyl tin diacetylacetonate, dibutyl tin dimethoxide, carbomethoxyphenyl tin tris-uberate, dibutyl tin dioctanoate, dibutyl tin diformate, isobutyl tin triceroate, dimethyl tin dibutyrate, dimethyl tin di-neodecanoate, dibutyl tin di-neodecanoate, triethyl tin tartrate, dibutyl tin dibenzoate, butyltintri-2-ethylhexanoate, dioctyl tin diacetate, tin octylate, tin oleate, tin butyrate, tin naphthenate, dimethyl tin dichloride, a combination thereof, and/or a partial hydrolysis product thereof. Tin (IV) compounds are known in the art and are commercially available, such as Metatin® 740 and Fascat® 4202 from Acima Specialty Chemicals of Switzerland, Europe, which is a business unit of The Dow Chemical Company. Examples of tin (II) compounds include tin (II) salts of organic carboxylic acids such as tin (II) diacetate, tin (II) dioctanoate, tin (II) diethylhexanoate, tin (II) dilaurate, stannous salts of carboxylic acids such as stannous octoate, stannous oleate, stannous acetate, stannous laurate, stannous stearate, stannous naphthanate, stannous hexanoate, stannous succinate, stannous caprylate, and a combination thereof. Other metal salts are also suitable catalysts for this reaction. Examples include zinc salts such as zinc acetate and zinc naphthenate. Salts of lead, bismuth, cobalt, iron, antimony, sodium, such as lead octoate, bismuth nitrate, and sodium acetate can also catalyze this reaction. In certain occasions organomercuric compounds can also be used.

Optionally co-catalysts can also be used along with a primary catalyst. And a combination of two or more catalysts can be used, e.g., to provide either faster reaction than achievable with a single catalyst, or a better balanced reaction initiation time and finish time.

Starting Material d1) Carbinol-Functional Polyorganosiloxane

The carbinol-functional polyorganosiloxane used to prepare the copolymer described above comprises units of formulae:

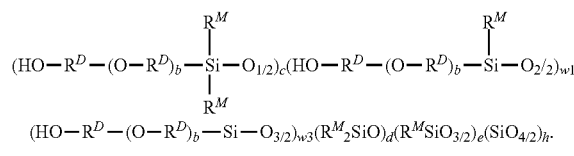

In this unit formula, each $R^M$, $R^D$, subscript b, subscript c, subscript w1, subscript w3, subscript d, subscript e, and subscript h are as described above. The carbinol groups, e.g., hydroxyalkyl groups, can be terminal or pendent on the polyorganosiloxanes, or at both terminal and pendent positions. Alternatively, the carbinol groups may be at terminal positions on the polyorganosiloxane. Examples of carbinol-terminated polyorganosiloxanes are disclosed in WO2008/088491, U.S. Pat. No. 6,528,121, and U.S. Pat. No. 7,452,956. The carbinol-groups may be at terminal positions, pendent positions, or both terminal and pendent positions in the carbinol-functional polyorganosiloxane. Alternatively, the carbinol groups may be at terminal positions.

Alternatively, d1) the carbinol-functional polyorganosiloxane may comprise an α,ω-difunctional polydiorganosiloxane of formula (III): $R^C R^M_2 Si-R^{DX}-(R^M_2 SiO)_r-R^{DX}-SiR^M_2 R^C$, where, each $R^C$ is independently a carbinol functional group of formula $HO-R^D-(OR^D)_b-$ where subscript b, $R^M$ and $R^D$ are as described above, each $R^{DX}$ is independently selected from O or a divalent hydrocarbon group described above as $R^D$, and subscript r represents the degree of polymerization of the carbinol-terminated polyorganosiloxane of formula (III). Subscript r>0. Alternatively, subscript r may be 1 to 1,000,000, alternatively 50 to 1,000, and alternatively 200 to 700. Alternatively, subscript r is 0 to 200,000, alternatively 0 to 200,000, alternatively 0 to 100,000, alternatively 0 to 50,000, alternatively 0 to 10,000, alternatively 0 to 5,000, alternatively 0 to 1,000, alternatively 1 to 1,000, alternatively 1 to 500, alternatively 1 to 200, and alternatively 5 to 150. Alternatively, each $R^{DX}$ is O.

Starting Material d2) Amine-Functional Polyorganosiloxane

The amine functional polyorganosiloxane comprises units of formulae:

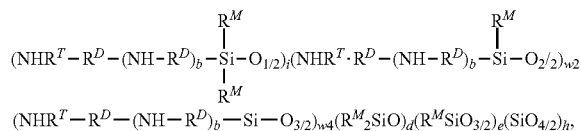

where $R^D$, $R^M$, $R^T$, and subscripts b, d, e, h, and i are as described above. The amine functional groups can be terminal or pendent, or both terminal and pendent.

An exemplary amine terminated polyorganosiloxane comprises a terminal unit of formula

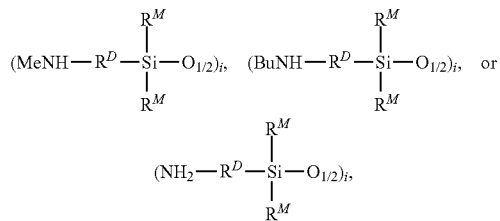

where Me represents a methyl group and Bu represents a butyl group; and further comprises one or more of $(R^M{}_2SiO_{2/2})_d(R^MSiO_{3/2})_e(SiO_{4/2})_h$, where RM, $R^D$, and subscripts l, d, e, and h are as described above.

Starting Material e) Polymeric Organic Diol

A polymeric organic diol may optionally be added during one or more of the method described above. Suitable polymeric organic diols include polyalkylene oxide diols such as polyethylene oxide diols, polypropylene oxide diols, polyethylene oxide/ polypropylene oxide diols, and polybutylene oxide diols; polyester diols, polycarbonate oxide diols, or copolymer diols of these polymers. The organic diol may be added to tune the surface energy and/or hydrophilicity of the copolymer. The amount added may be greater than 0 to 75%, alternatively greater than 0 to 50%, alternatively 1 to 25%.

Starting Material f) Optional Solvent

A solvent may be added during the method to prepare the copolymer described herein. Any organic compound that will dissolve the copolymer and that is relatively unreactive towards isocyanate, and amine and/or carbinol compounds is suitable as a solvent. Examples include aliphatic hydrocarbons, aromatic hydrocarbons, esters, ethers, ketones, and amides. Exemplary solvents include ethyl acetate, butyl acetate, methyl ethyl ketone, or tetrahydrofuran.

The amount of solvent to be used is dependent on the properties of the copolymer including structure, molecular weight, and the particular method of copolymer preparation, and can be 0 to 99%. Generally for higher molecular weight copolymers especially when a high torque mixing mechanism will not be used, solvent may be added to reduce the viscosity and make the system easier to handle during performance of the method to make the copolymer. If the molecular weight is relatively low and/or high torque mixing equipment such as a twin screw extruder is used, no solvent needs to be used. When solvent is used, the amount may be 0 to 99%, alternatively 0 to 80%, alternatively 1% to 60%, and alternatively 5% to 50%, based on the combined weights of all starting materials used.

Starting Material g) Optional Additional Endblocker.

After the reaction step ii) as described above, optionally the reaction product can be treated with an additional end blocker, which is distinct from the endblocker described above as starting material d). This additional end blocker, g), can be such that it leaves an additional reactive group on the copolymer after end blocking reaction, or it leaves an unreactive group on the copolymer after the end blocking reaction. Suitable such end blockers for starting material g) include but are not limited to alcohols such ethanol, propanol, butanol, carboxylic acids such as acetic acids, and alcohols and carboxylic acids containing aliphatic unsaturation. Thio-alcohols, hydroxylamines, glycol, amino acids, and amino sugars are also suitable as additional endblocking agents. When isocyanate is present in molar excess during preparation of the copolymer, unreacted isocyanate can be present in the copolymer. Starting material g), the additional endblocker may be added to react with this residual isocyanate.

The molar ratio among the reactants, i.e. isocyanate compound, polyorganosiloxane, endlocker, and polymeric organic diol, can vary widely, according to the polyorganosiloxane structure and molecular weight desired, to arrive at the copolymer described by the unit formulae herein. The molar ratio of isocyanate groups of starting material a) to the active hydrogen of carbinol or amine groups on the polysiloxane selected for starting material d) can be 0.1 to 100, alternatively 0.1 to 50, alternatively 0.1 to 10, alternatively 0.1 to 2, alternatively 0.1 to 1.5, alternatively 0.1 to 1.25, alternatively 0.1 to 1.1, alternatively 0.1 to 1.05, alternatively 0.1 to 1.01, alternatively 0.1 to 1, alternatively 0.1 to 0.9, alternatively 0.1 to 0.5, alternatively 0.5 to 50, alternatively 0.5 to 10, alternatively 0.5 to 2, alternatively 0.5 to 1.5, alternatively 0.5 to 1.25, alternatively 0.5 to 1.1, alternatively 0.5 to 1.05, alternatively 0.5 to 1.01, alternatively 0.5 to 1, alternatively 0.5 to 0.9, and alternatively 0.4 to 0.7. When this ratio is <1, the reaction is controlled so that the endblocker is added before all the isocyanate groups are consumed. When this ratio is >1, the endblocker can be added before or after all the active hydrogen on the carbinol or amine groups have been reacted. The molar ratio between the endblocker to the isocyanate can be from 0.001 to 0.99, alternatively 0.001 to 0.8, alternatively 0.01 to 0.8, alternatively 0.01 to 0.6, alternatively 0.01 to 0.5, alternatively 0.01 to 0.4, alternatively 0.01 to 0.3, alternatively 0.01 to 0.2, alternatively 0.01 to 0.1, alternatively 0.05 to 0.8, alternatively 0.05 to 0.6, alternatively 0.05 to 0.5, alternatively 0.05 to 0.4, alternatively 0.05 to 0.3, alternatively 0.05 to 0.2, alternatively 0.05 to 0.1. The molar ratio between the isocyanate groups to the active hydrogen on the hydroxyl or amine groups or other reactive groups on the polyorganosiloxane (or the combination of the polyorganosiloxane and the chain extender, when present) can be >1 to 1,000,000, alternatively 1.001 to 500,000, alternatively 1.001 to 200,000, alternatively 1.001 to 100,000, alternatively 1.001 to 50,000, alternatively 1.001 to 10,000, alternatively 1.001 to 5,000, alternatively 1.001 to 1,000, alternatively 1.001 to 500, alternatively 1.001 to 100, alternatively 1.001 to 50, alternatively 1.001 to 20, alternatively 1.001 to 10, alternatively 1.001 to 5, alternatively 1.001 to 4, alternatively 1.001 to 3, alternatively 1.001 to 2, alternatively 1.001 to 1.5, alternatively 1.001 to 1.3, alternatively 1.001 to 1.2, alternatively 1.01 to 20, alternatively 1.01 to 10, alternatively 1.01 to 5, alternatively 1.01 to 4, alternatively 1.01 to 3, alternatively 1.01 to 2, alternatively 1.01 to 1.5, alternatively 1.01 to 1.3, and alternatively 1.01 to 1.2.

Starting Material h) Chain Extender

The chain extender is a dialcohol, of formula HO-$R^D$-OH, where $R^D$ is as defined above. Suitable dialcohols include 1,3-butanediol; 1,4-butanediol; 1,6-hexanediol, 1,10-decanediol; 1,6-hexamethylenediol; 2,2-dimethyl-1,3-propanediol; 1,4-cyclohexanedimethylol; 1,1'-isopropylidine-bis-(p-phenylene-oxy)-di-2-ethanol; poly(tetrmethylene ether) glycol; and ethylene glycol. Alternatively, the chain extender comprises ethylene glycol. Alternatively, the chain extender may be a diamine containing 2 to 20 carbon atoms e.g., 1,2-diaminoethane; 1,4-diaminobutane; 1,2-propanediamine; hexamethylenediamine; diethylene diamine; 5-amino-1-(aminomethyl)-1,3,3-trimethylcyclohexane; 4,4'-methylene bis(cyclohexylamine); and ethanol amine. Alternatively, the chain extender may be a dithiol, a dicarboxylic acid, or a diepoxide. Suitable chain extenders are disclosed, for example, in U.S. Pat. Nos. 4,840,796 and 5,756,572.

Method Conditions

Steps i) and ii) in each embodiment of the method described above may be performed with or without heating. The temperature for the reaction depends on the selection of starting materials a), b), c), d), and e), and whether any of f), g), and/or h) is present, however, the temperature may range from -20° C. to 150° C.; alternatively 0° C. to 100° C., and alternatively 20° C. to 60° C. at pressure of 1 atmosphere. Pressure under which the method is performed is not critical.

Each embodiment of the method described above may be performed in batch, semi-batch, semi-continuous, or continuous mode in any convenient equipment. When preparing higher molecular weight copolymers (e.g., when higher molecular weight starting materials are used), the method may be performed in an extruder, such as a twin screw extruder.

Crosslinking the Copolymer

The copolymer described above can be crosslinked, by any means that will initiate the reaction of the aliphatic unsaturation. The reaction can be initiated by thermally generated free radicals. It is also ultraviolet radiation crosslinkable via several different means. The aliphatic unsaturation can react with themselves, or additional reactive compounds (crosslinkers) can be added to react with the unsaturation. Suitable crosslinkers include but are not limited to other carbon-carbon unsaturation containing compounds such as acrylates and methacrylates, divinyl and diallyl compounds, and others such as thiols (SH containing), phosphines (PH containing), boranes (BH containing), and silanes (SiH containing). In a first embodiment, a crosslinkable composition comprises: (A) the copolymer described above, and (B) a curing catalyst. The (B) curing catalyst can be (B1) a free radical initiator, or (B2) a hydrosilylation catalyst, depending on the crosslinker being used. The free radical initiator can be a peroxide which can be thermally activated or activated by a reducing agent at room temperature. The peroxide may have formula $R^{MS}$-O—O-$R^{MS}$, where each $R^{MS}$ is independently a saturated monovalent hydrocarbon group or saturated monovalent halogenated hydrocarbon group, such as alkyl as defined below. Examples of peroxides include di-tert-butyl peroxide, bis(tert-butylperoxy)hexane, dicumyl peroxide, and bis (tert-butylperoxyisopropyl)benzene, 1,1-bis(tert-butyl peroxy)-3,3,3-trimethylcyclohexane, 2,5-dimethyl-2,5-di(tert-butylperoxy)hexane, 2,5-dimethyl-2,5-bis(tert-butylperoxy) hexyne-3, (tert-butylperoxy)myristylcarbonate; and mixtures of two or more thereof. Alternatively, the free radical initiator can also be a photo-activated compound. Photo-activated initiators are well known in the literature and any known initiating systems can be used. These can be one component systems or two component systems. One component systems include benzoyl-chromophore based ones, substituted benzoyl-chromophore based ones, hydroxyl alkyl heterocyclic ketones, hydroxyl alkyl conjugated ketones, benzophenone- and thioxanthone-moiety-based systems, benzoyl phosphine oxide derivatives, phosphine oxide derivatives, trichloromethyl triazines, biradical generating ketones, some peroxides and diketones, azides and aromatic bis-azides, some azo, disulfide, disilane, diselenide, diphenylditelluride, digermane, and distanane derivatives, compounds with carbon-germanium, carbon-silicon, carbon-sulfur, sulfur-silicon, sulfur-sulfur, and germanium-silicon cleavable bonds, and others. Two component systems include ketone-hydrogen donor based systems, dye-based system, and various others. Examples of such free radical initiators are known in the art and are commercially available, such as 2-hydroxy-2-methyl-1-phenyl-propan-1-one (commercially available as Darocur 1173). Other commercially available examples include 1-hydroxy-cyclohexyl- phenyl-ketone, benzophenone, 2-hydroxy-1-[4-(2-hydroxyethoxy) phenyl]-2-methyl-1-propanone, methylbenzoylformate, oxy-phenyl-acetic acid 2-[2 oxo-2 phenyl-acetoxy-ethoxy]-ethyl ester, oxy-phenyl-acetic 2-[2-hydroxy-ethoxy]-ethyl ester, alpha-dimethoxy-alpha-phenylacetophenone, 2-benzyl-2-(dimethylamino)-1-[4-(4-morpholinyl) phenyl]-1-butanone, 2-methyl-1-[4-(methylthio) phenyl]-2-(4-morpholinyl)-1-propanone, diphenyl (2,4,6-trimethylbenzoyl) phosphine oxide, phenyl bis (2,4,6-trimethyl benzoyl) phosphine oxide, or bis (eta 5-2,4-cyclopentadien-1-yl), or bis [2,6-difluoro-3-(1H-pyrrol-1-yl) phenyl]titanium. The amount of free radical initiator added to this crosslinkable composition depends on various factors including the other ingredients of the composition, however, the amount may range from 0.01% to 10% based on the weight of the composition. Alternatively the amount is 0.01% to 5%, alternatively 0.05% to 5%, alternatively 0.05% to 3%, alternatively 0.1% to 10%, alternatively 0.1% to 5%, alternatively 0.1% to 3%, The composition may be crosslinked by exposure to ultra violet radiation, visible light, or infrared radiation, depending on where sufficient absorption occurs and how the absorbed energy is transferred to activated the initiator and produce free radicals. Alternatively the initiators can be activated by heat or the activation is assisted by heat in combination with electromagnetic radiation. When crosslinking is activated by heat, additionally many other heat activated free radical initiators can be used. Examples include peroxides and azo compounds. Exemplary peroxides are known in the art, for example, those recited in U.S. Pat. Nos. 4,929,669; 5,082,886; 5,258,211; and 5,919,884. The copolymers can be crosslinked by themselves without additional crosslinkers, or a crosslinker/mixture of crosslinkers can be added to crosslink the copolymers.

Crosslinking may be performed by any convenient means, such as exposing the crosslinkable composition to heat and/or radiation such as electron beam or ultra violet (UV) radiation. When heat is used to crosslink the crosslinkable composition, a temperature from 25 to 200° C. can be used for a duration of less than five seconds to two hours. When electron beam is used to crosslink the crosslinkable composition, an accelerating voltage of 75 kV to 350 kV can be used and a dosage of 5 to 250 kilogray (kGy) is usually sufficient to crosslink the composition. When UV is used, a light source of 200 nm to 450 nm is suitable, and can be generated by a mercury vapor lamp (Type H, D, or V for different wavelengths), a fluorescent lamp, or an UV LED lamp. The power rating of the lamp needed depends on the composition and can be any emitting irradiation at a dosage of at least 0.001 mJ/cm$^2$, alternatively from 0.01 to 2000 mJ/cm$^2$, alternatively from 0.1 to 1000 mJ/cm$^2$, alternatively from 1 to 1000 mJ/cm$^2$, alternatively from 10 to 500 mJ/cm$^2$.

The copolymers can also be crosslinked by reacting the aliphatic unsaturation with a compound with silicon hydride groups through a hydrosilylation reaction. This reaction is usually catalyzed by metal salts and other compounds, amines and other organic bases, peroxides, and/or complexes, and organic peroxides can be used to catalyze hydrosilylation. Hydrosilylation catalysts are known in the art and are commercially available. Such conventional hydrosilylation catalysts can be a metal selected from platinum, rhodium, ruthenium, palladium, osmium, and iridium. Alternatively, the hydrosilylation catalyst may be a compound of such a metal, for example, chloroplatinic acid, chloroplatinic acid hexahydrate, platinum dichloride, and complexes of said compounds with low molecular weight organopolysiloxanes or platinum compounds microencapsulated in a matrix or core/shell type structure. Complexes of platinum with low molecular weight organopolysiloxanes include 1,3-diethenyl-1,1,3,3 -tetramethyldisiloxane complexes with platinum. These complexes may be microencapsulated in a resin matrix. Exemplary hydrosilylation catalysts are described in U.S. Pat. Nos. 3,159,601; 3,220, 972; 3,296,291; 3,419,593; 3,516,946; 3,814,730; 3,989, 668; 4,784,879; 5,036,117; and 5,175,325 and EP 0 347 895 B. Microencapsulated hydrosilylation catalysts and methods of preparing them are known in the art, as exemplified in U.S. Pat. Nos. 4,766,176 and 5,017,654.

The crosslinkable composition may optionally further comprise (C) a crosslinker in addition to starting materials (A) and (B), described above. The crosslinker may be (C1) an acrylate crosslinker, (C2) a crosslinker containing alkenyl groups (other than in an acrylate group), (C3) a thiol functional crosslinker, or (C4) an SiH containing crosslinker. The acrylate crosslinker and the crosslinker containing other alkenyl groups can contain one or more acrylate or alkenyl (e.g., vinyl) groups per molecule. Examples include but are not limited to methylmethacrylate, n-butyl acrylate, 2-ethyl hexyl methacrylate, ethylene glycol diacrylate, poly(ethylene glycol) diacrylate, neopentyl glycol diacrylate, trimethylolpropane triacrylate, pentaerythritol triacrylate, glycerol propoxylate triacrylate, trimethylolpropane propoxylate triacrylate, trimethylolpropane ethoxylate triacrylate, pentaerythritol tetraacrylate, di(trimethylolpropane) tetraacrylate, divinylbenzene, divinyl sulfone, 1,4-butanediol divinyl ether, ethylene glycol divinyl ether, di- tri-, and poly-ethylene glycol divinyl ether, and styrene.

Suitable thiol functional crosslinkers (C3) are known in the art and are commercially available. They can be organic thiol compounds (SH containing compounds) with an average of two or more SH groups per molecule, or mercaptofunctional silanes, siloxanes, polysilanes, polysiloxanes, organosilanes, organosiloxanes, and organopolysiloxanes containing an average of two or more SH groups per molecule. Suitable thiol-ene crosslinkers include: a trimethylsiloxy terminated dimethylsiloxane- methylmercaptopropylsiloxane copolymer with a SH content of 0.35 mol/100 g; a trimethylsiloxy terminated dimethylsiloxane-methylmercaptopropylsiloxane copolymer with a SH content of 0.16 mol/100 g, purchased from Gelest, Inc.; a trimethylsiloxy terminated dimethylsiloxane-methylmercaptopropylsiloxane copolymer with a SH content of 0.05 mol/100 g, purchased from Gelest, Inc.; and a trimethylsiloxy terminated dimethylsiloxane-methylmercaptopropylsiloxanecopolymer with a SH content of 0.16 mol/100 g.

Suitable SiH containing crosslinkers (C4) are also known in the literature and commercially available. These generally include silanes, siloxanes, polysilanes, polysiloxanes, organosilanes, organosiloxanes, and organopolysiloxanes containing an average of two or more SiH groups per molecule. Examples include phenylmethylsilane, tetramethyldisilane, phenylsilane, γ,ω-dihydrido-polydimethylsiloxane, poly(dimethyl-methylhydrido)siloxane, hydrogenpolysilsesquioxane, poly(methylhydridosiloxane-co-silphenylene), poly(methylhydridosiloxane-co-silmethylene), and other copolymers of M, and/or D, and/or T, and optionally Q siloxane units which have at least 1 hydride (H) bonded to silicon in the M, and/or D, and/or T units, where M stands for the unit of $R^T{}_3SiO_{1/2}$, D for $R^T{}_2SiO_{2/2}$, T for $R^TSiO_{3/2}$, and Q for $SiO_{4/2}$, and $R^T$ is as defined above.

The amount of crosslinker added to the composition depends on various factors including the selection of ingredient (A), the selection of ingredient (B), the selection of crosslinker (C) and whether any other starting materials are present in the crosslinkable composition, however, crosslinker can be added in an amount of 0 to 80%, alternatively 0 to 50%, alternatively 0 to 30%, alternatively 0.5 to 50%, alternatively 0.5 to 30%, alternatively 1% to 50%, alternatively 1% to 30%, alternatively 1% to 20%, alternatively 1% to 10%, alternatively 5% to 50%, alternatively 5% to 30%, and alternatively 5% to 25%.

Compositions Containing the Copolymer

The copolymer described above is useful compositions for various applications, including personal care compositions and health care compositions. The invention further relates to a composition comprising the copolymer described above and at least one additional ingredient. The compositions are suitable for application to various substrates including skin or hair, e.g., human skin or human hair. The copolymer may act as a film forming agent in certain compositions. In one embodiment, a crosslinkable composition comprises (A) the copolymer described above and the at least one additional ingredient comprises (B) a curing catalyst. In an alternative embodiment, a personal care composition comprises (A) the copolymer described above and the at least one additional ingredient comprises (B) a carrier that permits application to the substrate.

Personal Care Composition

Suitable carriers for personal care applications, such as skin care, include nonaqueous media capable of evaporating on contact with the skin in less than one hour, at room temperature and atmospheric pressure, e.g., isoparaffins such as isododecane and silicone oils such as caprylyl methicone.

Alternatively, the carrier may comprise a surfactant and water, e.g., the composition may form an emulsion comprising (1) the copolymer, (2) a surfactant, and (3) water. As used herein, "emulsion" is meant to encompass water continuous emulsions (for example an oil in water type emulsion (o/w), or a silicone in water emulsion (s/w)), oil or silicone continuous emulsions (water in oil emulsions (w/o) or water in silicone emulsions (w/s)), or multiple emulsions (water/oil/water, oil/water/oil types, water/silicone/water, or silicone/water/silicone). The copolymer may be added to any type of emulsion by common mixing techniques. The addition of the copolymer may occur either during the preparation of the emulsion, or subsequently post added to a pre-formed emulsion. There are no special requirements or conditions needed to effect the mixing of copolymer of the present disclosure and the emulsion. Mixing techniques can be simple stirring, homogenizing, sonolating, and other mixing techniques known in the art to effect the formation of emulsions. The mixing can be conducted in a batch, semi-continuous, or continuous process.

The amount of copolymer added to the emulsion can vary and is not limited, however the amounts may range from a copolymer/emulsion weight ratio of 0.1/99 to 99/0.1, alternatively 1/99 to 99/1.

The emulsions used may be w/o, w/s, or multiple phase emulsions using silicone emulsifiers. In one embodiment, the water-in-silicone emulsifier in such formulation is nonionic and is selected from polyoxyalkylene-substituted silicones, silicone alkanolamides, silicone esters and silicone glycosides. Silicone-based surfactants may be used to form such emulsions and have been described, for example, in U.S. Pat. No. 4,122,029 to Gee et al., U.S. Pat. No. 5,387,417 to Rentsch, and U.S. Pat. No. 5,811,487 to Schulz et al.

Alternatively, the emulsion containing the copolymer may contain anionic surfactants, cationic surfactants, amphoteric surfactants, and nonionic surfactants. The anionic surfactants include (i) sulfonic acids and their salt derivatives, including alkyl, aralkyl, alkylnaphthalene, alkyldiphenyl ether sulfonic acids, and their salts, having at least 6 carbon atoms in the alkyl substituent, such as dodecylbenzene sulfonic acid, and its sodium salt or its amine salt; (ii) alkyl sulfates having at least 6 carbon atoms in the alkyl substituent, such as sodium lauryl sulfate; (iii) the sulfate esters of polyoxyethylene monoalkyl ethers; (iv) long chain carboxylic acid surfactants and their salts, such as lauric acid, steric acid, oleic acid, and their alkali metal and amine salts. Some other examples of anionic surfactants are alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates; ether sulfates having alkyl groups of eight or more carbon atoms such as sodium lauryl ether sulfate; and alkylaryl sulfonates having one or more alkyl groups of eight or more carbon atoms such as neutral salts of hexadecylbenzene sulfonic acid and $C_{20}$ alkylbenzene sulfonic acid.

Commercial anionic surfactants which can be used include the sodium salt of dodecylbenzene sulfonic acid sold under the trademark SIPONATE® DS-10 by Alcolac Inc., Baltimore, Maryland; sodium n-hexadecyl diphenyloxide disulfonate sold under the trademark DOW FAX® 8390 by The Dow Chemical Company, Midland, Mich.; the sodium salt of a secondary alkane sulfonate sold under the trademark HOSTAPUR® SAS 60 by Clariant Corporation, Charlotte, N.C.; N-acyl taurates such as sodium N-lauroyl methyl taurate sold under the trademark NIKKOL LMT® by Nikko Chemicals Company, Ltd., Tokyo, Japan; and linear alkyl benzene sulfonic acids sold under the trademark BIO-SOFT® S-100 by the Stepan Company, Northfield, Ill. Compositions of the latter type such as dodecylbenzene sulfonic acid, although a catalyst as noted above, can also function as the anionic surfactant when neutralized. Other suitable surfactants include sodium alkyl sulfonate such as HOSTAPUR® SAS-30. In one embodiment, the emulsifier is triethanolamine dodecylbenzene sulfonate, such as BIO-SOFT® N 300.

Cationic surfactants useful herein include compounds containing quaternary ammonium hydrophilic moieties in the molecule which are positively charged, such as quaternary ammonium salts represented by $R^8R^9R^{10}R^{11}N^+X^-$ where $R^8$ to $R^{11}$ are alkyl groups containing 1-30 carbon atoms, or alkyl groups derived from tallow, coconut oil, or soy; and X is a halogen, e.g., chlorine or bromine. Alternatively, the quaternary ammonium compounds may be alkyl trimethylammonium and dialkyldimethylammonium halides, or acetates, or hydroxides, having at least 8 carbon atoms in each alkyl substituent. Dialkyl dimethyl ammonium salts can be used and are represented by $R^{12}R^{13}N^+(CH_3)_2X^-$ where $R^{12}$ and $R^{13}$ are alkyl groups containing 12-30 carbon atoms or alkyl groups derived from tallow, coconut oil, or soy; and X is halogen. Monoalkyl trimethyl ammonium salts can be used and are represented by $R^{14}N^+(CH_3)_3X^-$ where $R^{14}$ is an alkyl group containing 12-30 carbon atoms or an alkyl group derived from tallow, coconut oil, or soy; and X is halogen, acetate, or hydroxide.

Representative quaternary ammonium halide salts are dodecyltrimethyl ammonium chloride/lauryltrimethyl ammonium chloride (LTAC), cetyltrimethyl ammonium chloride (CTAC), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide. These quaternary ammonium salts are commercially available under trademarks such as ADOGEN®, ARQUAD®, TOMAH®, and VARIQUAT®.

Other suitable cationic surfactants which can be used include (i) fatty acid amines and amides and their salts and derivatives, such as aliphatic fatty amines and their derivatives. Such cationic surfactants that are commercially available include compositions sold under the names Arquad T27 W, Arquad 16-29, by Akzo Nobel Chemicals Inc., Chicago, Ill.; and Ammonyx Cetac-30 by the Stepan Company, Northfield, Ill.

Suitable amphoteric surfactants include; betaines such as cocamidopropylbetaine, sultaines such as cocamidopropylhydroxysultaine, lecithin and hydrogenated lecithin, In one embodiment, the emulsifier is a combination of an anionic and nonionic surfactant. In a further embodiment, the anionic surfactant in the combination is an alkyl sulfonate or a dodecylbenzene sulfonate. In a further embodiment, the nonionic emulsifier is an alkyl-oxo alcohol polyglycol ether or an alkyl polyethylene glycol ether.

Some suitable nonionic surfactants which can be used include polyoxyethylene alkyl ethers, polyoxyethylene alkyl phenyl ethers, alkylglucosides, polyoxyethylene fatty acid esters, sorbitan fatty acid esters, and polyoxyethylene sorbitan fatty acid esters. Nonionic surfactants which are commercially available include compositions such as (i) 2,6,8-trimethyl-4-nonyl polyoxyethylene ether sold under the names Tergitol TMN-6 and Tergitol TMN-10; (ii) the C11-15 secondary alkyl polyoxyethylene ethers sold under the names Tergitol 15-S-7, Tergitol 15-S-9, Tergitol 15-S-15, Tergitol 15-S-30, and Tergitol 15-S-40, by the Dow Chemical Company, Midland, Mich.; octylphenyl polyoxyethylene (40) ether sold under the name Triton X405 by the Dow Chemical Company, Midland, Mich.; (iii) nonylphenyl polyoxyethylene (10) ether sold under the name Makon 10 by the Stepan Company, Northfield, Ill.; (iv) ethoxylated alcohols sold under the name Trycol 5953 by Henkel Corp./Emery Group, Cincinnati, Ohio; (v) ethoxylated alcohols sold under the name Brij L23 and Brij L4 by Croda Inc. Edison, N.J., (vi) alkyl-oxo alcohol polyglycol ethers such as ®GENAPOL UD 050, and Genapol UD110, (vii) alkyl polyethylene glycol ether based on C10-Guerbet alcohol and ethylene oxide such as LUTENSOL® XP 79.

Suitable nonionic surfactants also include poly(oxyethylene)-poly(oxypropylene)-poly(oxyethylene) tri-block copolymers. Poly(oxyethylene)-poly(oxypropylene)-poly(oxyethylene) tri-block copolymers are also commonly known as Poloxamers. They are nonionic triblock copolymers composed of a central hydrophobic chain of polyoxypropylene (poly(propylene oxide)) flanked by two hydrophilic chains of polyoxyethylene (poly(ethylene oxide)). Poly(oxyethylene)-poly(oxypropylene)-poly(oxyethylene) tri-block copolymers are commercially available from BASF (Florham Park, NJ) and are sold under the tradename PLURONIC®, such as Pluronic L61, L62, L64, L81, P84.

The nonionic surfactant may also be a silicone polyether (SPE). The silicone polyether as an emulsifier may have a rake type structure wherein the polyoxyethylene or polyoxyethylene-polyoxypropylene copolymeric units are grafted onto the siloxane backbone, or the SPE can have an ABA block copolymeric structure wherein A represents the polyether portion and B the siloxane portion of an ABA structure. Suitable silicone polyethers include Dow Corning® 5329 from Dow Corning Corporation of Midland, Mich. USA.

Other useful commercial nonionic surfactants are non-ylphenoxy polyethoxy ethanol (10EO) sold under the trademark MAKON® 10 by Stepan Company, Northfield, Ill.; polyoxyethylene 23 lauryl ether (Laureth-23) sold commercially under the trademark BRIJ® 35L by ICI Surfactants, Wilmington, Del.; and RENEX® 30, a polyoxyethylene ether alcohol sold by ICI Surfactants, Wilmington, Del.

Protective colloids, i.e., colloidal stabilizers, may be used, if desired, to enhance stability or to provide a specific rheological characteristic to the emulsion. As used herein, the terms "protective colloid" and/or "colloidal stabilizer" mean a nonionic molecule that is an effective agent for protecting charged colloidal particles in an aqueous media against flocculation. These compositions typically have a weight average molecular weight ranging from 1,000-300,000 and are typically more hydrophilic than the composition of the first emulsion polymer, as measured by weight-averaged solubility parameters. Colloidal stabilizers which can be used include hydroxyethyl cellulose having a weight average molecular weight between 50,000-150,000; N-vinyl pyrrolidone; polyvinyl alcohol having a weight average molecular weight between 10,000-200,000; partially acetylated polyvinyl alcohol; carboxymethyl cellulose; gums such as gum arabic; starches; proteins; and mixtures thereof. Preferred colloidal stabilizers are hydroxethyl cellulose and polyvinyl alcohol.

Since emulsions are susceptible to microbiological contamination a preservative can be added. Representative preservatives, which can be used include phenoxyethanol and ethylhexylglycerin; formaldehyde; 1,3-dimethylol-5,5-dimethyl hydantoin, e.g., DMDM Hydantoin; 5-bromo-5-nitro-1,3-dioxane; methyl or propyl paraben; sorbic acid; imidazolidinyl urea; and KATHON® CG (5-chloro-2-methyl-4-isothiazolin-3-one); caprylyl glycol; phenoxyethanol; benzyl alcohol; and/or benzoic acid.

The emulsions may contain a copolymer concentration of 1% to 70% based on the weight of the total emulsion, alternatively 2% to 60%. While emulsions containing less than 1% copolymer content can be made, such emulsions may be less valuable. The surfactant may be present at 0.05% to 30% based on the weight of the total emulsion, alternatively 0.1% to 20%. Water and optional ingredients constitute the balance of the emulsion to 100%.

The composition comprising the copolymer may comprise 1% to 70%, alternatively 2% to 65%, alternatively 5% to 60%, and alternatively 20% to 50% of the the copolymer, based on the weight of all ingredients in the composition. The carrier may be present in an amount sufficient to form a solution, dispersion or emulsion of the copolymer. In one embodiment, the balance of the composition to 100% may be the carrier. Alternatively, the composition may further comprise one or more optional ingredients in addition to the copolymer and the carrier. The selection of additional ingredients depends on the end use of the composition. The composition comprising the copolymer and a carrier, as described above, may be used to prepare a personal care composition, e.g., a hair care and/or a skin care composition.

Non-limiting examples of additional ingredients which may be formulated into the personal care compositions in addition to the copolymer composition described above include: silicones (e.g., fluids, gums, resins, elastomers, surfactants, and/or alkylmethylsilicones, and/or silicone carbinol fluids), anti-oxidants, cleansing agents, colorants (e.g., pigments and/or dyes), conditioning agents, deposition agents, electrolytes, emollients, exfoliating agents, foam boosters, fragrances, humectants, occlusive agents, pediculicides, pH control agents, pigments, preservatives, biocides, solvents (other than the carrier), stabilizers, sun-screening agents, suspending agents, tanning agents, other surfactants (e.g., other than the surfactant used when the composition is an emulsion), thickeners, vitamins, botanicals, fragrances, waxes, rheology-modifying agents, anti-dandruff, anti-acne, anti-carie, anti-perspirant/deodorant actives, pharmaceutical ingredients, and wound healing-promotion agents.

The personal care compositions may be functional with respect to the portion of the body to which they are applied, cosmetic, therapeutic, or some combination thereof. Conventional examples of such personal care compositions include, but are not limited to: antiperspirants and/or deodorants; wound management, wound protection, and/or wound care compositions; skin barriers; liquid bandages; scar and/or stretch mark treatments; skin care creams; skin care lotions; moisturizers; facial treatments such as acne or wrinkle removers; personal and/or facial cleansers; bath oils; perfumes; colognes; sachets; sunscreens; pre-shave and/or after-shave lotions; shaving soaps and/or shaving lathers; hair shampoos; hair conditioners (either leave in or rinse off); hair colorants; hair relaxants; hair styling aids such as sprays, fixatives, mousses, gels, permanents, depilatories, and/or cuticle coats; make-ups; color cosmetics; foundations; concealers; blushes; lipsticks; eyeliners; mascara; oil removers; color cosmetic removers; powders; and/or medicament creams, pastes or sprays including antiacne, dental hygienic, antibiotic, healing promotive, and/or nutritive, which may be preventative and/or therapeutic. The copolymer described above may be used as a film forming agent in any of such personal care compositions.

In general the personal care compositions may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. Generally, such personal care compositions can be prepared at room temperature if no solid materials at room temperature is present in the composition, using simple propeller mixers, Brookfield counter-rotating mixers, or homogenizing mixers. No special equipment or processing conditions are typically required. Depending on the type of form made, the method of preparation will be different, but conventional methods may be used.

The personal care compositions according to this invention can be used by the standard methods, such as applying them to the human body, e.g., skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the personal care compositions according to the present invention may be used in a conventional manner for example for conditioning the skin. An effective amount of the composition for the purpose is applied to the skin. Such effective amounts generally range from 1 mg/cm$^2$ to 3 mg/cm$^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the personal care compositions according to the invention on hair may use a conventional manner for conditioning hair. An effective amount of the composition for cleaning and/or conditioning hair is applied to the hair. Such effective amounts generally range from 0.5 g to 50 g, alternatively from 1 g to 20 g. Application to the hair typically includes working the composition through the hair such that most or all of the hair is contacted with the personal care composition. This method for cleaning and/or conditioning the hair comprises the steps of applying an effective amount of the hair care product to the hair, and then working the composition through the hair. These steps can be repeated as many times as desired to achieve the desired conditioning benefit.

Exemplary skin care compositions that can be made with the composition comprising the copolymer and the carrier, described above include, a foundation composition comprising: (1) the copolymer described above, (2) water, (3) a surfactant, (4) a thickener (e.g., sodium chloride), (5) an emollient (e.g., glycerin), (6) a preservative (e.g., phenoxyethanol), (7) a pigment, and (8) a silicone (e.g., a polydimethylsiloxane and/or an alkylmethylsiloxane).

Alternatively, the skin care composition comprising the copolymer and the carrier, described above, may be a lipstick composition comprising: (1) the copolymer described above, (2) a solvent (e.g. isododecane and/or cyclomethicone), (3) an emollient (e.g., a vegetable oil, a plant oil, a silicone, and/or an ester), (4) a wax (e.g., polyethylene, ceresin, ozokerite, synthetic, paraffin, alkyl silicones, and/or beeswax), (5) a fixative (e.g., a silicone resins such as MQ or TPr silicone resin and/or a silicone copolymer other than the copolymer described above), (6) a colorant (e.g., D&Cs Red #6, FD&C Yellow #5,6 Al Lake, Iron Oxides, TiO$_2$, ZnO, and/or Pearls), (7) an active (e.g., tocopherol acetate, sodium hyaluronate, amino acids, panthenol, and/or ascorbyl palmitate), (8) a fillers (e.g. mica, silica, boron nitride, starch, and/or acrylate copolymer), (9) an antioxidants and/or preservative (e.g., phenoxyethanol), and (10) a plasticizer (e.g., oleyl alcohol and/or petrolatum).

Alternatively, the skin care composition comprising the copolymer and the carrier, described above, may be an antiperspirant composition comprising: (1) the copolymer described above, (2) a wax and/or thickener (e.g., beeswax, sodium stearate, stearyl alcohol, and/or carnauba), (3) an emollient (e.g. mineral oil, cylcomethicone, propylene glycol, and/or alcohol, (4) a fixative (e.g., silicone MQ or copolymer type resins and/or acrylate copolymers), (5) an antiperspirant active (e.g. aluminum chlorohydrate), and (6) a fragrance and/or perfume.

Alternatively, the skin care composition comprising the copolymer and the carrier, described above, may be a sunscreen composition comprising: (1) the copolymer described above, (2) an organic or physical sun blocker (e.g., oxybenzone, octocrylene, titanium dioxide, zinc oxide, and/or avobenzone), (3) a preservatives (e.g., phenoxyethanol), (4) an emulsifier and/or surfactant, (5) an emollient, (6) a thickener, (7) water, and (8) a moisturizer (e.g., glycerin).

Exemplary hair care compositions that can be made with the composition comprising the copolymer and the carrier, described above, include a shampoo comprising: (1) the copolymer described above, or the emulsion of the copolymer described above, (2) water, and (3) an anionic surfactant and/or an amphoteric surfactant (e.g., sodium laureth sulfate), optionally (4) a preservative, and optionally (5) a deposition agent (e.g., a cationic deposition polymer), and optionally (6) a thickener (e.g., carbomer).

Alternatively, the hair care product may be a hair conditioner comprising: (A) the copolymer described above, or the emulsion of the copolymer described above, (B) water, optionally (C) a thickener (e.g., hydroxyethyl-cellulose), (D) a fatty alcohol (e.g., Cetearyl Alcohol), optionally (E) other emulsifiers (e.g., PEG-100 Stearate & Glyceryl Stearate), optionally (F) a preservative, and optionally (G) other conditioning agents (e.g., cationic surfactants and/or cationic polymers).

Alternatively, the composition comprising the copolymer and the carrier, described above, may be used as a leave-in or leave-on hair treatment composition.

The composition comprising the copolymer and a carrier, described above, can be used in a variety of personal care applications. In particular, said composition may be used in the personal care compositions disclosed in U.S. Pat. No. 6,051,216 to Barr et al.; U.S. Pat. No. 5,919,441 to Mendolia et al.; U.S. Pat. No. 5,981,680 to Petroff et al.; U.S. Patent Application 2010/0098648 to Yu, and WO 2004/060101 to Yu; in sunscreen compositions as disclosed in U.S. Pat. No. 6,916,464 to Hansenne et al.; in cosmetic compositions containing film-forming resins, as disclosed in U.S. Patent Application Publication 2003/0235552 to Yu; in the cosmetic compositions as disclosed in U.S. Patent Application Publication 2003/0235553 to Lu, U.S. Patent Application Publication 2003/0072730 to Tornilhac, U.S. Patent Application Publication 2003/0170188 to Ferrari et al., EP 1,266, 647 to Tornilhac, EP 1,266,648 to Ferrari, et al., EP1,266, 653 to Ferrari et al., WO2003/105789 to Lu, WO2004/ 000247 to Lu and WO2003/106614 to Lu; as additional agents to those disclosed in WO2004/054523 to Tournilhac; in long wearing cosmetic compositions as disclosed in U.S. Patent Application Publication 2004/0180032; and in transparent or translucent care and/or make up compositions as discussed in WO 2004/054524. The copolymer is useful as a film forming agent in various applications, such as the personal care compositions described above. Alternatively, the copolymer is useful in addition to, or instead of, the silicone acrylate in the personal care compositions in, for example, "A Second Generation Silicone Acrylate for use in Beauty Care Applications, IP.com Number: 000239161 Electronic Publication Date Oct. 17, 2014. The copolymer is useful as a film forming agent in addition to, or instead of, the phenylsilsesquioxane resin in, for example, "Personal Care Applications for Phenylsilsesquioxane Resins," IP.com Number IPCOM000248667D, Electronic Publication Date Dec. 22, 2016. These references disclose various color cosmetic formulations, such as foundations, blushes, lipsticks, lip glosses, mascaras, eye shadows, eyebrow gels and eyeliners; skin care compositions such as sun care formulations, antiperspirants and deodorants; and hair care formulations such as shampoos, hair conditioners (leave on or rinse off) and hair waxes.

When selecting ingredients for the personal care compositions described above, there may be overlap between types of ingredients because certain ingredients described herein may have more than one function. For example, certain silicone MQ resins may be useful as fixatives and additional film forming agents. Certain particulates such as titanium dioxide may be useful as pigments and sun blockers. When adding additional ingredients to the composition, the additional ingredients are distinct from one another.

Crosslinkable Composition

Alternatively, the copolymer prepared as described above may be used in crosslinkable composition, which comprises (A) the copolymer and (B) a curing catalyst. The crosslinkable composition may be, for example, a skin contact adhesive composition.

The copolymer prepared as described above can be crosslinked by any means that will initiate the reaction of the aliphatic unsaturation. The reaction can be initiated by thermally generated free radicals. It is also ultraviolet radiation crosslinkable via several different means. The aliphatic unsaturation can react with themselves, or additional reactive compounds (crosslinkers) can be added to react with the unsaturation. Suitable crosslinkers include but are not limited to other aliphatically unsaturated compounds such as acrylates and methacrylates, dialkenyl (such as divinyl and diallyl) compounds, thiol (SH containing) compounds, phosphines (PH containing), boranes (BH containing), and silanes (SiH containing). In a first embodiment, a crosslinkable composition comprises: (A) the copolymer described above, and (B) a curing catalyst.

(B) Curing Catalyst

The curing catalyst may be (B1) a free radical initiator or (B2) a hydrosilylation catalyst. The free radical initiator can be a peroxide, which can be thermally activated or activated by a reducing agent at room temperature. The peroxide may have formula $R^{MS}$-O—O-$R^{MS}$, where each $R^{MS}$ is independently a saturated monovalent hydrocarbon group such as alkyl as defined below or saturated monovalent halogenated hydrocarbon group, such as haloalkyl as defined below. Examples of peroxides include di-tert-butyl peroxide, bis(tert-butylperoxy)hexane, dicumyl peroxide, and bis(tert-butylperoxyisopropyl)benzene, 1,1-bis(tert-butyl peroxy)-3,3,3-trimethylcyclohexane, 2,5-dimethyl-2,5-di(tert-butyl-peroxy)hexane, 2,5-dimethyl-2,5-bis(tert-butylperoxy)hex-yne-3, (tert-butylperoxy)myristylcarbonate; and mixtures of two or more thereof. Alternatively, the free radical initiator can be a photo-activated compound. Photo-activated initiators are known in the literature and any known initiating systems can be used. These can be one component systems or two component systems. One component systems include benzoyl-chromophore based systems, substituted benzoyl-chromophore based ones, hydroxyl alkyl heterocyclic ketones, hydroxyl alkyl conjugated ketones, benzophenone- and thioxanthone-moiety- based systems, benzoyl phosphine oxide derivatives, phosphine oxide derivatives, trichloromethyl triazines, biradical generating ketones, some peroxides and diketones, azides and aromatic bis-azides, some azo, disulfide, disilane, diselenide, diphenylditelluride, digermane, and distanane derivatives, and compounds with carbon-germanium, carbon-silicon, carbon-sulfur, sulfur-silicon, sulfur-sulfur, and germanium-silicon cleavable bonds. Two component systems include ketone-hydrogen donor based systems and dye-based systems. Examples of such free radical initiators are known in the art and are commercially available, such as 2-hydroxy-2-methyl-1-phenyl-propan-1-one (commercially available as Darocur 1173). Other commercially available examples include 1-hydroxy-cyclohexyl- phenyl-ketone, benzophenone, 2-hydroxy-1-[4-(2-hydroxyethoxy) phenyl]-2-methyl-1-propanone, methylbenzoylformate, oxy-phenyl-acetic acid 2-[2 oxo-2 phenyl-acetoxy-ethoxy]-ethyl ester, oxy-phenyl-acetic 2-[2-hydroxy-ethoxy]-ethyl ester, alpha-dimethoxy-alpha-phenylacetophenone, 2-benzyl-2-(dimethylamino)-1-[4- (4-morpholinyl) phenyl]-1-butanone, 2-Methyl-1-[4-(methylthio)phenyl]-2-(4-morpholinyl)-1-propanone, diphenyl (2,4,6-trimethylbenzoyl)-phosphine oxide, phenyl bis (2,4,6-trimethyl benzoyl) phosphine oxide, and bis (eta 5-2,4-cyclopentadien-1-yl) or bis [2,6-difluoro-3-(1H-pyr-rol-1-yl) phenyl]titanium. The amount of free radical initiator added to this crosslinkable composition depends on various factors including the other ingredients of the composition, however, the amount may range from 0.01% to 10% based on the combined weights of all ingredients added to the composition. Alternatively the amount of free radical initiator may be 0.01% to 5%, alternatively 0.05% to 5%, alternatively 0.05% to 3%, alternatively 0.1% to 10%, alternatively 0.1% to 5%, and alternatively 0.1% to 3%. The composition may be crosslinked by exposure to ultra violet radiation, visible light, or infrared radiation, depending on where sufficient absorption occurs and how the absorbed energy is transferred to activate the initiator and produce free radicals. Alternatively the initiation systems can be activated by heat, or the activation is assisted by heat in combination with electromagnetic radiation. When crosslinking is activated by heat, additionally many other heat activated free radical initiators can be used. Examples include peroxides and azo compounds. Exemplary peroxides are known in the art, for example, those recited in U.S. Pat. Nos. 4,929,669; 5,082,886; 5,258,211; and 5,919,884.

The crosslinkable composition can also be crosslinked by reacting the aliphatic unsaturation with a compound with silicon hydride groups through a hydrosilylation reaction. This reaction is usually catalyzed by metal salts and other compounds, amines and other organic bases, peroxides, and/or complexes, and organic peroxides can be used to catalyze hydrosilylation. Hydrosilylation catalysts are known in the art and are commercially available. Such conventional hydrosilylation catalysts can be a metal selected from platinum, rhodium, ruthenium, palladium, osmium, and iridium. Alternatively, the hydrosilylation catalyst may be a compound of such a metal, for example, chloroplatinic acid, chloroplatinic acid hexahydrate, platinum dichloride, and complexes of said compounds with low molecular weight organopolysiloxanes or platinum compounds microencapsulated in a matrix or core/shell type structure. Complexes of platinum with low molecular weight organopolysiloxanes include 1,3-diethenyl-1,1,3,3-tetramethyldisiloxane complexes with platinum. These complexes may be microencapsulated in a resin matrix. Exemplary hydrosilylation catalysts are described in U.S. Pat. Nos. 3,159,601; 3,220,972; 3,296,291; 3,419,593; 3,516,946; 3,814,730; 3,989,668; 4,784,879; 5,036,117; and 5,175,325 and EP 0 347 895 B. Microencapsulated hydrosilylation catalysts and methods of preparing them are known in the art, as exemplified in U.S. Pat. Nos. 4,766,176 and 5,017,654.

(C) Crosslinker

The crosslinkable composition may optionally further comprise (C) a crosslinker, in addition to starting materials (A) and (B), described above. The crosslinker may be (C1) an acrylate crosslinker, (C2) a crosslinker containing alkenyl groups (other than in an acrylate group), (C3) a thiol-functional crosslinker, or (C4) an SiH containing crosslinker. The acrylate crosslinker and the crosslinker containing other alkenyl groups can contain one or more acrylate or alkenyl (e.g., vinyl) groups per molecule. Examples include but are not limited to methylmethacrylate, n-butyl acrylate, 2-ethyl hexyl methacrylate, ethylene glycol diacrylate, poly(ethylene glycol) diacrylate, neopentyl glycol diacrylate, trimethylolpropane triacrylate, pentaerythritol triacrylate, glycerol propoxylate triacrylate, trimethylolpropane propoxylate triacrylate, trimethylolpropane ethoxylate triacrylate, pentaerythritol tetraacrylate, di(trimethylolpropane) tetraacrylate, divinylbenzene, divinyl sulfone, 1,4-butanediol divinyl ether, ethylene glycol divinyl ether, di- tri-, and poly-ethylene glycol divinyl ether, and styrene.

Thiol-functional crosslinkers suitable for starting material (C3) are known in the art and are commercially available. They can be organic thiol compounds (SH containing compounds) with an average of two or more SH groups per molecule, or mercaptofunctional silanes, siloxanes, polysilanes, polysiloxanes, organosilanes, organosiloxanes, and organopolysiloxanes containing an average of two or more SH groups per molecule. Suitable thiol-functional crosslinkers include: a trimethylsiloxy terminated dimethylsiloxane-methylmercaptopropylsiloxane copolymer with a SH content of 0.35 mol/100 g; a trimethylsiloxy terminated dimethylsiloxane-methylmercaptopropylsiloxane copolymer with a SH content of 0.16 mol/100 g, purchased from Gelest, Inc.; a trimethylsiloxy terminated dimethylsiloxane-methylmercaptopropylsiloxane copolymer with a SH content of 0.05 mol/100 g, purchased from Gelest, Inc.; and a trimethylsiloxy terminated dimethylsiloxane-methylmercaptopropylsiloxane copolymer with a SH content of 0.16 mol/100 g.

The SiH containing crosslinkers suitable for starting material (C4) are also known in the literature and commercially available. These generally include silanes, siloxanes, polysilanes, polysiloxanes, organosilanes, organosiloxanes, and organopolysiloxanes containing an average of two or more silicon bonded hydrogen (SiH) groups per molecule. Examples include phenylmethylsilane, tetramethyldisilane, phenylsilane, γ,ω-dihydrido-polydimethylsiloxane, poly(dimethyl-methylhydrido)siloxane, hydrogenpolysilsesquioxane, poly(methylhydridosiloxane-co-silphenylene), poly(methylhydridosiloxane-co-silmethylene), and other copolymers of M, and/or D, and/or T, and optionally Q siloxane units which have at least 1 hydride (H) bonded to silicon in the M, and/or D, and/or T units, where M stands for the unit of $R^T 3SiO_{1/2}$, D for $R^T 2SiO_{2/2}$, T for $R^T SiO_{3/2}$, and Q for $SiO_{4/2}$, and $R^T$ is as defined above. When the SiH crosslinker is present, the crosslinkable composition may be crosslinked via hydrosilylation reaction, and the crosslinkable composition further comprises a hydrosilylation catalyst, as described above. In this embodiment, a skin contact adhesive prepared using the crosslinkable composition could be used in an application other than a transdermal drug delivery application, or in an application where the hydrosilylation catalyst does not detrimentally affect any active ingredient selected as ingredient (D).

The amount of crosslinker added to the composition depends on various factors including the selection of starting material (A), the selection of starting material (B), the selection of the crosslinker (C) and whether any other starting materials are present in the crosslinkable composition, however, (C) the crosslinker can be added in an amount of 0 to 80%, alternatively 0 to 50%, alternatively 0 to 30%, alternatively 0.5 to 50%, alternatively 0.5 to 30%, alternatively 1% to 50%, alternatively 1% to 30%, alternatively 1% to 20%, alternatively 1% to 10%, alternatively 5% to 50%, alternatively 5% to 30%, and alternatively 5% to 25%, based on the weight of the crosslinkable composition.

This invention further relates to a skin contact adhesive composition. The skin contact adhesive composition comprises starting materials (A), (B) and optionally (C) as described above. The skin contact adhesive further comprises one or both of (D) an active ingredient and (E) an excipient.

(D) Active Ingredient

Ingredient (D) may be added, for example, when the skin contact adhesive composition will be used to prepare a skin contact adhesive in a scar treatment application, a cosmetic patch application, a transdermal drug delivery application, and/or in an application for delivery of the active ingredient to the skin. The specific active ingredients used are not critical to this invention and as used herein the term "active ingredient" is to be construed in its broadest sense as a material intended to produce some beneficial effect on the organism to which it is applied.

Exemplary active ingredients suitable for ingredient (D) include, without limitation, drugs that act upon the central nervous system, drugs affecting renal function, drugs affecting cardiovascular function, drugs affecting gastrointestinal function, drugs for treatment of helminthiasis, antimicrobial agents such as silver, silver compounds, and/or chlorhexidine, nutrients, hormones, steroids, and drugs for treatment of dermatoses; see for example, those disclosed in U.S. Patent Application Publication US2007/0172518 paragraph [0014] and those listed in PCT Publication WO2007/092350 at pp. 21-28.

Other suitable active ingredients for ingredient (D) include non-steroidal anti-inflammatory drugs such as salicylates e.g., acetylsalicylic acid; propionic acid derivatives e.g., (RS)-2-(4-(2-methylpropyl)phenyl)propanoic acid (ibuprofen); acetic acid derivatives e.g., 2-{1-[(4-chlorophenyl)carbonyl]-5-methoxy-2-methyl-1H-indol-3-yl}acetic acid (indomethacin), enolic acid derivatives; anthranilic acid derivatives, COX-2 inhibitors e.g., N-(4-hydroxyphenyl)ethanamide N-(4-hydroxyphenyl)acetamide (acetaminophen), and sulfonanilides. Other suitable active ingredients for ingredient (D) include local anesthetics such those containing an ester group e.g., ethyl 4-aminobenzoate (benzocaine); those containing an amide group e.g., 2-(diethylamino)-N-(2,6-dimethylphenyl)acetamide (lidocaine); and naturally derived local anesthetics e.g., (1R,2S,5R)-2-isopropyl-5-methylcyclohexanol (menthol).

One skilled in the art would recognize that in the laminate articles described below, (D) the active ingredient may be included in the skin contact adhesive prepared by including ingredient (D) in the skin contact adhesive composition described herein (i.e., before crosslinking said composition to form the skin contact adhesive). Alternatively, (D) the active ingredient may be included in a separate reservoir within the laminate article, and not mixed into the skin contact adhesive prepared from the skin contact adhesive composition.

The amount of (D) the active ingredient used in the skin contact adhesive composition depends on various factors including the type of active ingredient selected for ingredient (D), the and type of laminate article in which the active ingredient will be incorporated, and the selection of any other ingredients in the crosslinkable composition. However, the amount of ingredient (D) may be 0 to 45%, alternatively greater than 0 to 25%, alternatively greater than 0 to 15%, alternatively greater than 0 to 10%, alternatively greater than 0.1% to 10%, alternatively greater than 1% to 10%, based on the weight of the skin contact adhesive composition.

(E) Excipient

The excipient may be any ingredient that is distinct from ingredient (D) that is added to the crosslinkable composition to provide one or more benefits during and/or after making the crosslinkable composition and/or to provide one or more benefits to the skin contact adhesive. For example, the excipient may be (F) a stabilizer, (G) a binder, (H) a filler, (I) a solubilizer, (J) a skin penetration enhancer (e.g., for transdermal drug delivery applications), (K) an adhesion promoter, (L) an agent to improve moisture permeability, or a combination of two or more of (F), (G), (H), (I), (J), (K), and (L).

(F) Stabilizer

The composition may optionally further comprise (F) a stabilizer. The stabilizer may comprise an antioxidant, such as vitamin A, vitamin E, vitamin C, retinyl palmitate, selenium, benzenepropanoic acid, 3,5-bis(1,1dimethyl-ethyl)-4-hycroxy-C7-C9 branched alkyl esters (Irganox® 1135 from BASF), pentaerythritoltetrakis[3-(3,5-di-tert-butyl-4-hydroxyphenyl) propionate] (Irganox® 1010 from BASF), octadecyl-3-(3,5-di-tert-butyl-4-hydroxyphenyl) propionate (Irganox® 1076 from BASF), 1,3,5-Trimethyl-2,4,6-tris(3,5-di-tert-butyl-4-hydroxybenzyl)benzene (Irganox® 1330 also from BASF), 2-methyl-4,6-bis [(octylthio)methyl]phenol (Irganox® 1520 from BASF) 2,6-di-tert-butyl-methylphenol (BHT), 2,2'-methylene-bis-(6-tert-butyl-4-methylphenol) (Vulkanox BKF from LanXess), or mixtures thereof. Alternatively, the stabilizer may comprise an amino acid such as cysteine, methionine, or combinations thereof. Alternatively, the stabilizer may comprise a paraben, such as methyl paraben, propyl paraben, or combinations thereof. The amount of stabilizer depends on various factors including whether the composition will be heated and whether ingredient (D) will be added, however, the stabilizer may be present in an amount from 0 to 2%, alternatively 0 to 1%, alternatively 0.1% to 1%, alternatively 0.2% to 0.7%, and alternatively 0.2% to 0.6% based on the weight of the crosslinkable composition.

(G) Binder

Ingredient (G), a binder, may optionally be added to the crosslinkable composition. Suitable binders include saccharides and their derivatives (e.g., disaccharides such as sucrose and lactose, polysaccharides such as starches or cellulose, or sugar alcohols such as xylitol, sorbitol or malitol. Other suitable binders include proteins such as gelatin. The amount of binder depends on various factors including the type of laminate article and the selection of other ingredients in the composition, however, the amount of binder may be 0 to 50% based on the weight of the crosslinkable composition.

(H) Filler

Ingredient (H), a filler, may optionally be added to the crosslinkable composition. Suitable fillers for ingredient (H) include but are not limited to silica to help prevent cold flow of the crosslinkable composition off the support. The filler selected is of a type and is present in an amount so as not to detrimentally impact adhesion of the skin contact adhesive. The amount of filler may be 0 to 2%, alternatively 0 to 1%, based on the weight of the crosslinkable composition.

(I) Solubilizer

Ingredient (I), a solubilizer, may optionally be added to the crosslinkable composition. Suitable solubilizers include dimethylsulfoxide, povidone (PVP) and natural oils such as mineral oil, sunflower oil, and peanut oil. Esters, glycols, polyether, may help solubilize (D) the active ingredient (i.e., keep ingredient (D) in a noncrystalline state in the crosslinkable composition, and the skin contact adhesive prepared therefrom, to facilitate permeation of the active ingredient to the skin (and/or into the skin). The solubilizer may be present at 0 to 50%, alternatively 0 to 40%, alternatively 0 to 25%, alternatively greater than 0 to 20%, and alternatively 20% to 25%, based on the weight of the crosslinkable composition. Alternatively, the solubilizer suitable for ingredient (I) may be the solvent, described above for making the copolymer.

(J) Skin Penetration Enhancer

Ingredient (J), a skin penetration enhancer, may optionally be added to the crosslinkable composition. Suitable skin penetration enhancers include glycols such as propylene glycol and polyethylene glycol; organic acids such as oleic acid; fatty alcohols such as oleyl alcohol; and amines. The amount of ingredient (J) depends on various factors including where the skin contact adhesive prepared from the crosslinkable composition will be applied, the length of time the skin contact adhesive will be applied, and the purpose (e.g., wound dressing or transdermal drug delivery), however the amount may range from 0 to less than 20%, alternatively 1% to 2% based on the weight of the crosslinkable composition.

(K) Adhesion Promoter

Materials known in the art as skin contact adhesives may be mixed with the composition described herein to adjust adhesive properties, such as release force required to remove the skin contact adhesive and amount of residue remaining on skin. These materials may be used herein as adhesion promoters. Exemplary adhesion promoters include hydrocolloids. The amount of adhesion promoter depends on the type of adhesion promoter selected and the amount of adhesion desired, however the amount of adhesion promoter may be 0 to less than 20%, alternatively 1% to 2%, based on the weight of the crosslinkable composition.

(L) Agent to Improve Moisture Permeability

Ingredient (L) is an agent to improve moisture permeability, which may optionally be added to the crosslinkable composition. Suitable agents for ingredient (L) included but are not limited to hydrocolloids, gelatins, polymers such as CMC carboxymethylcellulose, and polyethylene oxide. The amount of ingredient (L) depends on various factors including the selection of the other ingredients in the crosslinkable composition and the end use for the skin contact adhesive prepared therefrom. However, the amount of ingredient (L), when present, may be 0 to 50%%, alternatively 0.1% to 25%, alternatively 0.1% to 10%, alternatively 1% to 10%, based on the weight of the crosslinkable composition. One skilled in the art would recognize that certain agents that improve moisture permeability may also act as mucoadhesives that make the dressing adhere better as moisture content increases.

When selecting ingredients for the crosslinkable composition described above, there may be overlap between types of ingredients because certain ingredients described herein may have more than one function. For example, certain hydrocolloids may be useful as agents to improve moisture permeability (L) and as adhesion promoters (K). Gelatin may be useful as an agent to improve moisture permeability (L) and as a binder (G). Certain nutrients such as vitamin A and vitamin E may be useful as an active ingredient (D) and a stabilizer (F). When adding ingredients to the crosslinkable composition, the ingredients are distinct from one another. One skilled in the art would recognize that certain ingredients may be used in both personal care compositions and healthcare compositions, for the same or different purposes. For example, certain colloids may be useful for different purposes in personal care compositions where the copolymer is used as a film forming agent and crosslinkable compositions.

Skin Contact Adhesive

A skin contact adhesive composition may be formulated including the copolymer described above. The skin contact adhesive is prepared by crosslinking the crosslinkable composition described above. Crosslinking may be performed by any convenient means, such as exposing the crosslinkable composition to heat and/or radiation such as electron beam or ultra violet (UV) radiation. When heat is used to crosslink the crosslinkable composition, a temperature from 25 to 200° C. can be used for a duration of less than five seconds to two hours. When electron beam is used to crosslink the crosslinkable composition, an accelerating voltage of 75 kV to 350 kV can be used and a dosage of 5 to 250 kilogray (kGy) is usually sufficient to crosslink the composition. When UV is used, a light source of 200 nm to 450 nm is suitable, and can be generated by a mercury vapor lamp (Type H, D, or V for different wavelengths), a fluorescent lamp, or an UV LED lamp. The power rating of the lamp needed depends on the composition and can be any emitting irradiation at a dosage of at least 0.001 $mJ/cm^2$, alternatively from 0.01 to 2000 $mJ/cm^2$, alternatively from 0.1 to 1000 $mJ/cm^2$, alternatively from 1 to 1000 $mJ/cm^2$, alternatively from 10 to 500 $mJ/cm^2$. Without wishing to be bound by theory, it is thought that the crosslinking reaction will not detrimentally affect ingredient (D), when present.

The skin contact adhesive prepared by crosslinking the crosslinkable composition is useful in applications such as adhesives for medical tapes, adhesives for wound dressings, adhesives for prosthetics, ostomy appliance adhesives, adhesives for medical monitoring appliances, adhesives for cosmetic patches, adhesives for scar therapy treatments, and transdermal drug delivery systems.

Laminate Article

This invention further relates to a laminate article. The laminate article comprises:
i) a support having a skin facing surface and an opposed surface, which is intended to be facing away from skin,
ii) a skin contact adhesive on at least a portion of the skin facing surface, where the skin contact adhesive has a skin contact surface opposite the skin facing surface of the support.

The support is a material that can readily be applied to a part of the wearer's body. The support may be a plastic film, such as polyurethane, a polyolefin such as low density polyethylene (LDPE), medium density polyethylene (MDPE), high density polyethylene (HDPE), or polypropylene; a polyolefin/polyurethane composite; polyester; or ethylene vinyl acetate (EVA). Alternatively, the support may be paper, fabric (woven or nonwoven), silicone rubber, or foam. All, or a portion, of the support may optionally have a plurality of holes, e.g., be perforated or apertured, to provide for air permeability in the laminate article. Suitable supports are known, see for example PCT Publications WO2013/030580 and WO2014/116281 at pages 5-6.

The skin contact adhesive is on at least a portion of the skin facing surface of the support. For certain applications, such as transdermal drug delivery, the skin contact adhesive may cover all or most of the skin facing surface of the support to maximize the surface area through which the drug can be transferred. Alternatively, the skin contact adhesive may be on a portion of the skin facing surface of the support, for example, when the skin contact adhesive will be used to adhere an absorbent material to a wound. The amount (thickness) of the skin contact adhesive on the support will vary depending on various factors including the application (e.g., ostomy, wound care, and other applications where strong adhesion for longer time periods may have a thicker skin contact adhesive on the support, but adhesives for transdermal drug delivery or bandages or medical tapes may have a thinner skin contact adhesive on the support. Thickness may be uniform. Alternatively, thickness may be non-uniform on any given support, e.g., thicker toward the middle and thinner at or near the edge of the support). However, thickness of the skin contact adhesive may range from 0.0635 mm to 2.54 mm, alternatively 0.254 mm to 1 mm.

FIG. 1 is a partial cross section of a laminate article 100 according to this invention. The laminate article 100 comprises a support 101 having a layer of skin contact adhesive 102 on a skin facing surface 104 of the support 101. A release liner 103 covers the skin contacting surface 105 of the layer of skin contact adhesive 102. The support 101 may be a backing for a medical tape or adhesive bandage or other wound dressing, and is as described above.

Figure 4:
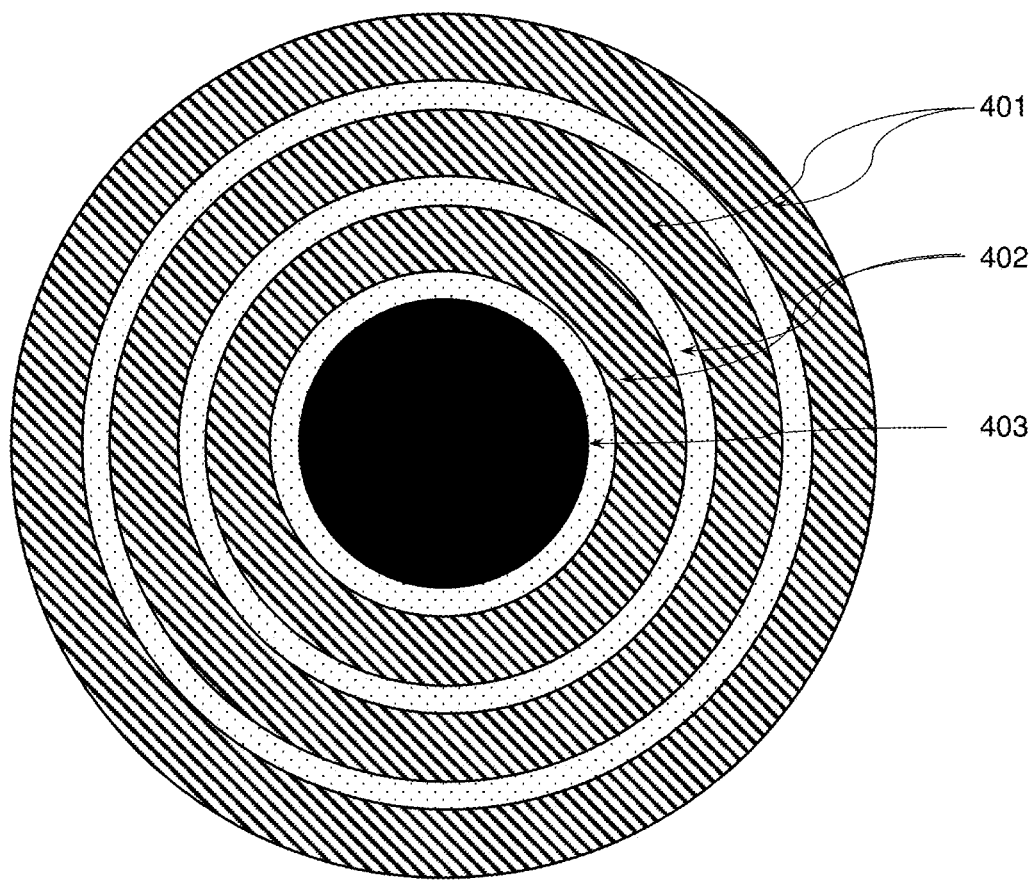
FIG. 4 shows a flange 400 for use in an ostomy appliance including the skin contact adhesive 402 including the copolymer described herein.

The layer of skin contact adhesive can be continuous or discontinuous. When discontinuous, the layer may be in various forms such as lines, line segments, dots, or flecks. The discontinuous forms may be in a uniform pattern across the surface of the support, or have different patterns at different regions of the support. An example is in FIG. 4, which shows a flange 400 for use in an ostomy appliance (not shown). The flange 400 has a support member 401 defining an aperture 403. The skin contact adhesive 402 described herein is formed in a discontinuous layer (shown as circular lines) on the support member 401.

The laminate article may further comprise one or more additional layers. For example, the laminate article may further comprise iii) a release liner covering the skin contact surface of the skin contact adhesive. The release liner is removable and may be used during shipping and storage of the laminate article before use. The skin contact adhesive can be exposed by removal of the release liner.

Suitable release liners include liners made of or coated with polyethylene, polypropylene, fluorocarbons, and fluorosilicone coated release papers and fluorosilicone coated plastic films. Suitable release liners are known and are described for example, in PCT Publication WO2007/092350. Without wishing to be bound by theory, it is thought that one benefit of the skin contact adhesive prepared by crosslinking the crosslinkable composition described herein is that release liners without fluorinated coatings (e.g., without fluorocarbons and without fluorosilicones) can be effectively used with the skin contact adhesive. Release liners with fluorinated coatings are typically more expensive than release liners without a fluorinated coating. Alternatively, release liners include liners made of or coated with polyethylene or polypropylene.

The laminate article may optionally further comprise iv) an absorbent layer. The absorbent layer may be mounted to the skin contact surface of the skin contact adhesive when the absorbent layer will contact the skin (e.g., a wound) directly, such as when the laminate article is an adhesive bandage such as that shown in FIG. 2 or in Canadian Patent Publication CA02585933. FIG. 2A shows a perspective view of an adhesive bandage 200 including a thin layer of the skin contact adhesive 202 described herein. FIG. 2B shows a cross sectional view of the adhesive bandage 200 taken along line A-A in FIG. 2A. The adhesive bandage 200 has a perforated plastic support 204 with the layer of the skin contact adhesive 202 on a skin facing surface 203 of the support 204. An absorbent layer 201 is on the skin contact surface 205 of the skin contact adhesive 202. Alternatively, the absorbent layer may be located between the skin contact adhesive and the support, for example, when the skin contact adhesive described herein is used in a wound dressing such as that shown in PCT Publication WO2007/092350.

The absorbent layer may be any suitable material such as a textile or polymer composition that is capable of absorbing fluid (e.g., exudate from a wound). The absorbent layer may be a commercially available product, see PCT Publication WO2007/092350 for examples of absorbent polymers, at pages 12 to 15. Examples include but are not limited to: thermoplastic polymers, block copolymers (other than ingredient (A)), polyolefins, hydrogels, and hydrocolloids.

The laminate article may further comprise v) a carrier. The carrier may be used to provide some rigidity to the laminate article and to enable the laminate article to be placed over a wound with minimal wrinkling and to avoid having the skin contact adhesive stick to itself during application of the laminate article to a wearer. The carrier may optionally be removed, e.g., after the laminate article is adhesively secured to the skin. The carrier may be mounted on the opposed surface of the support, intended to be facing away from the skin.

The carrier can be ethylene vinyl acetate (EVA), polyethylene film, polyester film, or paper coated with an EVA coating. One skilled in the art would recognize that the carrier may have the same materials of construction as the support, or different materials of construction. The carrier, as used herein, refers to a separate, discrete, piece of the laminate article.

Figure 3:
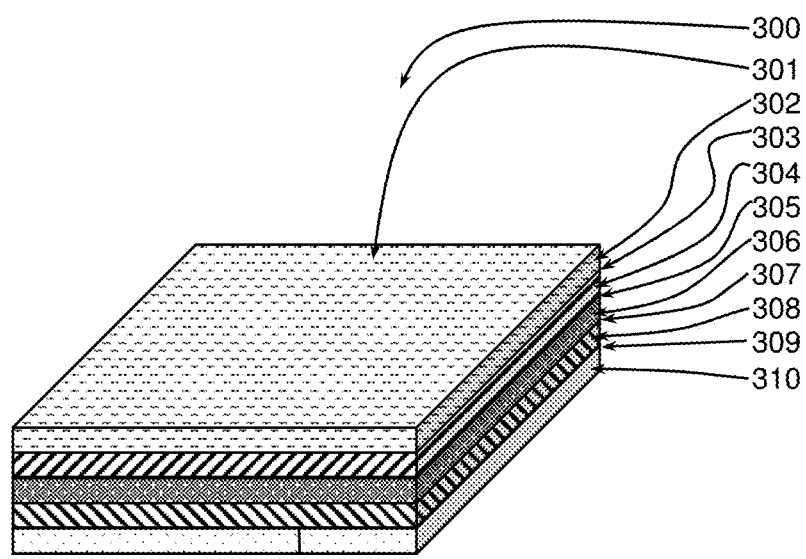
FIG. 3 is a partial cross section of a wound dressing in the form of a laminate article 300 including the skin contact adhesive 308 including the copolymer described herein.

FIG. 3 is a partial cross section of an alternative laminate article 300 according to this invention. The laminate article 300 has a support 304 with a skin facing surface 305 and an opposed surface 303 intended to face away from the skin. The skin contact adhesive (described herein) 308 is mounted to the skin facing surface 305 of the support 304. The skin contact adhesive 308 forms a layer with a skin contact surface 309. A release liner 310 (with two parts that can be peeled away separately) covers the skin contact surface 309 of the skin contact adhesive 308. The laminate article further comprises an absorbent layer 306 between the skin facing surface 305 of the support 304 and the opposed surface 307 of the skin contact adhesive 308. The laminate article further comprises a carrier 302 having a skin facing surface and an opposed surface 301. The carrier 302 is removably affixed to the opposed surface 303 of the support 304.

Method for Making a Laminate Article

A method for making the laminate article comprises:
I) forming a layer of the crosslinkable composition described above on at least a portion of a skin facing surface of a support, and
II) crosslinking the crosslinkable composition to form the skin contact adhesive.

The method may optionally further comprise: III) applying a release liner to a skin contact surface of the skin contact adhesive opposite the skin facing surface of the support. Step III) may be performed either before or after step II). The method may further comprise: IV) compressing the crosslinkable composition between the support and the release liner before crosslinking in step II).

The crosslinkable composition may be applied to support by any convenient means, e.g., dip coating, extrusion, spray coating, knife coating or roll coating. The crosslinkable composition may be applied to the support or the release liner first. The composition may be applied to the support using the method described, for example, in U.S. Patent Application Publication US2007/0172518 (substituting the crosslinkable composition described herein for the matrix described in the reference). Alternatively, the crosslinkable composition may be sandwiched between the support and release liners, and pressure may be applied to form the laminate article and/or crosslink the crosslinkable composition to form the skin contact adhesive. Laminate articles may be prepared as described in WO2015/075448, except using the composition of this invention instead of the polyurethane gel adhesive formulation disclosed in the reference.

The method for making the laminate article may optionally further comprise: III) sterilizing the laminate article. The laminate article including the skin contact adhesive is capable of being sterilized. The laminate article may be sterilized using known sterilizing means such as irradiating (e.g., with electron beam or gamma radiation) and/or heating such as with dry heat or steam. Sterilizing in step III) may be performed as a separate step after step I) or step II), as described above. Alternatively, sterilizing may be performed concurrently with steps I) and/or step II). For example, heating and/or irradiating may be performed to crosslink the crosslinkable composition, remove solvent, and/or sterilize.

Applications for the Skin Contact Adhesive

The skin contact adhesive described herein is suitable for use in various applications. The skin contact adhesive prepared by crosslinking the crosslinkable composition is useful in applications such as adhesives for medical tapes, adhesives for wound dressings, adhesives for prosthetics, ostomy appliance adhesives, adhesives for medical monitoring appliances, adhesives for scar therapy treatments, and transdermal drug delivery systems.

For example, the laminate article described above may comprise the support and the skin contact adhesive described above, on all or a portion of a surface of the support. The skin contact adhesive may be formed in a layer which is continuous or discontinuous. In one embodiment, the laminate article described above may be useful as an adhesive element. The skin contact adhesive may be applied to a skin facing surface of a support, and the skin contact adhesive may be used to adhere the support to the skin of a wearer. For example, the skin contact adhesive described above may be used to adhere a prosthetic to a wearer with a limb difference, or the skin contact adhesive may be used to adhere an ostomy appliance to a patient with a stoma. An ostomy appliance typically comprises a pouch for collection of waste, which is attached to a flange defining an aperture. The flange has an adhesive on the skin facing surface, where the adhesive surrounds the opening for attachment to the skin of a patient with a stoma (as described above in FIG. 4).

The skin contact adhesive described herein may be used in would care and ostomy care applications for adhesion to the skin, instead of the pressure sensitive adhesive disclosed in U.S. Patent Application Publication US2005/0163978, or instead of the adhesive used in U.S. Patent Application Publication US2014/0323941.

The skin contact adhesive described herein is suitable for use in wound dressings. For example, the skin contact adhesive described herein may be used as the skin contacting barrier layer instead of the hydrocolloids in U.S. Pat. No. 5,998,694. The skin contact adhesive described herein may be used in the wound cover of PCT Publication WO2007/

092350 and U.S. Patent Application Publications US2009/0105670 and US2015/0313593.

Alternatively, the skin contact adhesive described herein may be used in a transdermal drug delivery system. In this embodiment, the crosslinkable composition described above comprises ingredient (D) the active ingredient and may further comprise (E) the excipient. Without wishing to be bound by theory, it is thought that this invention may provide the benefit that crosslinking the composition to form the skin contact adhesive does not detrimentally affect (D) the active ingredient. The skin contact adhesive of this invention may be used, for example, in the transdermal drug delivery systems described in U.S. Pat. Nos. 4,840,796 and 4,951,657; and U.S. Patent Application Publications US2005/0048104 and US2007/0172518.

Coating Composition

The crosslinkable composition comprising starting materials (A), (B) and optionally (C), described above, may alternatively be used in a coating composition, e.g., for forming a coating on a substrate. The coating composition comprises: (a) the copolymer composition comprising starting materials (A), (B) and optionally (C), described above, and (b) a coating additive. The coating additive may be selected from (b1) a water scavenger, (b2) a pigment, (b3) a diluent, (b4) a filler, (b5) a rust inhibitor, (b6) a plasticizer, (b7) a thickening agent, (b8) a pigment dispersant, (b9) a flow aid, (b10) a solvent, (b11) an adhesion promoter, (b12) a catalyst, (b13) an organic co-binder, (b14) a siloxane co-binder, (b15) a matting agent, (b16) a leveling agent, (b17) a wax, (b18) a texturizing additive, (b19) an anti-scratching additive, (b20) a gloss modifying additive, (b21) a stabilizer, and (b22) a crosslinker, or a combination of two or more of (b1), (b2), (b3), (b4), (b5), (b6), (b7), (b8), (b9), (b10), (b11), (b12)(b13), (b14), (b15), (b16), (b17), (b18), (b19), (b20), (b21) and (b22). Suitable fillers include silica and titanium dioxide, or zirconium dioxide. Suitable adhesion promoters include alkoxysilanes such as 3-glycidoxy-propyltrimethoxysilane. Suitable solvents are as described above in the method for making the copolymer. Examples of suitable (b2) pigments, (b3) diluents, (b4) fillers, (b5) rust inhibitors, (b6) plasticizers, (b7) thickening agents, (b8) pigment dispersants, (b9) flow aids, (b10) solvents, and (b11) adhesion promoters are disclosed in U.S. Patent Application Publication Number 2015/0031797 and PCT Publications WO2015/097064, WO2015/100258, and WO2016/126362. The catalyst used in the coating composition as starting material (b12) may be the same as described as starting material e) described above and may be present in the coating composition in an amount of 0.01% to 5.00% by weight based on combined weights of all starting materials used to make the composition. Starting material, (b13) is an organic co- binder such as a polyol, polyamine, or polyisocyanate; which can be added to the coating composition in an amount of 0 to 99% based on combined weights of all starting materials used to make the composition. Starting material (b14) is a siloxane co-binder that may be added in an amount of 0 to 99%, based on combined weights of all starting materials in the composition. Starting material (b15) is a matting agent that can be 0 to 30% based on combined weights of all starting materials in the composition. Starting material (b16) is a leveling agent, which can be present in an amount of 0 to 10% of the composition. Starting material, (b17) wax can comprise 0 to 20% of the composition described herein. Starting material, (b18) is a texturing additives that can be added to the composition in an amount of 0 to 20%. Starting materials (b19), (b20), (b21), and (b22) combined, can be 0 to 15%, all based on the total amount of all starting materials in the coating composition.

The coating composition may be crosslinked to form a coating such as a primer or a top coat on a substrate. The substrate can be a metal, glass, wood, painted layer, plastic foil, a fiber and/or textile, or leather. The coating composition can be applied to the substrate, e.g., fiber and/or textile during making the fibers or textiles, or later such as during laundering textiles. After application, solvent (if any) can be removed from the coating composition for example by drying the coating composition at ambient or elevated temperature. The amount of treatment composition applied to the substrate, e.g., fibers and textiles is typically sufficient to provide 0.1 to 15 weight percent of the composition on the substrate, based on the dry weight of the substrate, alternatively in an amount of 0.2 to 5 weight percent based on the dry weight of the substrate.

Fibers and textiles that can be treated with the treatment composition include natural fibers such as cotton, silk, linen, and wool; regenerated fibers such as rayon and acetate; synthetic fibers such as polyesters, polyamides, polyacrylonitriles, polyethylenes, and polypropylenes; combinations, and blends thereof. The form of the fibers can include threads, filaments, tows, yarns, woven fabrics, knitted materials, non-woven materials, paper, and carpet. For purposes of this application, additional substrates can be treated with the treatment composition, including leather. Without wishing to be bound by theory, it is thought that textiles treated with the silicone block copolymer have a feel on hand comparable to conventional hydrophobic silicone, but do not significantly impact negatively on the hydrophilicity of the textile. Without wishing to be bound by theory, it is thought that a coating formed from the coating composition described above may have one or more benefits of high gloss, flexibility, hardness, scratch resistance, and resistance to weathering, resistance to ultra-violet radiation exposure, or two or more thereof.

EXAMPLES

Some embodiments of the invention will now be described in detail in the examples below. Reference Examples are not prior art unless so indicated.

TABLE 1

Abbreviations including starting materials used.

| Abbreviation | Meaning |
| --- | --- |
| TPDA | Trimethylol propane diallylether, from Aldrich |
| DA | Diallyl amine, from TCI |
| PTAE | Pentaerythritol triallylether, from Aldrich |
| PTA | Pentaerythritol triacrylate, from Aldrich |
| APMA | 3-(Acryloxy)-2-hydroxypropylmethacrylate, from Aldrich |
| EtAc | Ethyl acetate, from Sigma-Aldrich |
| EtOH | 200 Proof Ethanol, from Aldrich. Used to ensure residual NCO is completely reacted |

TABLE 1-continued

Abbreviations including starting materials used.

| Abbreviation | Meaning |
|---|---|
| HDI | Hexamethylene diisocyanate, from Acros |
| MDI | DOW Isonate OP50, from Dow |
| DBTL | Dibutyltin dilaurate, from Aldrich |
| C62 | Carbinol terminated polydimethylsiloxane with a molecular weight MW of 1670, from Dow Corning |
| C16 | Carbinol terminated polydimethylsiloxane having Mn of 920 to 924, from Gelest, Product DMS-C16 |
| PEG400 | Polyethylene glycol having Mw of 400, from TCI |
| Pluronic L-31 | Poly(ethylene glycol)-block-poly(propylene glycol)-block-poly(ethylene glycol) having Mw of ~1100, from Aldrich |
| Pluronic L-35 | Poly(ethylene glycol)-block-poly(propylene glycol)-block-poly(ethylene glycol) having Mw of ~1900, from Aldrich |
| PEG-ran-PPG 2500 | Poly(ethylene glycol-ran-propylene glycol) having Mw of ~2500, from Aldrich |
| DBTL | Dibutyltin dilaureate, from Sigma Aldrich |
| BHT | Butyl Hydroxy Toluene, from Sigma Aldrich |
| NMR | Nuclear Magnetic Resonance |
| ml | Milliliters |
| ° C. | Degrees Celsius |
| g | Gram |
| mg | Milligrams |
| Mn | Number average molecular weight determined by NMR |
| MW | Weight average molecular weight |
| NMR | Nuclear magnetic resonance |
| DMDO | 1,8-Dimercapto-3,6-dioxaoctane, from Aldrich |
| Tetrathiol | Pentaerythritol tetra(3-mercaptopropionate), from Aldrich |
| XX-3035 | Trimethylsiloxy terminated dimethylsiloxane-methylmercaptopropylsiloxane copolymer with a SH content of 0.35 mol/100 g, made in the lab and analyzed by $^{29}$Si and $^1$H NMR. |
| SMS 142 | Trimethylsiloxy terminated dimethylsiloxane-methylmercaptopropylsiloxane copolymer with a SH content of 0.16 mol/100 g, purchased from Gelest, Inc. |
| SMS 042 | Trimethylsiloxy terminated dimethylsiloxane-methylmercaptopropylsiloxane copolymer with a SH content of 0.05 mol/100 g, purchased from Gelest, Inc. |
| 26298-125 SH crosslinker | Trimethylsiloxy terminated dimethylsiloxane-methylmercaptopropylsiloxane copolymer with a SH content of 0.16 mol/100 g, made in the lab and analyzed by $^{29}$Si and $^1$H NMR. |
| Darocur 1173 | 2-Hydroxy-2-methyl-1-phenyl-propan-1-one |
| N/A | Not available (not measured) |

Example 1

General Procedure 1 for Preparing Copolymers with HDI or MDI, a Polyorganosiloxane, a Polyethylene Glycol, and DA A 500 ml 4 neck flask was placed into a temperature controlled heating block and fitted with mechanical stirrer, thermometer, dropping funnel and reflux condenser, and purged with dry nitrogen, then placed under nitrogen blanket.
1) The flask was charged with an isocyanate compound
2) An Endblocker, a polyorganosiloxane, a polyethylene glycol and solvent were charged to the dropping funnel and added to the flask which were stirred for about 10 min until the exotherm temperature increase subsided.
3) Optionally, a catalyst (DBTL) and solvent was added and the mixture heated for 4 hours at 60° C.
4) 3-5 wt. % EtOH was added to the mixture in the flask, which was then heated to reflux for 1- 2 hours.
5) The mixture in the flask was cooled to room temperature and filtered through a 0.45 micron filter using Celite® 545 filter aid. The filtrate was transferred into a round flask and volatiles removed with a rotary evaporator (90° C., 1 mbar).

Example 2

General Procedure 2 for Preparing Copolymers with HDI or MDI, a Polyorganosiloxane, a Polyethylene Glycol, and an Allyl Ether A 500 ml 4 neck flask was placed into a temperature controlled heating block and fitted with mechanical stirrer, thermometer, dropping funnel and reflux condenser, purged with dry nitrogen, and placed under nitrogen blanket.
1) The flask was charged with an isocyanate compound, an endblocker and DBTL as catalyst, which were mixed to form a mixture.
2) The mixture was stirred and heated at 60° C. for 1 hour, and the progress of the reaction followed by FTIR.
3) The reaction was cooled to room temperature of 15° C. to 30° C. and solvent added.
4) A polyorganosiloxane, a polyethylene glycol and solvent were charged to the dropping funnel and added to the mixture in the flask, which was then heated for 4 hours at 60° C.
5) 3-5 wt. % EtOH was added to the mixture in the flask, which was then heated to reflux for 1-2 hours.
6) The mixture in the flask was cooled to room temperature and filtered through a 0.45 micron filter using Celite® 545 filter aid. The filtrate was transferred into a round flask and volatiles removed with a rotary evaporator (90° C., 1 mbar).

Example 3

General Procedure 3 for Preparing Copolymers of HDI a Polyorganosiloxane, a Polyethylene Glycol and an Acrylate A 500 ml 4 neck flask was placed into a temperature controlled heating block and fitted with mechanical stirrer, thermometer, dropping funnel and reflux condenser, purged with dry nitrogen, and placed under nitrogen blanket
1) The flask was charged with an isocyanate compound, an endblocker, DBTL as catalyst and BHT as radical inhibitor which were stirred to form a mixture.

2) The mixture was stirred and heated at 45-50° C. for 1 hour, and the progress of the reaction followed by FTIR.
3) After 1 hour the reaction was cooled to room temperature of 15° C. to 25° C. and solvent added.
4) A polyorganosiloxane, a polyethylene glycol and a solvent were charged to the dropping funnel and added to the mixture in the flask, which was then heated for 4 hours at 45-50° C.
5) When the colorimetric test was negative, 3-5 wt. % EtOH was added and the reaction heated for 1-2 hours at 45-50° C.6) The mixture in the flask was cooled to room temperature and filtered through a 0.45 micron filter using Celite® 545 filter aid. The filtrate was transferred into a round flask and volatiles removed with a rotary evaporator (45-50° C., 1 mbar).
6) The mixture in the flask was cooled to room temperature and filtered through a 0.45 micron filter using Celite® 545 filter aid. The filtrate was transferred into a round flask and volatiles removed with a rotary evaporator (90° C., 1 mbar).

Samples of copolymers were prepared according to general procedures in examples 1, 2, and 3 above using starting materials and conditions shown in Table 2. Table 2 lists the amounts of each starting material used and the procedure followed to make these copolymers.

TABLE 2

Copolymer Synthesis

| Copolymer | Endblocker Type; wt. (g) | Siloxane Diol Type, wt., (g) | Diisocyanate Type, wt. (g) | Solvent Type; wt. (g) | General Procedures & Deviations |
|---|---|---|---|---|---|
| $HDI_{15.6}(C62)_{14.6}PTA_2$ | PTA: 4.2 | C62: 152.8 | HDI: 15.8 | EtAc: 80 | 2, no PEG |
| $HDI_{14.2}(C62)_{11.4}(PEG400)_{2.8}PTA_{0.5}APMA_{1.5}$ | PTA: 1.1 APMA: 2.3 | C62: 124.9 PEG400: 7.3 | HDI: 16.2 | EtAc: 80 | 3 |
| $HDI_{15.4}(C62)_{14.4}PTA_{0.5}APMA_{1.5}$ | PTA: 1.1 APMA: 2.4 | C62: 159.7 | HDI: 16.6 | EtAc: 120 | 3, no PEG |
| $HDI_{13.7}(C62)_{12.7}TPDA_2$ | TPDA: 3.6 | C62: 180.1 | HDI: 18.7 | EtAc: 80 | 2, no PEG |
| $HDI_{13.9}(C62)_{12.0}PTAE_2$ | PTAE: 3.5 | C62: 149.6 | HDI: 15.5 | EtAc: 80 | 2, no PEG |
| $HDI_{13.5}(C16)_{12.5}DA_2$ | DA: 3.9 | C16: 233.5 | HDI: 44.7 | EtAc: 200 | 1, no PEG |
| $HDI_{13.4}(C62)_{8.4}(PEG400)_4DA_2$ | DA: 1.4 | C62: 84.6 PEG400: 9.9 | HDI: 13.1 | EtAc: 80 | 1, catalyst |
| $HDI_{14.4}(C62)_{6.5}(PEG400)_{6.5}DA_2$ | DA, 1.2 | C62, 67.4 PEG400, 15.8 | HDI, 13.9 | EtAc: 80 | 1, catalyst |
| $HDI_{14}(C62)_{10.2}(PEG400)_{2.5}DA_2$ | DA: 1.4 | C62: 122.1 PEG400: 7.1 | HDI: 15.1 | EtAc: 80 | 1, catalyst |
| $HDI_{14.4}(C62)_{12}(PEG400)_{1.4}DA_2$ | DA: 1.0 | C62: 98.0 PEG400: 2.9 | HDI: 11.4 | EtAc: 80 | 1, catalyst |
| $HDI_{13.9}(C62)_{8.6}(PEG400)_{4.3}TPDA_2$ | TPDA: 2.9 | C62: 96.2 PEG400: 11.3 | HDI: 15.0 | EtAc: 80 | 2 |
| $MDI_{8.2}(C62)_{5.8}(PEG400)_{1.4}TPDA_2$ | TPDA: 4.1 | C62: 93.2 PEG400: 5.5 | MDI: 19.0 | EtAc: 150 | 2 |
| $MDI_{13.4}(C62)_{10}(PEG400)_{2.4}TPDA_2$ | TPDA: 2.4 | C62: 96.7 PEG400: 5.7 | MDI: 18.6 | EtAc: 150 | 2 |
| $MDI_{13.9}(C62)_{8.6}(PEG400)_{4.3}TPDA_2$ | TPDA: 2.6 | C62: 87.0 PEG400: 10.2 | MDI: 20.1 | EtAc: 150 | 2 |
| $HDI_{14}(C62)_{6.5}(PEG400)_{6.5}TPDA_2$ | TPDA: 3.2 | C62, 79.8 PEG400, 18.7 | HDI: 16.6 | EtAc: 80 | 2 |
| $MDI_{14.2}(C62)_{6.6}(PEG400)_{6.6}TPDA_2$ | TPDA: 2.8 | C62: 71.7 PEG400: 16.8 | MDI: 22.1 | EtAc: 150 | 2 |
| $HDI_{14}(C62)_{6.5}(PEG400)_{6.5}TPDA_2$ | TPDA | C62 PEG400 | HDI | EtAc | 2 |
| $HDI_{14.5}(C62)_9(PEG400)_{4.5}PTAE_2$ | PTAE: 3.5 | C62: 97.2 PEG400: 11.4 | HDI: 15.1 | EtAc: 80 | 2 |
| $MDI_{8.4}(C62)_{6.1}(PEG400)_{1.34}PTAE_2$ | PTAE: 4.4 | C62: 85.0 PEG400: 5.0 | MDI: 17.3 | EtAc: 150 | 2 |
| $MDI_{13.8}(C62)_{10.4}(PEG400)_{2.4}PTAE_2$ | PTAE: 3.1 | C62: 104.8 PEG400: 6.1 | MDI: 20.2 | EtAc: 150 | 2 |
| $MDI_{14.25}(C62)_{9.8}(PEG400)_{4.3}PTAE_2$ | PTAE: 3.1 | C62: 97.0 PEG400: 10.3 | MDI: 20.4 | EtAc: 150 | 2 |
| $MDI_{13.9}(C62)_{11.4}(PEG200)_{2.5}TPDA_2$ | TPDA: 2.7 | C62: 118.8 PEG200: 3.1 | MDI: 20.8 | EtAc: 150 | 2 |
| $MDI_{14}(C62)_{6.5}(PEG200)_{6.5}TPDA_2$ | TPDA: 2.7 | C62: 67.4 PEG200: 7.9 | MDI: 20.8 | EtAc: 150 | 2 |
| $MDI_{8.8}(C62)_{3.9}(PEG200)_{3.9}TPDA_2$ | TPDA: 5.1 | C62: 77.2 PEG200: 18.1 | MDI: 23.8 | EtAc: 150 | 2 |
| $MDI_{14.6}(C62)_{11.4}(PEG-PPG-PEG1100)_{2.5}TPDA_2$ | TPDA: 2.4 | C62: 106.0 Pluronic L31: 13.7 | MDI: 18.7 | EtAc: 150 | 2 |
| $HDI_{13.6}(C62)_{11.1}(PEG-PPG-PEG1100)_{2.1}TPDA_2$ | TPDA: 2.6 | C62: 114.2 Pluronic L31: 14.8 | HDI: 13.6 | EtAc: 100 | 2 |
| $HDI_{8.56}(C62)_{6.3}(PEG-PPG-PEG1100)_{1.26}TPDA_2$ | TPDA: 4.1 | C62: 102.0 Pluronic L31: 13.3 | HDI: 12.7 | EtAc: 100 | 2 |
| $MDI_{14.2}(C62)_{12.5}(PEG-PPG-PEG1900)_{1.4}TPDA_2$ | TPDA: 2.1 | C62: 102.3 Pluronic L35: 12.6 | MDI: 16.7 | EtAc: 150 | 2 |
| $HDI_{14.2}(C62)_{12.5}(PEG-PPG-PEG1900)_{1.4}TPDA_2$ | TPDA: 2.2 | C62: 102.7 Pluronic L35: 12.7 | HDI: 11.2 | EtAc: 100 | 2 |
| $HDI_{8.2}(C62)_{6.9}(PEG-PPG-PEG1900)_{0.77}TPDA_2$ | TPDA: 3.8 | C62 Pluronic L35: 12.7 | HDI: 11.8 | EtAc: 100 | 2 |

TABLE 2-continued

Copolymer Synthesis

| Copolymer | Endblocker Type; wt. (g) | Siloxane Diol Type, wt., (g) | Diisocyanate Type, wt. (g) | Solvent Type; wt. (g) | General Procedures & Deviations |
|---|---|---|---|---|---|
| $MDI_{13.4}(C62)_{12}(PEG\text{-}PPG\text{-}ran2500)_1 TPDA_2$ | TPDA: 2.1 | C62: 101.0<br>PEG-PPG-ran2500: 12.3 | MDI: 10.93 | EtAc: 100 | 2 |
| $HDI_{13.8}(C62)_{12.4}(PEG\text{-}PPG\text{-}ran2500)_{1.01} TPDA_2$ | TPDA: 2.4 | C62: 118.2<br>PEG-PPG-ran2500: 14.4 | HDI: 12.7 | EtAc: 100 | 2 |

In Table 2, copolymers indicating catalyst was used were made with 500 ppm DBTL as Catalyst, and 300 ppm BHT as a Radical Inhibitor.

Table 3 shows the characterization results of certain copolymer samples in in Table 2. The number average molecular weight (Mn) of each copolymer was measured by NMR. $^1$H-NMR analysis (in ppm, solvent $CDCl_3$) analysis $^{13}$C-NMR analysis (solvent $CDCl_3$) were performed.

TABLE 3

Copolymer Characterization Results

| Copolymer | Molecular Weight (Mn) (g/mol) | $^1$H-NMR analysis | $^{13}$C-NMR analysis |
|---|---|---|---|
| $HDI_{14.4}(C62)_{6.5}(PEG400)_{6.5}DA_2$ | 16250 | Olefinic (5.83-5.74, 5.18-5.14 ppm), NH (4.88, 4.37), —CH$_2$OOC (4.20-4.18), —CH$_2$—CH═CH$_2$ (3.85-3.83), —CH$_2$—OCH$_2$CH$_2$O—CH$_2$—, —CH$_2$—O—C$_3$H$_6$—Si (3.71-3.58), —O—CH$_2$—C$_3$H$_6$—Si (3.42-3.38), —CH$_2$—NHCO (3.16-3.11), —CH$_2$— (1.64-1.56, 1.49-1.45, 1.33-1.30), —CH$_2$—Si (0.53-0.48), Si—CH$_3$ (0.10-0.00). | N—C═O—NH, NH—CO—O (158.13, 156.43), —HC═CH$_2$ (134.25), —HC═CH$_2$ (116.48), O—CH$_2$—C$_2$H$_4$—Si (74.02), —(O—CH$_2$—CH$_2$)$_m$—O—(70.55-70.45), —CH$_2$—(O—C$_2$H$_4$)$_n$—O—CH$_2$— (69.60), ═C—CH$_2$—O—CO—NH— OCO—CH$_2$—CH$_2$—(O—C$_2$H$_4$)$_n$—O—CH$_2$— —OCO—CH$_2$—CH$_2$—O—C$_3$H$_6$—Si (63.96), —OC—O—CH$_2$—CH$_2$—O—C$_3$H$_6$—Si (61.86-61.50), —CH$_2$—HC═CH$_2$ (49.30), —C$_4$H$_8$—CH$_2$—NH—C═O—O (40.74, 40.44), —CH$_2$— (30.04, 29.76, 26.21), —CH$_2$—O—Si (23.25), Si—CH$_3$— (13.98), Si—CH$_3$ (1.08-0.22). |
| $HDI_{13.5}(C16)_{12.5}DA_2$ | 14000 | Olefinic (5.83-5.73, 5.19-5.14 ppm), NH (4.63, 4.43), —CH$_2$OOC (3.99-3.96), —CH$_2$—CH═CH$_2$ (3.84-3.82), —CH$_2$—OH (3.60-3.56), —CH$_2$—NHCO (3.20-3.11), —CH$_2$— (1.64-1.56, 1.49-1.45, 1.33-1.30), —CH$_2$—Si (0.54-0.49), Si—CH$_3$ (0.08-0.03). | N—C═O—NH, NH—CO—O (158.57, 157.31), —HC═CH$_2$ (134.42), —HC═CH$_2$ (116.93), —CH$_2$O—CO (67.45), N—CH$_2$—CH$_2$ (49.52), —CH$_2$—NH—C═O—O CH$_2$—NH—C═O—N (41.17, 40.79), —CH$_2$—(30.69, 30.43, 26.58), —CH$_2$—(23.27, Si—CH$_2$— (14.26), Si—CH$_3$ (1.45-0.46). |
| $HDI_{13.7}(C62)_{12.7}TPDA_2$ | 24420 | Olefinic (5.89-5.81, 5.25-5.11 ppm), NH (4.75, 4.62, 4.47, 4.36), —CH$_2$OOC (4.20-4.18), COO—CH$_2$—C(Et)— (4.01), {Vi-CH$_2$}$_2$—O— (3.94-3.92), —CH$_2$—C$_3$H$_6$—Si (3.61-3.58), —O—CH$_2$—C$_3$H$_6$—Si (3.43-3.39), —CH$_2$—NHCO (3.17-3.12), —CH$_2$— (1.64-1.56, 1.49-1.46, 1.33-1.29), C—CH$_2$—Si (0.53-0.49), Si—CH$_3$ (0.07-0.03). | NH—CO—O (156.39), —HC═CH$_2$ (135.04), —HC═CH$_2$ (116.15), O—CH$_2$—C$_2$H$_4$—Si CH$_2$—O—C$_2$H$_4$—Si (74.02, 68.97), Vi-CH$_2$—O (72.18), Allyl-O—CH$_2$— (70.38), —OC—O—CH$_2$—O—C$_3$H$_6$—Si (63.84), ═C—CH$_2$—O—CO—NH— (61.72), Et—C═ (42.44), —C$_4$H$_8$—CH$_2$—NH—C═O—O (40.75), —CH$_2$— (29.79, 26.20), CH$_2$—CH$_2$—C═ (23.35), —CH$_2$— (14.00), CH$_3$—CH$_2$—C═ (7.79), Si—CH$_3$ (1.08-0.95, 0.02). |
| $HDI_{13.9}(C62)_{12.0}PTAE_2$ | 24900 | Olefinic (5.89-5.82, 5.26-5.10 ppm), NH (4.75, 4.62, 4.48, 4.37), —CH$_2$OOC (4.20-4.18), COO—CH$_2$—O— (4.14), {Vi-CH$_2$}$_3$—O— (3.94-3.92), —CH$_2$—C$_3$H$_6$—Si (3.61-3.58), —O—CH$_2$—C$_3$H$_6$—Si {Allyl-O—CH$_2$}$_3$—C— (3.42-3.39), —CH$_2$—NHCO (3.17-3.12) | NH—CO—O (156.40), —HC═CH$_2$ (134.98), —HC═CH$_2$ (116.14), O—CH$_2$—C$_2$H$_4$—Si CH$_2$—O—C$_2$H$_4$—Si (74.04, 68.97), Vi-CH$_2$—O (72.22), Allyl-O—CH$_2$— (69.1), —OC—O—CH$_2$—O—C$_3$H$_6$—Si (63.86), ═C—CH$_2$—O—CO—NH— (61.73), Et—C═ (42.62), —C$_4$H$_8$—CH$_2$—NH—C═O—O (40.76), —CH$_2$— (29.80, 26.21), CH$_3$—CH$_2$—C═ |

TABLE 3-continued

Copolymer Characterization Results

| Copolymer | Molecular Weight (Mn) (g/mol) | $^1$H-NMR analysis | $^{13}$C-NMR analysis |
|---|---|---|---|
| HDI$_{14}$(C62)$_{6.5}$(PEG400)$_{6.5}$TPDA$_2$ | 16500 | Olefinic (5.88-5.80, 5.25-5.10 ppm), NH (4.91, 4.36), —CH$_2$OOC (4.19-4.17), COO—CH$_2$—C(Et)— (4.01), {Vi-CH$_2$}$_3$—O— (3.93-3.90), —CH$_2$—OCH$_2$CH$_2$O—CH$_2$— (3.71-3.58), —O—CH$_2$—C$_3$H$_6$—Si (3.42-3.38), {Allyl-O—CH$_2$}$_2$— (3.29), —CH$_2$—NHCO (3.16-3.11), —CH$_2$— (1.63-1.55, 1.48-1.45, 1.32-1.29), C—CH$_2$—CH$_3$ (0.86-0.82), C—CH$_3$—Si (0.52-0.48), Si—CH$_3$ (0.08-0.03). | (23.35), —CH$_2$—CH$_2$—O—Si (23.28), Si—CH$_2$— (14.00), CH$_3$—CH$_2$—C= (7.79), Si—CH$_3$ (1.09-0.95, 0.03), NH—CO—O (158.76), —HC=CH$_2$ (135.27), —HC=CH$_2$ (116.37), —O—CH$_2$—C$_2$H$_4$—Si CH$_2$—O—C$_3$H$_6$—Si (74.14, 70.72), Vi-CH$_2$—O (72.37), —(O—CH$_2$—CH$_2$)$_n$—O— (70.72), Allyl-O—CH$_2$— (69.80), —CH$_2$—(O—C$_2$H$_4$)$_n$—O—CH$_2$— (69.19), —CH$_2$—CH$_2$—(O—C$_2$H$_4$)$_n$—O—CH$_2$—CH$_2$— —OC—O—CH$_2$—(O—C$_3$H$_6$—Si (63.89), =C—CH$_2$—O—CO—NH— (61.69), Et—C= (42.65), —C$_4$H$_8$—CH$_2$—NH—C=O (41.94, 41.56), —CH$_2$— (30.69, 26.47, 26.58), —CH$_2$—O—Si (23.51), CH$_3$—CH$_2$—C= (23.09), Si—CH$_3$— (14.23). |
| HDI$_{14.5}$(C62)$_9$(PEG400)$_{4.5}$PTAE$_2$ | 20200 | Olefinic (5.89-5.79, 5.24-5.09 ppm), NH (4.86, 4.74, 4.61, 4.35), —CH$_2$OOC (4.19-4.17), COO—CH$_2$—C— (4.13), {Vi-CH$_2$}$_3$—O— (3.92-3.90), —CH$_2$—OCH$_2$CH$_2$O—CH$_2$— —CH$_2$—O—C$_3$H$_6$—Si (3.67-3.57), —O—CH$_2$—C$_3$H$_6$—Si {Allyl-O—CH$_2$}$_2$—C— (3.42-3.38), —CH$_2$—NHCO (3.16-3.11), —CH$_2$— (1.63-1.55, 1.48-1.45, 1.32-1.29), C—CH$_2$—Si (0.52-0.48), Si—CH$_3$ (0.10-0.03). | CH$_3$—CH$_2$—C= (7.79), Si—CH$_3$ (1.16-0.27). NH—CO—O (156.40), —HC=CH$_2$ (134.94), —HC=CH$_2$ (116.11), O—CH$_2$—C$_2$H$_4$—Si (73.97), Vi-CH$_2$—O (72.18), —(O—CH$_2$—CH$_2$)$_n$—O— —CH$_2$—(O—C$_2$H$_4$)$_n$—O—CH$_2$— (70.47-70.41, 68.92), Allyl-O—CH$_2$— (69.56), CH$_2$—O—C$_3$H$_6$—Si (68.92), —CH$_2$—CH$_2$—(O—C$_2$H$_4$)$_n$—O—CH$_2$—CH$_2$— (63.78), —OC—CH$_2$—O—CH$_2$—O—C$_3$H$_6$—Si (63.66), =C—CH$_2$—O—CO—NH— (61.63), Et—C= (44.59), —C$_4$H$_8$—CH$_2$—NH—C=O—O (40.71), —CH$_2$— (29.76, 26.20, 26.17), CH$_3$—CH$_2$—C= (23.31), Si—CH$_2$— (13.97), Si—CH$_3$ (1.29-0.01). |
| HDI$_{8.56}$(C62)$_{6.3}$(PEG-PPG-PEG1100)$_{1.26}$TPDA$_2$ | 14000 | Olefinic (5.90-5.81, 5.25-5.10 ppm), NH (4.82, 4.37), —CH$_2$OOC (4.20-4.17), COO—CH$_2$—C(Et)— (4.01), {Vi-CH$_2$}$_3$—O— (3.92-3.91), —CH$_2$—OCH$_2$C(Me)HO—CH$_2$— —CH$_2$—O—C$_3$H$_6$—Si {Allyl}$_2$—O—CH$_2$—C(Et)—CH$_2$—O (3.65-3.48), —O—CH$_2$—C$_3$H$_6$—Si (3.42-3.38), {Allyl-O—CH$_2$}$_2$— (3.30), —CH$_2$—NHCO (3.16-3.11), —CH$_2$— (1.65-1.59, 1.56-1.45, 1.31-1.29), 1.13-1.11(—CHMe—O), | NH—CO—O (156.64, 156.40), —HC=CH$_2$ (135.05), —HC=CH$_2$ (116.17), —C(Me)H— (77.34, 77.02, 76.70), —CH$_2$—C(Me)H— (75.46, 75.31, 75.27, 75.09), —O—CH$_2$—C$_2$H$_4$—Si (74.04), Vi-CH$_2$—O (72.19), —(O—CH$_2$—CH$_2$)$_n$—O— (70.52, 70.38), Allyl-O—CH$_2$— (69.60), CH$_2$—O—C$_3$H$_6$—Si—CH$_2$—(O—C$_2$H$_4$)$_n$—O—CH$_2$— (68.96), =C—CH$_2$—O—CO—NH— (65.14), —CH$_2$—(O—C$_3$H$_6$—Si—O—CH$_2$—CH$_2$— (63.86), —OC—CH$_2$—O—CH$_2$—O—C$_3$H$_6$—Si (61.73), Et—C= (42.44), |

TABLE 3-continued

Copolymer Characterization Results

| Copolymer | Molecular Weight (Mn) (g/mol) | $^1$H-NMR analysis | $^{13}$C-NMR analysis |
|---|---|---|---|
| HDI$_{15.6}$(C62)$_{14.6}$PTA$_2$ | 28100 | C—CH$_2$—CH$_3$ (0.86-0.82), C—CH$_2$—Si (0.52-0.48), Si—CH$_3$ (0.09-0.02). | —C$_4$H$_8$—CH$_2$—NH—C═O—O (40.76), —CH$_2$— (29.80, 26.21), CH$_3$—CH$_2$—C═ (23.35), —CH$_2$—CH$_2$—O—Si (23.28), Me (17.28, 17.27, 17.24, 17.13), Si—CH$_2$— (13.99), CH$_3$—C═ (7.55), Si—CH$_3$ (1.09-0.03). |
| HDI$_{14.2}$(C62)$_{11.4}$(PEG400)$_{2.8}$PTA$_{0.5}$APMA$_{1.5}$ | 21800 | Olefinic (6.43-6.35, 6.13-6.07, 5.88-5.81 ppm), NH (4.74), —O—CH$_2$OOC —CH$_2$OOC (4.29-4.17), —CH$_2$—OH (3.80-3.77), CH$_2$—CH$_2$—OH (3.61-3.58), —CH$_2$—O—C$_3$H$_6$—Si (3.60-3.58), —O—CH$_2$—C$_3$H$_6$—Si (3.42-3.39), —CH$_2$—NHCO (3.17-3.12), —CH$_2$— (1.64-1.58, 1.49-1.44, 1.33-1.29), —CH$_2$—Si (0.53-0.49), Si—CH$_3$ (0.07-0.03). | Vi-CO—O— (165.40), NH—CO—O (156.40), —HC═CH$_2$ (131.63, 131.16), —HC═CH$_2$ (127.90, 127.56), O—CH$_2$—C$_2$H$_4$—Si CH$_2$—O—C$_3$H$_6$—Si (74.02, 68.97), CH$_2$—CH$_2$—O—C$_3$H$_6$—Si (63.94), —C—(CH$_2$)$_3$—O (62.57), ═C—CH$_2$—O—CO—NH— (61.71), C$_4$H$_8$—CH$_2$—NH—C═O—O (40.75), —C═ (39.93),), —CH$_2$— (29.79, 26.20), —CH$_2$—CH$_2$—O—Si (23.28), Si—CH$_2$— (14.09), Si—CH$_3$ (1.08-0.02). |
| HDI$_{14.2}$(C62)$_{11.4}$(PEG400)$_{2.8}$PTA$_{0.5}$APMA$_{1.5}$ | | Olefinic (6.44-6.37, 6.15-6.06, 5.88-5.83, 5.59-5.58 ppm), NH (4.86-4.74), —O—CH$_2$OOC CH$_2$OOC (4.29-4.16), —CH$_2$—OH (3.80-3.77), —CH$_2$—OCH$_2$CH$_2$O—CH$_2$—, —O—CH$_2$—C$_3$H$_6$—Si (3.67-3.58), —O—CH$_2$—C$_3$H$_6$—Si (3.42-3.38),), —O—CH$_2$—C$_3$H$_6$—Si (3.43-3.39), —CH$_2$—NHCO (3.17-3.12), —CH$_2$— (1.64-1.56, 1.49-1.46, 1.33-1.29), —CH$_2$—Si (0.53-0.49), Si—CH$_3$ (0.07-0.03). | Vi-CO—O— (165.51), NH—CO—O (156.39), —HC═CH$_2$ (131.63, 131.16), HC═CH$_2$ H$_2$C═CMe (127.89, 127.75, 127.55, 126.15), O—CH$_2$—C$_3$H$_4$—Si (74.02) —(O—CH$_2$—CH$_2$)$_n$—O— —CH$_2$—(O—C$_2$H$_4$)$_n$—O—CH$_2$— CH$_2$—O—C$_3$H$_6$—Si (70.53-70.44, 68.95), —HC—O—CO—NH— (69.59), CH$_2$—CH$_2$—O—C$_3$H$_6$—Si (63.84, 62.72), —C—(CH$_2$)$_3$—O (63.72), ═C—CH$_2$—O—CO—NH— (62.57), C$_4$H$_8$—CH$_2$—NH—C═O—O (61.71), —C═ (40.59),), —CH$_2$— (40.75), —CH$_2$— (29.79, 26.20), —CH$_2$—CH$_2$—O—Si (23.27), Si—CH$_2$— (13.99), Si—CH$_3$ (1.09-0.02). |
| MDI$_{14.2}$(C62)$_{6.6}$(PEG400)$_{6.6}$TPDA$_2$ | 17900 | Aromatic (7.76-7.74, 7.35-7.22, 7.11-7.03, 6.74-6.37 ppm), olefinic (5.89-5.80, 5.25-5.10), —CH$_2$OOC (4.28-4.25), COO—CH$_2$—C(Et)— (4.12), {Vi-CH$_2$}$_2$—O— (3.93-3.90), Ph—CH$_2$—Ph (3.89, 3.86), —CH$_2$—OCH$_2$CH$_2$O—CH$_2$—, —O—CH$_2$—C$_3$H$_6$—Si (3.69-3.58), —O—CH$_2$—C$_3$H$_6$—Si (3.45-3.41), {Allyl-O—CH$_2$}$_2$ (3.33), —CH$_2$ (1.65-1.58), CH$_3$—CH$_2$(1.48-1.42), | NH—CO—O (153.62, -153.48), —HC═CH$_2$ (136.22-135.96), —HC═CH$_2$ (116.36), Aromatic (134.96, 130.44, 129.32, 129.07, 129.04, 127.37, 124.70, 119.06, 118.86), O—CH$_2$—C$_3$H$_4$—Si CH$_2$—O—C$_3$H$_6$—Si (74.10, 70.72), Vi-CH$_2$—O (72.25), —CH$_2$—(O—CH$_2$—CH$_2$)$_n$—O (70.48), —CH$_2$—(O—C$_2$H$_4$)$_n$—O—CH$_2$ (69.38), Allyl-O—CH$_2$— (68.79), —CH$_2$—CH$_2$—(O—C$_2$H$_4$)$_n$—O—CH$_2$—CH$_2$—, —OC—O—CH$_2$—CH$_2$—O—C$_3$H$_6$—Si (64.37- |

TABLE 3-continued

Copolymer Characterization Results

| Copolymer | Molecular Weight (Mn) (g/mol) | $^1$H-NMR analysis | $^{13}$C-NMR analysis |
|---|---|---|---|
| | | C—CH$_2$—CH$_3$ (0.884-0.84), C—CH$_2$—Si (0.52-0.49), Si—CH$_3$ (0.07-0.03). | 64.00), =C—CH$_2$—O—CO—NH— (61.76), Et—C= (42.47), —C$_4$H$_8$—CH$_2$—NH—C=O—O (40.51), Ph—CH$_2$—Ph— (37.07, 37.03), —CH$_2$—CH$_2$—O—Si (23.32), CH$_3$—CH$_2$—C= (22.95), Si—CH$_2$— (14.09), CH$_3$—CH$_2$—C= (7.58), Si—CH$_3$ (1.14-0.08). |
| MDI$_{8.4}$(C62)$_{6.1}$(PEG400)$_{1.34}$PTAE$_2$ | 13550 | Aromatic (7.72-7.71, 7.29-7.22, 7.08-7.03, 6.71-6.36 ppm), olefinic (5.89-5.79, 5.25-5.19), —CH$_2$OOC COO—CH$_2$—C— (4.30-4.24), {Vi-CH$_2$}$_3$—O— (3.93-3.92), Ph—CH$_2$—Ph (3.89, 3.86), —CH$_2$—OCH$_2$CH$_2$O—CH$_2$— —CH$_2$—O—C$_3$H$_6$—Si (3.66-3.60), —O—CH$_2$—C$_3$H$_6$—Si {Allyl-O—CH$_2$}$_3$— (3.45-3.41), —CH$_2$-(1.48-1.42), CH$_3$—CH$_2$-(1.48-1.42), C—CH$_2$—Si (0.54-0.49), Si—CH$_3$ (0.09-0.03). | NH—CO—O (153.96, - 153.47), —HC=CH$_2$ (136.45-135.65), —HC=CH$_2$ (116.34), Aromatic (134.91, 130.43, 129.33, 129.08, 127.40, 124.71, 119.08, 118.86), O—CH$_2$—C$_2$H$_4$—Si (74.10, 70.72), Vi-CH$_2$—O (72.28), —(O—CH$_2$—CH$_2$)$_n$—O—CH$_2$—O—C$_3$H$_6$—Si), —CH$_2$—(O—C$_2$H$_4$)$_n$—O—CH$_2$—, —CH$_2$—(O—C$_2$H$_4$)$_n$—O—CH$_2$—, Allyl-O—CH$_2$— (70.46, 69.38, 69.15. 69.79, 68.75), CH$_2$—CH$_2$—(O—C$_2$H$_4$)$_n$—O—CH$_2$—CH$_2$— —OC—O—CH$_2$—CH$_2$—O—C$_3$H$_6$—Si (64.37-64.18), =C—CH$_2$—O—CO—NH— (61.75), —C= (44.65), —C$_4$H$_8$—CH$_2$—NH—C=O—O (40.52), Ph—CH$_2$—Ph— (37.10, 37.03), —CH$_2$—CH$_2$—O—Si (23.32), Si—CH$_2$— (14.06), Si—CH$_3$ (1.14-0.08). |

Example 4

Composition including Copolymer (HDI$_{14.4}$(C62)$_{6.5}$(PEG400)$_{6.5}$DA$_2$) and Different SH Crosslinkers A 2 g sample of the Copolymer (HDI$_{14.4}$(C62)$_{6.5}$(PEG400)$_{6.5}$DA$_2$) was placed in a dental cup and 0.0448 g of the di-functional SH-crosslinker 2,2'-(Ethylenedioxy)diethanethiol (DMDO) was added to achieve a 1:1 SH to vinyl (SH:Vi) ratio. 1 wt % of Darocur 1173 (photoinitiator) was added to the cup and the contents were mixed by hand followed by mixing for 30 seconds at 3000 rpm in a dental mixer. The mixing procedure was repeated twice before the material was allowed to sit on the benchtop for 5 minutes to level out. The mixed material was then cured in a UV chamber for a period of time. The UV-exposed material was subjected to a cup test, described below.

A cup test was a series of screening parameters used to quickly characterize a material. The cup test involved (a) a visual assessment of material appearance, (b) tack to a stainless steel stud, (c) cohesive failure on stainless steel, (d) cohesive failure on plastic dental cup, (e) cohesive failure on nitrile glove, and (f) material hardness. A visual assessment of material appearance (a) was performed by noting the material color, transparency/opacity, and presence of entrapped air bubbles. To assess tack (b), a stainless steel probe (12 mm diameter) was allowed to be in contact with the material surface for 10 seconds under a 152.5 g weight. The tack in terms of Wagner force (lbf) was measured using a Wagner FDIX Force Cell Module. The tack test was repeated in triplicate, avoiding overlap of testing area. (c) After each run of the tack test, the stainless steel probe was visually examined to observe any residue indicating cohesive failure. It was given a qualitative score of "None", "Min-to-no" (minimal to none), "Min" (minimal), "Residue", or "Significant Residue." (d) A test of material cohesive failure to the dental cup was performed by using a metal spatula to gently release the material from the cup. A visual assessment of material residue on the cup surface was categorized into "Pulled clean from cup," "Residue Remaining," "Significant residue remaining," and "did not cure." Subsequently, the material was manipulated between the fingers of a nitrile-gloved hand to assess (e) the cohesive failure on the nitrile glove and (f) the material hardness. Minor and major residue on the glove was noted and the material hardness scored as either "soft," "soft-to-med", "medium", "med-to-hard," or "hard." The results from the cup test of Example 4 are noted in Tables 4.

Additional compositions were prepared as above using the Copolymer but varying SH:Vi ratios, 0.6:1 or 1:1, and SH crosslinkers, di-functional DMDO or TT. A summary of compositions tested is shown in Table 4.

Select compositions were chosen to undergo further testing. To prepare the chosen compositions, a 7.5g sample of the Copolymer (HDI$_{14.4}$(C62)$_{6.5}$(PEG400)$_{6.5}$DA$_2$) was placed in a cup and either 0.2254 g or 0.1352 g of the TT crosslinker was added to achieve a 1:1 or 0.6:1 SH to vinyl ratio, respectively. The photoinitiator Darocur 1173 was added to the cup at 1 wt % and the contents were mixed by hand followed by mixing for 30 seconds at 3000 rpm in a dental mixer. The mixing procedure was repeated twice. The resulting composition was poured onto a polyester sheet and a laminate prepared using a 15 mil thick chase. The laminate was cured in a UV chamber for a period of time. A blue low density polyethylene (LDPE) liner was then rolled over the cured laminate. The resulting laminate was kept overnight at room temperature before it was tested for release, adhesion, and cohesive strength. All test results are summarized in Table 15.

For the release measurement, the release liner was secured in the bottom clamp, and the adhesive coated polyurethane laminate was secured in the top clamp. The clamps were pulled apart at 10 mm/s for 130 mm. The value reported for each strip was the average force (N)/in to pull the release liner from the adhesive coated polyurethane laminate. The data from the first 20 mm and the last 10 mm were discarded, and the data from the remaining 100 mm was averaged. One to three replicates were tested to generate the value reported in the table in Newtons per (linear) inch (N/in). The final reported value is the average of the 1 to 3 test strips (1 inch=25 mm).

For the adhesion measurement, the release liner was removed from the coated test strip, and the test strip was adhered to the frosted side of a 1.5 in×9 in (3.8 cm×23 cm) strip of polycarbonate. With the use of a 5 lb rubber coated roller, the adhesive strip was applied to the polycarbonate with one stroke forward and one stroke back at a rate of 1 in/sec (2.5 cm/sec). The sample was allowed to remain in contact with the polycarbonate for 30 minutes. During the test, the polycarbonate was secured in the bottom clamp, while the adhesive coated polyurethane was secured in the top clamp. As in the release test, the clamps were pulled apart at 10 mm/s for 130 mm. The force to pull the adhesive coated polyurethane (1 in wide) from the polycarbonate was averaged over 100 mm (excluding the first 20 mm and last 10 mm of the 130 mm pull) with the final measurement in Newtons per (linear) inch (N/in). The final reported value was the average of 1 to 3 test strips.

Percent cohesive failure was approximated by visually estimating the amount of adhesive remaining on the polycarbonate after testing for adhesion. When possible a distinction was made between cohesively failing through the adhesive (true cohesive failure) versus transferring from the polyurethane substrate to the polycarbonate (adhesive failure at the substrate). Any adhesive remaining on the polycarbonate was referred to as indicating cohesive failure.

Example 5

Composition Containing Copolymer (HD$_{14.4}$C62$_{12}$PEG400$_{1.4}$DA$_2$) and different SH Crosslinkers Sample compositions containing the Copolymer (HD$_{14.4}$C62$_{12}$PEG400$_{1.4}$DA$_2$) were prepared as described in Example 4, except 0.0308g or 0.0185g of DMDO were used to achieve 1:1 (Composition 2A) and 0.6:1 (Composition 2B) SH:Vi ratios, respectively. Two additional compositions were also prepared as described in Example 4, except 0.0413 g or 0.0248 g of TT were added to achieve 1:1 (Composition 2C) and 0.6:1 (Composition 2D) SH:Vi ratios, respectively.

A cup test of the compositions prepared in Example 5 was completed as described in Example 4 and results summarized in Table 4.

Example 6

Composition Containing Copolymer (HDI$_{14}$(C62)$_{6.5}$(PEG400)$_{6.5}$TPDA$_2$) and Different SH Crosslinkers Sample compositions containing the Copolymer (HDI$_{14}$(C62)$_{6.5}$(PEG400)$_{6.5}$TPDA$_2$) were prepared as described in Example 4, except 0.0443 g or 0.0266 g of DMDO were used to achieve 1:1 (Composition 3A) and 0.6:1 (Composition 3B) SH:Vi ratios, respectively. Two additional compositions were also prepared as described in Example 4, except 0.0594 g or 0.0356 g of TT were added to achieve 1:1 (Composition 3C) and 0.6:1 (Composition 3D) SH:Vi ratios, respectively.

A cup test of the compositions prepared in Example 6 was completed as described in Example 4 and results summarized in Table 4.

Select compositions were chosen to undergo further testing. The compositions were prepared as described in Example 4, except either 0.1661 g of DMDO or 0.1336 g of Tetrathiol were added to achieve a 1:1 SH:Vi (Composition 3A) and a 0.6:1 SH:Vi (Composition 3D), respectively. These compositions underwent release, adhesion, and cohesive failure as described in Example 4 and the results summarized in Table 15.

To prepare compositions for moisture vapor transmission rate (MVTR) measurement, a 5 g sample of the Copolymer $(HD_{14.4}C62_{12}PEG400_{1.4}DA_2L$ was placed in a dental cup and either 0.1107 g of DMDO (Composition 3A) or 0.0891 g Tetrathiol (Composition 3D) was added to achieve a 1:1 and 0.6:1 SH:Vi, respectively. The photoinitiator Darocur 1173 was added at 1 wt % to the cup and the contents were mixed by hand, followed by mixing for 30 seconds at 3000 rpm in a dental mixer. The mixing procedure was repeated twice. The resulting composition was poured onto a collagen sheet and a laminate prepared using a 10 mil thick chase. The laminate was cured in a UV chamber for a period of time. A sheet of Teflon was then rolled over the cured laminate. The resulting laminate was kept overnight at room temperature. MVTR was evaluated as described below.

To perform the MVTR measurement, 50 mm discs were cut from the composition prepared above containing the Copolymer. To a Payne cup (a 25 mL metal container with a 35 mm opening that can be tightly sealed), 10 g of deionized water was added. The disc was placed, adhesive material side down onto the mouth of the Payne cup, completely covering the opening. The remaining Teflon liner was carefully removed and the lid of the Payne cup tightened into place. The entire apparatus was weighed (t=0 hours). The sample cups were incubated at 32° C. or 50% relative humidity for a 24 hour period, in either an upright or inverted configuration. After the incubation, the cups were reweighed (t=24 hours). The moisture vapor transmission rate of the collagen-material composite was calculated by dividing the amount of water evaporated over the open area of the cup (9.90 cm$^2$). The MVTR of the neat prepared material was back calculated by using the following equation:

$$MVTR_{Neat} = \frac{1}{\frac{1}{MVTR_{Composite}} - \frac{1}{MVTR_{Collagen}}}$$

Where $MVTR_{collagen}$ is 1777 g/m$^2$.24 h in the upright configuration and 18006 g/m$^2$.24h in the inverted configuration. Three replicates of both the upright and inverted configuration were tested to generate the value reported in the table in grams per meters squared per 24 hours (g/m$^2$.24 h). The final reported value is the average of the 3 individual cups in Table 16.

Example 7

Composition Using the Copolymer $(HDI_{8.56}(C62)_{6.3}(PEG-PPG-PEG1100)_{1.26}TPDA_2)$ and Different SH Crosslinkers Sample compositions containing the Copolymer $(HDI_{8.56}(C62)_{6.3}(PEG-PPG-PEG1100)_{1.26}TPDA_2)$ were prepared as described in Example 4, except 0.0520 g or 0.0312 g of DMDO were used to achieve 1:1 (Composition 4A) and 0.6:1 (Composition 4B) SH:Vi ratios, respectively. Two additional compositions were also prepared as described in Example 4, except 0.0696 g or 0.0418 g of tetrathiol were added to achieve 1:1 (Composition 4C) and 0.6:1 (Composition 4D) SH:Vi ratios, respectively.

A cup test of the compositions prepared in Example 7 were completed as described in Example 4 and results summarized in Table 4.

Select compositions were chosen to undergo further testing. The compositions were prepared as described in Example 4, except 0.1169 g of DMDO was added to achieve a 0.6:1 SH:Vi (Composition 4B). The chosen compositions underwent release, adhesion, and cohesive failure measurement as described in Example 4 and the results summarized in Table 4.

Compositions for MVTR measurements were prepared as described in Example 6, except 0.0779 g of DMDO (Composition 4B) was added to achieve a 0.6:1 SH:Vi. The prepared composition was evaluated for MVTR as described below and the results summarized in Table 16.

The MVTR measurement was performed and evaluated as described in Example 6.

Overview of Prepared Copolymer Compositions.

|  | Thiol(SH) Crosslinker | |
| --- | --- | --- |
| SH:Vi Ratios | DMDO | Tetrathiol |
| 1:1 | A | C |
| 0.6:1 | B | D |

Additional examples were formulated, cured, and tested. Results are included in the following tables. These were processed and tested as described in Examples 4 to 6.

TABLE 4

Tested formulations based on copolymers in Table 2.

| Acrylate Functional Copolymers | Crosslinker (SH:Vi; Type) | Wagner Force (lbf) | Cohesive Failure | | | Material Hardness | Material Appearance |
| --- | --- | --- | --- | --- | --- | --- | --- |
|  |  |  | Stainless Steel | Dental Cup | Glove |  |  |
| $HDI_{15.6}(C62)_{14.6}PTA_2$ | 1A (1:1 DMDO) | 3.103 | Yes | Yes | Yes | Soft | Opaque White |
|  | 1B (0.6:1 DMDO) | 2.270 | Yes | Yes | Yes | Soft | Opaque White |

TABLE 4-continued

Tested formulations based on copolymers in Table 2.

| Acrylate Functional Copolymers | Crosslinker (SH:Vi; Type) | Wagner Force (lbf) | Cohesive Failure Stainless Steel | Dental Cup | Glove | Material Hardness | Material Appearance |
|---|---|---|---|---|---|---|---|
| | 1C (1:1 TT) | 3.007 | Yes | Yes | Yes | Soft | Opaque White |
| | 1D (0.6:1 TT) | 2.780 | Yes | Yes | Yes | Soft | Opaque White |
| $HDI_{14.2}(C62)_{11.4}(PEG400)_{2.8}PTA_{0.5}APMA_{1.5}$ | 1A (1:1 DMDO) | 3.599 | Slight | No | No | Med-to-hard | Light yellow Transparent |
| | 1B (0.6:1 DMDO) | 3.415 | Slight | No | No | Med-to-hard | Light yellow Transparent |
| | 1C (1:1 TT) | 1.847 | Slight | No | No | Hard | Slightly cloudy |
| | 1D (0.6:1 TT) | 2.022 | No | No | No | Hard | Slightly cloudy |
| $HDI_{15.4}(C62)_{14.4}PTA_{0.5}APMA_{1.5}$ | 1A (1:1 DMDO) | 3.175 | No | No | Slight | Soft | Clear |
| | 1B (0.6:1 DMDO) | 3.148 | Yes | No | Slight | Soft | Clear |
| | 1C (1:1 TT) | 1.924 | No | No | No | Med-to-hard | Slightly cloudy |
| | 1D (0.6:1 TT) | 2.713 | Min-to-no | No | No | Medium | Slightly cloudy |

TABLE 5

Tested formulations based on copolymers in Table 2.

| Non-PEG-Containing Copolymer | Crosslinker (SH:Vi; Type) | Wagner Force (lbf) | Cohesive Failure Stainless Steel | Dental Cup | Glove | Material Hardness | Material Appearance |
|---|---|---|---|---|---|---|---|
| $HDI_{13.7}(C62)_{12.7}TPDA_2$ | 1A (1:1 DMDO) | 3.191 | Yes | Some | Min-to-no | Soft | Light Yellow |
| | 1B (0.6:1 DMDO) | 1.929 | Yes | Yes | Min-to-no | Soft | Faint Yellow |
| | 1C (1:1 TT) | 3.099 | No | No | Min-to-no | Hard | Slightly cloudy |
| | 1D (0.6:1 TT) | 2.902 | Min-to-no | Yes | Yes | Soft-to-med | Slightly cloudy |
| $HDI_{13.9}(C62)_{12.0}PTAE_2$ | 1A (1:1 DMDO) | 2.751 | No | No | No | Med-to-hard | Light yellow |
| | 1B (0.6:1 DMDO) | 2.869 | Yes | Yes | Min-to-no | Medium | Light yellow |
| | 1C (1:1 TT) | 2.278 | No | Yes | No | Med-to-hard | Slightly cloudy |
| | 1D (0.6:1 TT) | 2.678 | Min-to-no | Yes | Min | Medium | Slightly cloudy |
| $HDI_{13.5}(C16)_{12.5}DA_2$ | 1A (1:1 DMDO) | 2.037 | Slight | No | No | Soft-to-med | N/A |
| | 1B (0.6:1 DMDO) | 1.440 | Slight | No | No | Soft-to-med | N/A |
| | 1C (1:1 TT) | Did not cure | N/A | N/A | N/A | N/A | N/A |
| | 1D (0.6:1 TT) | Did not cure | N/A | N/A | N/A | N/A | N/A |

TABLE 6

Tested formulations based on copolymers in Table 2.

| PEG400 Containing Copolymers (DA End-Capped) | Crosslinker (SH:Vi; Type) | Wagner Force (lbf) | Cohesive Failure Stainless Steel | Dental Cup | Glove | Material Hardness | Material Appearance |
|---|---|---|---|---|---|---|---|
| $HDI_{13.4}(C62)_{8.4}(PEG400)_4DA_2$ | 1A (1:1 DMDO) | Did not cure | N/A | N/A | N/A | N/A | N/A |
| | 1B (0.6:1 DMDO) | 2.141 | Slight | No | N/A | N/A | Opaque White |
| | 1C (1:1 TT) | 2.142 | No | No | N/A | N/A | Clear |
| | 1D (0.6:1 TT) | 2.388 | No | No | N/A | N/A | Slightly Yellow |
| $HDI_{14.4}(C62)_{6.5}(PEG400)_{6.5}DA_2$ | 1A (1:1 DMDO) | Did not cure | N/A | N/A | N/A | N/A | N/A |
| | 1B (0.6:1 DMDO) | Did not cure | N/A | N/A | N/A | N/A | N/A |

TABLE 6-continued

Tested formulations based on copolymers in Table 2.

| PEG400 Containing Copolymers (DA End-Capped) | Crosslinker (SH:Vi; Type) | Wagner Force (lbf) | Cohesive Failure Stainless Steel | Dental Cup | Glove | Material Hardness | Material Appearance |
|---|---|---|---|---|---|---|---|
| | 1C (1:1 TT) | 3.611 | No | No | No | Soft-to-med | Faint Yellow |
| | 1D (0.6:1 TT) | 5.373 | Min-to-no | No | Some | Soft | Light Yellow |
| HDI$_{14}$(C62)$_{10.2}$(PEG400)$_{2.5}$DA$_2$ | 1A (1:1 DMDO) | Did not cure | N/A | N/A | N/A | N/A | N/A |
| | 1B (0.6:1 DMDO) | Did not cure | N/A | N/A | N/A | N/A | N/A |
| | 1C (1:1 TT) | 2.126 | No | No | N/A | N/A | Clear |
| | 1D (0.6:1 TT) | 2.223 | No | No | N/A | N/A | Slightly Yellow |
| HDI$_{14.4}$(C62)$_{12}$(PEG400)$_{1.4}$DA$_2$ | 1A (1:1 DMDO) | Did not cure | N/A | N/A | N/A | N/A | N/A |
| | 1B (0.6:1 DMDO) | Did not cure | N/A | N/A | N/A | N/A | N/A |
| | 1C (1:1 TT) | 2.884 | No | No | Yes | Soft-to-med | Light Yellow |
| | 1D (0.6:1 TT) | 3.975 | Min-to-no | Yes | Yes | Soft | Deep Yellow |

TABLE 7

Tested formulations based on copolymers in Table 2.

| PEG400 Containing Copolymers (TPDA End-Capped) | Crosslinker (SH:Vi; Type) | Wagner Force (lbf) | Cohesive Failure Stainless Steel | Dental Cup | Glove | Material Hardness | Material Appearance |
|---|---|---|---|---|---|---|---|
| HDI$_{13.9}$(C62)$_{8.6}$(PEG400)$_{4.3}$TPDA$_2$ | 1A (1:1 DMDO) | 2.542 | Min | No | N/A | Soft-to-med | N/A |
| | 1B (0.6:1 DMDO) | 2.180 | Min | No | N/A | Soft | N/A |
| | 1C (1:1 TT) | 2.908 | No | No | N/A | Hard | N/A |
| | 1D (0.6:1 TT) | 3.658 | Min-to-no | No | N/A | Med-to-hard | N/A |
| MDI$_{8.2}$(C62)$_{5.8}$(PEG400)$_{1.4}$TPDA$_2$ | 1A (1:1 DMDO) | 2.081 | No | Yes | Yes | Soft | Clear |
| | 1B (0.6:1 DMDO) | 3.587 | No | Yes | Yes | Soft | Clear |
| | 1C (1:1 TT) | 1.843 | No | No | Min | Soft-to-med | Slightly Cloudy |
| | 1D (0.6:1 TT) | 4.222 | No | Yes | Yes | Soft-to-med | Slightly Cloudy |
| MDI$_{13.4}$(C62)$_{10}$(PEG400)$_{2.4}$TPDA$_2$ | 1A (1:1 DMDO) | 3.161 | No | Yes | Yes | Soft | Light Yellow |
| | 1B (0.6:1 DMDO) | 2.675 | Yes | Yes | Yes | Soft | Light Yellow |
| | 1C (1:1 TT) | 1.857 | No | No | No | Med-to-hard | Light Yellow |
| | 1D (0.6:1 TT) | 3.174 | Min-to-no | Yes | Yes | Medium | Light Yellow |
| MDI$_{13.9}$(C62)$_{8.6}$(PEG400)$_{4.3}$TPDA$_2$ | 1A (1:1 DMDO) | 2.325 | Min | No | Yes | Medium | Faint Yellow |
| | 1B (0.6:1 DMDO) | 3.367 | Min | No | Yes | Soft | Faint Yellow |
| | 1C (1:1 TT) | 1.538 | No | No | Yes | Med-to-hard | Faint Yellow |
| | 1D (0.6:1 TT) | 2.636 | No | No | Yes | Medium | Faint Yellow |
| HDI$_{14}$(C62)$_{6.5}$(PEG400)$_{6.5}$TPDA$_2$ | 1A (1:1 DMDO) | 4.989 | Min | No | No | Medium | Light Yellow |
| | 1B (0.6:1 DMDO) | 4.815 | Min | No | Min | Soft-to-med | Faint Yellow |
| | 1C (1:1 TT) | 2.278 | Min | No | No | Medium | Faint Yellow |
| | 1D (0.6:1 TT) | 2.859 | Min | No | No | Soft-to-med | Faint Yellow |
| | 1E (1:1 TriT) | 1.805 | No | No | No | Hard | Light Yellow |
| | 1F (0.6:1 TriT) | 3.790 | Min-to-no | No | No | Med-to-hard | Light Yellow |

TABLE 8

Tested formulations based on copolymers in Table 2.

| PEG400 Containing Copolymers (TPDA End-capped), Continued | Crosslinker (SH:Vi; Type) | Wagner Force (lbf) | Cohesive Failure Stainless Steel | Dental Cup | Glove | Material Hardness | Material Appearance |
|---|---|---|---|---|---|---|---|
| $MDI_{14.2}(C62)_{6.6}(PEG400)_{6.6}TPDA_2$ | 1A (1:1 DMDO) | 3.553 | Min | Yes | Yes | Soft-to-med | Light Yellow |
| | 1B (0.6:1 DMDO) | 3.449 | No | Yes | Yes | Soft-to-med | Light Yellow |
| | 1C (1:1 TT) | 3.724 | Min-to-no | Yes | Yes | Soft-to-med | Light Yellow |
| | 1D (0.6:1 TT) | 3.880 | No | Yes | Min | Medium | Light Yellow |
| | 1E (1:1 TriT) | 2.343 | Min-to-no | Yes | Yes | Soft-to-med | Light Yellow |
| | 1F (0.6:1 TriT) | 3.107 | No | Yes | Yes | Soft-to-med | Light Yellow |
| $HDI_{14}(C62)_{6.5}(PEG400)_{6.5}TPDA_2$ | 1A (1:1 DMDO) | 5.339 | Yes | No | No | Medium | Light Yellow |
| | 1B (0.6:1 DMDO) | 4.923 | Yes | Yes | Yes | Soft | Clear |
| | 1C (1:1 TT) | 1.777 | No | No | No | Med-to-hard | Faint Yellow |
| | 1D (0.6:1 TT) | 3.344 | No | No | Min | Soft-to-med | Clear |
| | 1E (1:1 TriT) | 1.840 | No | No | No | Med-to-hard | Faint Yellow |
| | 1F (0.6:1 TriT) | 3.621 | Min-to-no | No | No | Med-to-hard | Faint Yellow |

TABLE 9

Tested formulations based on copolymers in Table 2.

| PEG400 Containing Copolymers (PTAE End-capped) | Crosslinker (SH:Vi; Type) | Wagner Force (lbf) | Cohesive Failure Stainless Steel | Dental Cup | Glove | Material Hardness | Material Appearance |
|---|---|---|---|---|---|---|---|
| $HDI_{14.5}(C62)_9(PEG400)_{4.5}PTAE_2$ | 1A (1:1 DMDO) | 3.292 | No | No | N/A | Soft-to-med | N/A |
| | 1B (0.6:1 DMDO) | 3.657 | Yes | No | N/A | Soft-to-med | N/A |
| | 1C (1:1 TT) | 1.476 | No | Yes | N/A | Hard | N/A |
| | 1D (0.6:1 TT) | 2.638 | Min-to-no | Yes | N/A | Med-to-hard | N/A |
| $MDI_{8.4}(C62)_{6.1}(PEG400)_{1.34}PTAE_2$ | 1A (1:1 DMDO) | 1.700 | No | No | N/A | Soft-to-med | Light Yellow |
| | 1B (0.6:1 DMDO) | 0.717 | No | No | N/A | Soft-to-med | Light Yellow |
| | 1C (1:1 TT) | 0.710 | No | No | N/A | Medium | Slightly Cloudy |
| | 1D (0.6:1 TT) | 2.617 | No | Yes | N/A | Medium | Slightly Cloudy |
| $MDI_{13.8}(C62)_{10.4}(PEG400)_{2.4}PTAE_2$ | 1A (1:1 DMDO) | 0.800 | No | No | N/A | Soft-to-med | Light Yellow |
| | 1B (0.6:1 DMDO) | 1.701 | No | No | N/A | Soft-to-med | Light Yellow |
| | 1C (1:1 TT) | 1.396 | No | No | N/A | Soft-to-med | Light Yellow |
| | 1D (0.6:1 TT) | 1.585 | No | No | N/A | Soft-to-med | Light Yellow |
| $MDI_{13.9}(C62)_{8.6}(PEG400)_{4.3}PTAE_2$ | 1A (1:1 DMDO) | 1.791 | Min-to-no | No | No | Medium | Faint Yellow |
| | 1B (0.6:1 DMDO) | 3.049 | No | No | Min | Soft-to-med | Faint Yellow |
| | 1C (1:1 TT) | 2.137 | Min-to-no | No | No | Hard | Slightly Cloudy |
| | 1D (0.6:1 TT) | 2.423 | Min-to-no | No | Yes | Hard | Slightly Cloudy |
| $MDI_{14.25}(C62)_{9.8}(PEG400)_{4.3}PTAE_2$ | 1A (1:1 DMDO) | 3.681 | Yes | Yes | Yes | Soft | Light Yellow |
| | 1B (0.6:1 DMDO) | 2.113 | Yes | No | Yes | Soft | Light Yellow |
| | 1C (1:1 TT) | 3.327 | Min-to-no | Yes | Yes | Soft | Light Yellow |
| | 1D (0.6:1 TT) | 2.971 | Min-to-no | Yes | Yes | Soft | Light Yellow |

TABLE 10

Tested formulations based on copolymers in Table 2.

| PEG200 Containing Copolymers | Crosslinker (SH:Vi; Type) | Wagner Force (lbf) | Cohesive Failure Stainless Steel | Dental Cup | Glove | Material Hardness | Material Appearance |
|---|---|---|---|---|---|---|---|
| $MDI_{13.9}(C62)_{11.4}(PEG200)_{2.5}TPDA_2$ | 1A (1:1 DMDO) | 2.319 | Yes | Yes | Yes | Soft | Light Yellow |
| | 1B (0.6:1 DMDO) | Did not cure | N/A | N/A | N/A | N/A | N/A |
| | 1C (1:1 TT) | 2.489 | Yes | Yes | Yes | Soft | Light Yellow |
| | 1D (0.6:1 TT) | 2.965 | Yes | Yes | Yes | Soft | Light Yellow |
| $MDI_{14}(C62)_{6.5}(PEG200)_{6.5}TPDA_2$ | 1A (1:1 DMDO) | 1.604 | No | No | No | Med-to-hard | Light Yellow |
| | 1B (0.6:1 DMDO) | 1.097 | No | No | No | Med-to-hard | Light Yellow |
| | 1C (1:1 TT) | 0.710 | No | No | Yes | Hard | Faint Yellow |
| | 1D (0.6:1 TT) | 1.082 | No | No | Yes | Med-to-hard | Light Yellow |
| | 1E (1:1 TriT) | 0.879 | Min-to-no | No | Yes | Hard | Clear |
| | 1F (0.6:1 TriT) | 1.460 | Min-to-no | No | Yes | Hard | Faint Yellow |
| $MDI_{8.8}(C62)_{3.9}(PEG200)_{3.9}TPDA_2$ | 1A (1:1 DMDO) | 2.337 | No | Yes | Yes | Medium | Faint Yellow |
| | 1B (0.6:1 DMDO) | 3.825 | No | Yes | Yes | Soft-to-med | Faint Yellow |
| | 1C (1:1 TT) | 2.809 | Min-to-no | Yes | Yes | Hard | Faint Yellow |
| | 1D (0.6:1 TT) | 3.185 | No | Yes | Yes | Soft-to-med | Faint Yellow |
| | 1E (1:1 TriT) | 3.072 | No | Yes | Yes | Soft | Faint Yellow |
| | 1F (0.6:1 TriT) | 3.279 | No | Yes | Yes | Soft | Faint Yellow |

TABLE 11

Tested formulations based on copolymers in Table 2.

| PEG-PPG Containing Copolymers (PEG-PPG-PEG1100) | Crosslinker (SH:Vi; Type) | Wagner Force (lbf) | Cohesive Failure Stainless Steel | Dental Cup | Glove | Material Hardness | Material Appearance |
|---|---|---|---|---|---|---|---|
| $MDI_{14.6}(C62)_{11.4}(PEG\text{-}PPG\text{-}PEG1100)_{2.5}TPDA_2$ | 1A (1:1 DMDO) | Did not cure | N/A | N/A | N/A | N/A | N/A |
| | 1B (0.6:1 DMDO) | Did not cure | N/A | N/A | N/A | N/A | N/A |
| | 1C (1:1 TT) | 3.037 | No | Yes | Yes | Soft | Light Yellow |
| | 1D (0.6:1 TT) | 2.930 | Min-to-no | Yes | Yes | Soft | Light Yellow |
| $HDI_{13.6}(C62)_{11.1}(PEG\text{-}PPG\text{-}PEG1100)_{2.1}TPDA_2$ | 1A (1:1 DMDO) | 2.139 | Min | Yes | Min | Soft | Light Yellow |
| | 1B (0.6:1 DMDO) | 1.865 | Yes | Yes | Yes | Soft | Light Yellow |
| | 1C (1:1 TT) | 1.875 | Min | Yes | No | Hard | Light Yellow |
| | 1D (0.6:1 TT) | 2.226 | Min | Yes | Min | Soft-to-med | Light Yellow |
| $HDI_{8.56}(C62)_{6.3}(PEG\text{-}PPG\text{-}PEG1100)_{1.26}TPDA_2$ | 1A (1:1 DMDO) | 1.193 | Min | No | Min-to-no | Medium | Faint Yellow |
| | 1B (0.6:1 DMDO) | 1.746 | Min | Yes | No | Soft | Light Yellow |
| | 1C (1:1 TT) | 0.819 | No | No | No | Med-to-hard | Faint Yellow |
| | 1D (0.6:1 TT) | 1.620 | Min-to-no | No | No | Medium | Faint Yellow |

TABLE 12

Tested formulations based on copolymers in Table 2.

| PEG-PPG Copolymers (PEG-PPG-PEG1900) | Crosslinker (SH:Vi; Type) | Wagner Force (lbf) | Cohesive Failure Stainless Steel | Dental Cup | Glove | Material Hardness | Material Appearance |
|---|---|---|---|---|---|---|---|
| $MDI_{14.2}(C62)_{12.5}(PEG\text{-}PPG\text{-}PEG1900)_{1.4}TPDA_2$ | 1A (1:1 DMDO) | 2.888 | Yes | Yes | Yes | Soft | Light Yellow |
| | 1B (0.6:1 DMDO) | 2.191 | Yes | Yes | Yes | Soft | Light Yellow |

TABLE 12-continued

Tested formulations based on copolymers in Table 2.

| PEG-PPG Copolymers (PEG-PPG-PEG1900) | Crosslinker (SH:Vi; Type) | Wagner Force (lbf) | Cohesive Failure Stainless Steel | Cohesive Failure Dental Cup | Cohesive Failure Glove | Material Hardness | Material Appearance |
|---|---|---|---|---|---|---|---|
| | 1C (1:1 TT) | 3.103 | No | Yes | Yes | Soft | Light Yellow |
| | 1D (0.6:1 TT) | 3.175 | Min-to-no | Yes | Yes | Soft | Light Yellow |
| $HDI_{14.2}(C62)_{12.5}(PEG\text{-}PPG\text{-}PEG1900)_{1.4}TPDA_2$ | 1A (1:1 DMDO) | 1.452 | Yes | Yes | Yes | Soft | Faint Yellow |
| | 1B (0.6:1 DMDO) | 1.594 | Yes | Yes | Yes | Soft | Faint Yellow |
| | 1C (1:1 TT) | 1.063 | No | No | Min | Medium | Light Yellow |
| | 1D (0.6:1 TT) | 2.441 | Min | Yes | Min | Soft | Light Yellow |
| $HDI_{8.2}(C62)_{6.9}(PEG\text{-}PPG\text{-}PEG1900)_{0.77}TPDA_2$ | 1A (1:1 DMDO) | 1.423 | Min | No | No | Med-to-hard | Light Yellow |
| | 1B (0.6:1 DMDO) | 2.089 | Min-to-no | Yes | No | Soft | Light Yellow |
| | 1C (1:1 TT) | 0.811 | Min-to-no | No | No | Medium | Clear |
| | 1D (0.6:1 TT) | 1.344 | No | No | No | Soft-to-med | Clear |

TABLE 13

Tested formulations based on copolymers in Table 2.

| PEG-PPG Containing Copolymers (PEG-PPG-ran2500) | Crosslinker (SH:Vi; Type) | Wagner Force (lbf) | Cohesive Failure Stainless Steel | Cohesive Failure Dental Cup | Cohesive Failure Glove | Material Hardness | Material Appearance |
|---|---|---|---|---|---|---|---|
| $MDI_{13.4}(C62)_{12}(PEG\text{-}PPG\text{-}ran2500)_1TPDA_2$ | 1A (1:1 DMDO) | 2.987 | Yes | Yes | Yes | Soft | Faint Yellow |
| | 1B (0.6:1 DMDO) | 3.279 | Yes | Yes | Yes | Soft | Faint Yellow |
| | 1C (1:1 TT) | 2.462 | No | Yes | Yes | Soft | Faint Yellow |
| | 1D (0.6:1 TT) | 3.128 | Min | Yes | Yes | Soft | Faint Yellow |
| $HDI_{13.8}(C62)_{12.4}(PEG\text{-}PPG\text{-}ran2500)_{1.01}TPDA_2$ | 1A (1:1 DMDO) | 2.509 | Min | Yes | Yes | Soft-to-med | Faint Yellow |
| | 1B (0.6:1 DMDO) | Did not cure | N/A | N/A | N/A | N/A | Faint Yellow |
| | 1C (1:1 TT) | 1.796 | No | Yes | Min | Medium | Clear |
| | 1D (0.6:1 TT) | 2.353 | Yes | Yes | Yes | Soft | Clear |

TABLE 14

Tested formulations based on copolymers in Table 2.

| Copolymers with Additives | Additive | Wagner Force (lbf) | Cohesive Failure Stainless Steel | Cohesive Failure Dental Cup | Cohesive Failure Glove | Material Hardness | Material Appearance |
|---|---|---|---|---|---|---|---|
| $HDI_{13.5}(C16)_{12.5}DA_2$ Salicyclic Acid | Salicyclic Acid | 1.05 | Yes | N/A | N/A | N/A | N/A |
| | Lidocaine | 1.19 | Yes | N/A | N/A | N/A | N/A |
| | Microsized CMC | 2.498 | Min-to-no | Yes | N/A | Med-to-soft | Yellow |
| | 10% PEG Diacrylate | 2.921 | Yes | Yes | N/A | Soft | N/A |
| | Polyox15 | 3.025 | Min | Min | N/A | Med-to-hard | N/A |

TABLE 15

Adhesion and Release Force from Coatings of Selected Compositions

| Formulation | Composition | Adhesion (N/In) | Release (N/In) |
|---|---|---|---|
| $HDI_{13.9}(C62)_{8.6}(PEG400)_{4.3}TPDA_2$ | 1C (1:1 TT) | 0.219 | 0.010 |
| $HDI_{13.9}(C62)_{8.6}(PEG400)_{4.3}TPDA_2$ | 1D (0.6:1 TT) | 1.141 | 0.055 |
| $HDI_{13.9}(C62)_{8.6}(PEG400)_{4.3}TPDA_2$ | 1C (1.35:1 DMDO) | 3.635 | 0.064 |
| $HDI_{13.5}(C16)_{12.5}DA_2$ | 1A/C (1:1 Blend) | 3.101 | 1.677 |
| $HDI_{14.4}(C62)_{6.5}(PEG400)_{6.5}DA_2$ | 1D (0.6:1 TT) | 3.522 | 0.036 |
| $HDI_{13.7}(C62)_{12.7}TPDA_2$ | 1D (0.6:1 TT) | 1.475 | 0.597 |

TABLE 15-continued

Adhesion and Release Force from Coatings of Selected Compositions

| Formulation | Composition | Adhesion (N/In) | Release (N/In) |
|---|---|---|---|
| $HDI_{13.7}(C62)_{12.7}TPDA_2$ | 1C (1:1 TT) | 0.475 | 0.047 |
| $HDI_{13.9}(C62)_{12.0}PTAE_2$ | 1D (0.6:1 TT) | 0.612 | 0.166 |
| $HDI_{14.5}(C62)_9(PEG400)_{4.5}PTAE_2$ | 1A (1:1 DMDO) | 1.534 | 0.032 |
| $HDI_{14.5}(C62)_9(PEG400)_{4.5}PTAE_2$ | 1C (0.6:1 TT) | 0.470 | 0.022 |
| $MDI_{8.2}(C62)_{5.8}(PEG400)_{1.4}TPDA_2$ | 1B (0.6:1 DMDO) | 0.650 | 0.024 |
| $MDI_{8.2}(C62)_{5.8}(PEG400)_{1.4}TPDA_2$ | 1C (0.6:1 DMDO) | 0.240 | 0.015 |
| $MDI_{13.4}(C62)_{10}(PEG400)_{2.4}TPDA_2$ | 1A (1:1 DMDO) | 0.688 | 0.021 |
| $MDI_{13.4}(C62)_{10}(PEG400)_{2.4}TPDA_2$ | 1D (0.6:1 TT) | 0.991 | 0.022 |
| $MDI_{13.8}(C62)_{10.4}(PEG400)_{2.4}PTAE_2$ | 1D (0.6:1 TT) | 0.269 | 0.011 |
| $HDI_{13.6}(C62)_{11.1}(PEG-PPG-PEG1100)_{2.1}TPDA_2$ | 1D (0.6:1 TT) | 1.607 | 0.768 |
| $HDI_{14}(C62)_{6.5}(PEG400)_{6.5}TPDA_2$ | 1A (1:1 DMDO) | 7.719 | 0.023 |
| $HDI_{14}(C62)_{6.5}(PEG400)_{6.5}TPDA_2$ | 1D (0.6:1 TT) | 0.112 | 0.002 |
| $HDI_{8.56}(C62)_{6.3}(PEG-PPG-PEG1100)_{1.26}TPDA_2$ | 1B (0.6:1 DMDO) | 0.357 | 0.590 |
| $HDI_{8.2}(C62)_{6.9}(PEG-PPG-PEG1900)_{0.77}TPDA_2$ | 1B (0.6:1 DMDO) | 0.455 | 0.296 |
| $HDI_{14}(C62)_{6.5}(PEG400)_{6.5}TPDA_2$ | 1A (1:1 DMDO) | 7.972 | 0.040 |

TABLE 16

Moisture Vapor Transmission Data of Films from Selected Compositions

| Formulation | Composition | MVTR Upright | MVTR Inverted | Permeability Upright | Permeability Inverted |
|---|---|---|---|---|---|
| $HDI_{13.9}(C62)_{8.6}(PEG400)_{4.3}TPDA_2$ | 1.35C (1:35 DMDO) | 493 | 656 | 4.47 | 105 |
| $HDI_{13.5}(C16)_{12.5}DA_2$ | 1 A/C (25/75) | 282 | 693 | 3.21 | 113 |
| $HDI_{13.5}(C16)_{12.5}DA_2$ | 1 A/C (50/50) | 246 | 1491* | 2.88 | 345* |
| $HDI_{14.4}(C62)_{6.5}(PEG400)_{6.5}DA_2$ | 1A (1:1 DMDO) | N/A | 334 | N/A | 142 |
| $HDI_{14}(C62)_{6.5}(PEG400)_{6.5}TPDA_2$ | 1D (0.6:1 TT) | 628 | 688 | 6.07 | 114 |
| $HDI_{14}(C62)_{6.5}(PEG400)_{6.5}TPDA_2$ | 1A (1:1 DMDO) | 620 | 786 | 6.20 | 124 |
| $HDI_{8.56}(C62)_{6.3}(PEG-PPG-PEG1100)_{1.26}TPDA_2$ | 1B (0.6:1 DMDO) | 436 | 503 | 3.05 | 63.4 |
| $HDI_{8.2}(C62)_{6.9}(PEG-PPG-PEG1900)_{0.77}TPDA_2$ | 1B (0.6:1 DMDO) | 613 | 622 | 4.44 | 87.9 |
| $HDI_{14}(C62)_{6.5}(PEG400)_{6.5}TPDA_2$ | 1A (1:1 DMDO) | 535 | 877 | 6.50 | 123 |

INDUSTRIAL APPLICABILITY

The examples above show that the copolymers described herein may provide various benefits, including imparting to crosslinked compositions, such as skin contact adhesives, improved permeability to liquids such as water, improved vapor permeability (e.g., water vapor permeability) than previously disclosed copolymers. The copolymers described herein may also be used to form free standing films, thereby minimizing or eliminating the need for substrates in certain applications.

Definitions and Usage of Terms

All amounts, ratios, and percentages are by weight unless otherwise indicated. The articles 'a', 'an', and 'the' each refer to one or more, unless otherwise indicated by the context of specification. The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range. Similarly, the disclosure of Markush groups includes the entire group and also any individual members and subgroups subsumed therein. For example, disclosure of the Markush group a hydrogen atom, an alkyl group, an alkenyl group, an alkynyl group, and an aryl group, an includes the member alkyl individually; the subgroup alkyl and aryl; and any other individual member and subgroup subsumed therein.

"Alkyl" means a saturated monovalent hydrocarbon group. Alkyl is exemplified by, but not limited to, methyl, ethyl, propyl (e.g., iso-propyl and/or n-propyl), butyl (e.g., isobutyl, n-butyl, tert-butyl, and/or sec-butyl), pentyl (e.g., isopentyl, neopentyl, and/or tert-pentyl); hexyl, heptyl, octyl, nonyl, and decyl, as well as branched saturated monovalent hydrocarbon groups of 6 or more carbon atoms.

"Alkenyl" means a monovalent hydrocarbon group containing a double bond. Alkenyl groups are exemplified by, but not limited to, ethenyl, propenyl (e.g., iso-propenyl and/or n-propenyl), butenyl (e.g., isobutenyl, n-butenyl, tert-butenyl, and/or sec-butenyl), pentenyl (e.g., isopentenyl, n-pentenyl, and/or tert-pentenyl), hexenyl, heptenyl, octenyl, nonenyl, and decenyl, as well as such branched groups of 6 or more carbon atoms.

"Alkynyl" means a monovalent hydrocarbon group containing a triple bond. Alkynyl groups are exemplified by, but not limited to, ethynyl, propynyl (e.g., iso-propynyl and/or n-propynyl), butynyl (e.g., isobutynyl, n-butynyl, tert-butynyl, and/or sec-butynyl), pentynyl (e.g., isopentynyl, n-pentynyl, and/or tert-pentynyl), hexynyl, heptynyl, octynyl, nonynyl, and decynyl, as well as such branched groups of 6 or more carbon atoms.

"Aryl" means a cyclic, fully unsaturated, hydrocarbon group. Aryl is exemplified by, but not limited to, cyclopentadienyl, phenyl, anthracenyl, and naphthyl. Monocyclic aryl groups may have 5 to 9 carbon atoms, alternatively 6 to 7 carbon atoms, and alternatively 5 to 6 carbon atoms. Polycyclic aryl groups may have 10 to 18 carbon atoms, alternatively 10 to 14 carbon atoms, and alternatively 12 to 14 carbon atoms.

"Aralkyl" means an alkyl group having a pendant and/or terminal aryl group or an aryl group having a pendant alkyl group. Exemplary aralkyl groups include tolyl, xylyl, benzyl, phenylethyl, phenyl propyl, and phenyl butyl.

"Carbocycle" and "carbocyclic" each mean a hydrocarbon ring. Carbocycles may be monocyclic or alternatively may be fused, bridged, or spiro polycyclic rings. Monocyclic carbocycles may have 3 to 9 carbon atoms, alternatively 4 to 7 carbon atoms, and alternatively 5 to 6 carbon atoms. Polycyclic carbocycles may have 7 to 18 carbon atoms, alternatively 7 to 14 carbon atoms, and alternatively 9 to 10 carbon atoms. Carbocycles may be saturated or partially unsaturated.

"Cycloalkyl" means saturated carbocycle. Monocyclic cycloalkyl groups are exemplified by cyclobutyl, cyclopentyl, and cyclohexyl.

Collectively, the term "monovalent hydrocarbon group" includes alkyl, alkenyl, aryl, aralkyl, and carbocyclic groups, as defined above.

"Divalent hydrocarbon group" includes alkylene groups such as ethylene, propylene (including isopropylene and n-propylene), and butylene (including n-butylene, t-butylene and isobutylene); and pentylene, hexylene, heptylene, octylene, and branched and linear isomers thereof; arylene groups such as phenylene; and alkaralkylene groups such as:

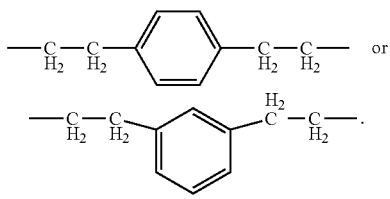

or

Alternatively, each divalent hydrocarbon group may be ethylene, propylene, butylene or hexylene. Alternatively, each divalent hydrocarbon group may be ethylene or propylene.

"Halogenated hydrocarbon" means a hydrocarbon group as defined above, but where one or more hydrogen atoms bonded to a carbon atom have been formally replaced with a halogen atom. For example, monovalent halogenated hydrocarbon groups can be any one of alkyl, alkenyl, aryl, aralkyl, and carbocyclic groups in which one or more hydrogen atoms bonded to a carbon atom have been replaced with a halogen atom. Monovalent halogenated hydrocarbon groups include haloalkyl groups, halogenated carbocyclic groups, and haloalkenyl groups. Haloalkyl groups include fluorinated alkyl groups such as trifluoromethyl ($CF_3$), fluoromethyl, trifluoroethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4, 3,3-nonafluorohexyl, and 8,8,8,7,7-pentafluorooctyl; and chlorinated alkyl groups such as chloromethyl and 3-chloropropyl. Halogenated carbocyclic groups include fluorinated cycloalkyl groups such as 2,2-difluorocyclopropyl, 2,3-difluorocyclobutyl, 3,4-difluorocyclohexyl, and 3,4-difluoro-5-methylcycloheptyl; and chlorinated cycloalkyl groups such as 2,2-dichlorocyclopropyl, 2,3-dichlorocyclopentyl. Haloalkenyl groups include chloro allyl.

"Skin" includes stratum corneum covered skin and mucosal membranes.

"Transdermal" means being able to pass through unbroken skin. "Skin" includes stratum corneum covered skin and mucosal membranes.

The invention claimed is:

1. A copolymer that has formula (I):

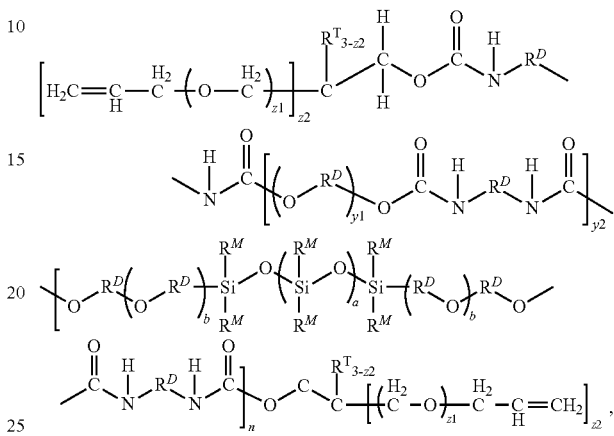

where each $R^T$ is hydrogen or a monovalent hydrocarbon group; each $R^D$ is independently a divalent hydrocarbon group or a divalent halogenated hydrocarbon group; each $R^M$ is independently a monovalent hydrocarbon group or a monovalent halogenated hydrocarbon group: each subscript y1 is independently greater than 0: subscript y2 is greater than 0: each subscript a is independently 0 to 1,000,000; each subscript b is independently greater than or equal to 0; subscript n is greater than or equal to 1; subscript n is 1 to 1,500,000; each subscript Z2 is greater than 1 and less than or equal to 3; each subscript Z1 is from 1 to 15.

2. A composition comprising the copolymer of claim 1 and at least one additional ingredient.

3. The composition of claim 2, where the at least one additional ingredient comprises a carrier that permits application to skin, hair, or a substrate made of or from a polymer, a metal, or a ceramic material.

4. The composition of claim 2, where the at least one additional ingredient comprises a curing catalyst.

5. The composition of claim 4, further comprising one or more additional starting materials selected from a crosslinker and an excipient.

6. The composition of claim 5, where the crosslinker is present, and the crosslinker is selected from an acrylate crosslinker, a crosslinker containing alkenyl groups other than in an acrylate group, a thiol-functional crosslinker, or an SiH containing crosslinker.

7. A method comprising formulating a skin contact adhesive composition including the composition of claim 4 and crosslinking to prepare a skin contact adhesive.

8. A method for making a laminate article, the method comprising:
   (i) forming a layer of a skin contact adhesive composition comprising the copolymer of claim 3, a curing catalyst, and a crosslinker on at least a portion of a skin facing surface of a support,
   (ii) crosslinking the skin contact adhesive composition to form the skin contact adhesive.

* * * * *